US006599590B2

(12) United States Patent
Haseba et al.

(10) Patent No.: US 6,599,590 B2
(45) Date of Patent: Jul. 29, 2003

(54) FLUORO-SUBSTITUTED ALKENYL COMPOUNDS, LIQUID CRYSTAL COMPOSITIONS, AND LIQUID CRYSTAL DISPLAY ELEMENTS

(75) Inventors: Yasuhiro Haseba, Ichihara (JP); Shuichi Matsui, Ichihara (JP); Hiroyuki Takeuchi, Ichihara (JP); Yasuhiro Kubo, Ichihara (JP); Etsuo Nakagawa, Ichihara (JP)

(73) Assignees: Chisso Corporation, Osaka (JP); Chisso Petrochemical Corporation, Tokyo (JP)

( * ) Notice: Subject to any disclaimer, the term of this patent is extended or adjusted under 35 U.S.C. 154(b) by 120 days.

(21) Appl. No.: 09/861,554

(22) Filed: May 22, 2001

(65) Prior Publication Data

US 2002/0015805 A1 Feb. 7, 2002

(30) Foreign Application Priority Data

May 22, 2000 (JP) ...................................... 2000-150112

(51) Int. Cl.$^7$ ........................ C09K 19/30; C09K 19/34; C09K 19/12; C07C 25/13; C07C 25/24

(52) U.S. Cl. .............. 428/1.1; 252/299.61; 252/299.63; 252/299.66; 570/128; 570/129; 570/144

(58) Field of Search ....................... 252/299.63, 299.66, 252/299.61; 428/1.1; 570/127, 128, 129, 144

(56) References Cited

U.S. PATENT DOCUMENTS 5,183,587 A * 2/1993 Kitano et al. .......... 252/299.63

FOREIGN PATENT DOCUMENTS

| | | |
|---|---|---|
| EP | 0330216 A2 | 8/1989 |
| EP | 0 377 469 | 7/1990 |
| WO | 91/06522 | 5/1991 |

OTHER PUBLICATIONS

Mancuso, Anthony J., Shui–Lung Huang, and Daniel Swern, *Oxidation of Long–Chain and Related Alcohols to Carbonyls by Dimethyl Sulfoxide "Activated" by Oxalyl Chloride*, J. Org. Chem., vol. 43, No. 12, 1987, pp. 2480–2483.

Gray, George W., Michael Hird, David Lacey, and Kenneth J, Toyne. *The Synthesis and Transition Temperatures of some 4,4"–Dialkyl– and 4,4"–Alkoxyalkyl–1,1': 4',1"–terphenyls with 2,3– or 2',3'–Difluoro Substituents and of their Biphenyl Analogues*, J. Chem. Soc. Perkin Trans. II 1989, pp. 2041–2053.

Suzuki, Akira, *Cross–coupling Reactions of Organoboron Compounds with Organic Halides*, Eds. F. Dietrich, P.J. Stang, Wiley–VCH, Weiheim, 1998, pp. 49–97.

Suzuki, H., *Direct Iodination of Polyalkylbenzenes: Iododurene*, Organic Synthesis VI (1988), pp. 700–705.

Hori, Keiko, and Yasufumi Ohfune. *Synthesis and Absolute Structure of Galantinamic Acid*, J. Org. Chem. vol. 53, 1988, pp. 3886–3888.

Kitano, K., et al. "New Liquid Crystalline Compounds Incorporating some Fluoroalkenyl Wing Groups", Mol. Cryst. Liq. Cryst., vol. 191 (1990), pp. 205–209.

* cited by examiner

*Primary Examiner*—Shean C. Wu
(74) *Attorney, Agent, or Firm*—Wenderoth, Lind & Ponack, L.L.P.

(57) ABSTRACT

The invention relates to a fluoro-substituted alkenyl compound represented by formula (1)

(1)

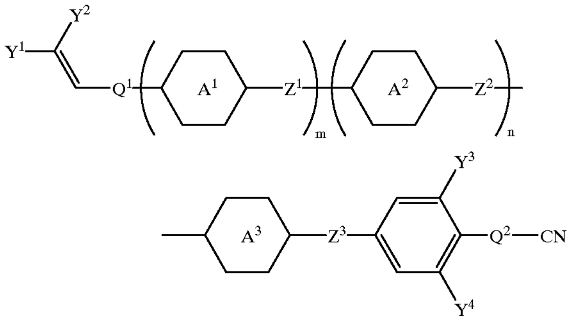

wherein $Y^1$, $Y^2$, $Y^3$ and $Y^4$ are each independently H or F, provided that at least one of $Y^1$ and $Y^2$ is F; $Q^1$ is a single bond or an alkylene group of 1–20 carbon atoms, at least one —$CH_2$— being optionally substituted by —O—, provided that two or more —O— are not adjacent to each other; $Q^2$ is a single bond or —C≡C—; Rings $A^1$, $A^2$ and $A^3$ are each independently a cyclohexane ring, a dioxane ring, a cyclohexene ring, a pyrimidine ring, a pyridine ring, or a benzene ring, or a benzene ring having at least one hydrogen atom substituted by F; $Z^1$, $Z^2$ and $Z^3$ are each independently a single bond, —$CH_2CH_2$—, —$CH_2O$—, —$OCH_2$—, —COO—, —OCO—, —CH=CH—, —C≡C—, —$CF_2O$—, or —$OCF_2$; and m and n are each independently 0 or 1; provided that $Y^3$ is F when Ring $A^3$ is a cyclohexane ring and $Z^3$ is a single bond. The liquid crystal composition comprising the compound, when used in liquid crystal display elements for various modes, excels in driving voltage and contrast.

30 Claims, No Drawings

FLUORO-SUBSTITUTED ALKENYL COMPOUNDS, LIQUID CRYSTAL COMPOSITIONS, AND LIQUID CRYSTAL DISPLAY ELEMENTS

TECHNICAL FIELD

This invention relates to liquid crystalline compounds and liquid crystal compositions, and more particularly, to liquid crystalline fluoro-substituted alkenyl compounds as a suitable component for the liquid crystal compositions especially for TN mode, STN mode, TFT mode, and OCB mode, liquid crystal compositions comprising such compounds, and liquid crystal display elements comprising such liquid crystal compositions.

The expression "liquid crystalline compound" is used herein as the general term for a compound possessing a liquid crystal phase and a compound exhibiting no liquid crystal phase and yet serving as a useful constitutional component for a liquid crystal composition.

RELATED ART

The liquid crystal display element utilizes the optical anisotropy and the dielectric anisotropy possessed by a liquid crystal substance. It is sorted into various types according to the display mode such as twisted nematic (TN) mode, dynamic scattering (DS) mode, guest-host (G-H) mode, deforming of aligned phases (DAP) mode, supertwisted nematic (STN) mode, voltage control birefringence (VCB, ECB, or TB) mode, vertical aligning (VA) mode, multidomain vertical aligning (MVA) mode and OCB mode, utilizing liquid crystal substances with different properties suitable for each mode. The liquid crystal substances which are used for these display modes are required to be stable to moisture, air, heat, and light.

A liquid crystal display element requiring a lower driving voltage and yet manifesting a high contrast has been demanded in these years. For the purpose of lowering the driving voltage, it is important to increase dielectric anisotropy value (Δ∈) of a given liquid crystal material. Particularly, for the purpose of heightening the contrast of the liquid crystal display element of the STN mode, the curve of voltage transmittance of a given liquid crystal display element needs to be very steep. For this, a large elastic constant ratio ($K_{33}/K_{11}$) of the liquid crystal material is required.

EP 0330216 A discloses the below (1-a) and WO91/06522 discloses the below (1-b), as a liquid crystal material exhibiting a positive dielectric anisotropy value.

(1-a)

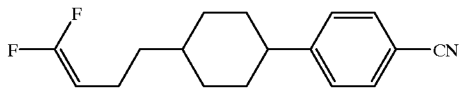

(1-b)

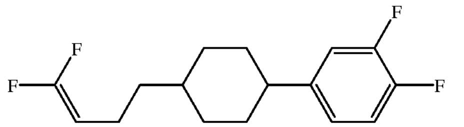

These compounds, however, have small Δ∈ and small $K_{33}/K_{11}$ ratio and thus are not sufficient for solving the problems mentioned above. Though WO91/06522 claims the compounds containing a cyano group, the description discloses neither the structure nor the data of such compounds.

SUMMARY OF THE INVENTION

An object of the present invention is to provide a liquid crystalline compound which has a broad temperature range for liquid crystal phases applicable to various modes of liquid crystal display elements, can show any optical anisotropy value (Δn) depending on combination of factors such as a ring structure and a substituent, and is stable against the influence of moisture, air, heat, and light.

More specifically, the invention aims at providing a liquid crystalline compound which eliminates the conventional technical defects mentioned above thereby possessing a large Δ∈ and a large $K_{33}/K_{11}$ ratio.

Another object of the invention is to provide a liquid crystal composition comprising the above compound, which can impart the merits of a low driving voltage and a high contrast to a liquid crystal display element.

Further object of the invention is to provide a liquid crystal display element comprising the liquid crystal composition.

The present inventors, as a result of diligent study, have found that the following liquid crystalline compounds possess a large Δ∈ and a large $K_{33}/K_{11}$ ratio.

More specifically, (a) the compounds of the following formula (1) wherein the ring $A^3$ is not a cyclohexane ring; (b) the compounds represented by the formula (1) which contain a monofluoroalkenyl group or a difluoroalkenyl group when the ring $A^3$ is a cyclohexane ring and $Z^3$ is not a single bond and which further contain a cyano group; and (c) the compounds represented by the formula (1) which contain a monofluoroalkenyl group or a difluoroalkenyl group when the ring $A^3$ is a cyclohexane ring and $Z^3$ is a single bond and which contain, in addition to a cyano group, a benzene ring having at least one hydrogen atom substituted by F.

The present inventors have further found that the liquid crystal compositions comprising such compounds are the materials best suitable for achieving a low driving voltage and the manifestation of a high contrast in various liquid crystal display elements, and finally completed the present invention.

DETAILED DESCRIPTION OF THE INVENTION

The present invention provides a fluoro-substituted alkenyl compound represented by the formula (1):

(1)

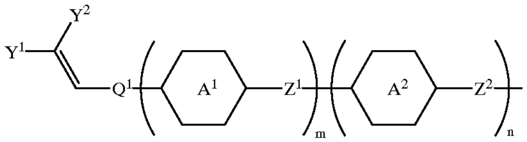

-continued

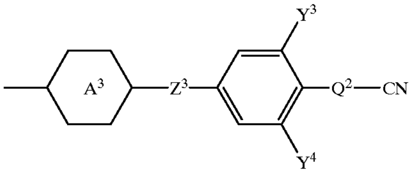

wherein $Y^1$, $Y^2$, $Y^3$ and $Y^4$ are each independently H or F, provided that at least one of $Y^1$ and $Y^2$ is F; $Q^1$ is a single bond or an alkylene group of 1–20 carbon atoms, at least one —$CH_2$— being optionally substituted by —O—, provided that two or more —O— are not adjacent to each other; $Q^2$ is a single bond or —C≡C—; Rings $A^1$, $A^2$and $A^3$ are each independently a cyclohexane ring, a dioxane ring, a cyclohexene ring, a pyrimidine ring, a pyridine ring, or a benzene ring, or a benzene ring having at least one hydrogen atom substituted by F; $Z^1$, $Z^2$ and $Z^3$ are each independently a single bond, —$CH_2CH_2$—, —$CH_2O$—, —$OCH_2$—, —COO—, —OCO—, —CH=CH—, —C≡C—, —$CF_2O$—, or —$OCF_2$; and m and n are each independently 0 or 1; provided that $Y^3$ is F when Ring $A^3$ is a cyclohexane ring and $Z^3$ is a single bond.

This invention further provides a fluoro-substituted alkenyl compound represented by the formula (1) wherein m and n are both 0.

This invention further provides a fluoro-substituted alkenyl compound represented by the formula (1) wherein Ring $A^3$ is a dioxane ring, a cyclohexene ring, a pyrimidine ring, a pyridine ring, or a benzene ring, or a benzene ring having at least one hydrogen atom substituted by F.

In one embodiment of the invention, there is provided a fluoro-substituted alkenyl compound represented by the formula (1) wherein Ring $A^3$ is a cyclohexane ring.

In another embodiment of the invention, there is provided a fluoro-substituted alkenyl compound represented by the formula (1) wherein $Z^3$ is —COO—.

In another embodiment of the invention, there is provided a fluoro-substituted alkenyl compound represented by the formula (1) wherein both $Y^1$ and $Y^2$ are F.

This invention also provides a liquid crystal composition comprising a fluoro-substituted alkenyl compound represented by the formula (1).

This invention further provides a liquid crystal composition comprising as a first component a fluoro-substituted alkenyl compound represented by the formula (1) and as a second component a compound selected from the group consisting of the compounds represented by the formulas (2), (3) and (4)

(2)

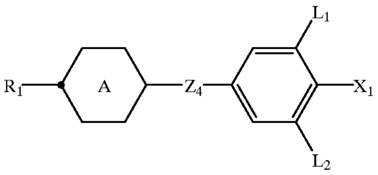

-continued (3)

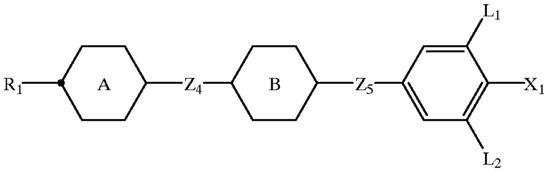

(4)

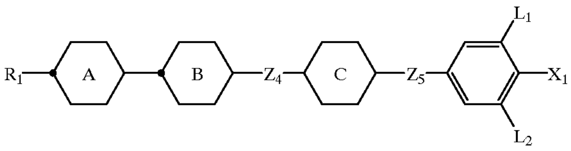

wherein $R_1$ is an alkyl group of 1–10 carbon atoms, at least one —$CH_2$— being optionally substituted by —O— or —CH=CH—, provided that two or more of —O— are not adjacent to each other, and at least one H atom being optionally substituted by F; $X_1$ is F, Cl, $OCF_3$, —$OCF_2H$, —$CF_3$, —$CF_2H$, —$CFH_2$, —$OCF_2CF_2H$, or —$OCF_2CFHCF_3$; $L_1$ and $L_2$ are each independently H or F; $Z_4$ and $Z_5$ are each independently —$(CH_2)_2$, —$(CH_2)_4$—, —COO—, —$CF_2O$—, —$OCF_2$—, —CH=CH—, or a single bond; Rings A and B are each independently a cyclohexane ring, a dioxane ring, or a benzene ring, or a benzene ring having at least one hydrogen atom substituted by F; and Ring C is a cyclohexane ring, a benzene ring, or a benzene ring having at least one hydrogen atom substituted by F.

The invention further provides a liquid crystal composition comprising as a first component a fluoro-substituted alkenyl compound represented by the formula (1) and as a second component a compound selected from the group consisting of the compounds represented by the formulas (5) and (6)

(5)

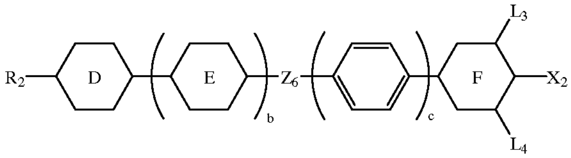

(6)

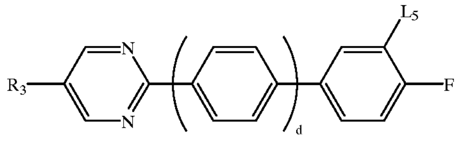

wherein $R_2$ and $R_3$ are each independently an alkyl group of 1–10 carbon atoms, at least one —$CH_2$— being optionally substituted by —O— or —CH=CH—, provided that two or more of —O— are not adjacent to each other, and at least one H atom being optionally substituted by F; $X_2$ is —CN or —C≡C—CN; Ring D is a cyclohexane ring, a benzene ring, a dioxane ring, or a pyrimidine ring; Ring E is a cyclohexane ring, a benzene ring, a benzene ring having at least one hydrogen atom substituted by F, or a pyrimidine ring; Ring F is a cyclohexane ring or a benzene ring; $Z_6$ is —$(CH_2)_2$—, —COO—, —$CF_2O$—, —$OCF_2$—, or a single bond; $L_3$, $L_4$ and $L_5$ are each independently H or F; and b, c and d are each independently 0 or 1.

The invention further provides a liquid crystal composition comprising as a first component a fluoro-substituted alkenyl compound represented by the formula (1) and as a second component a compound selected from the group consisting of the compounds represented by the formulas (7), (8) and (9)

(7)

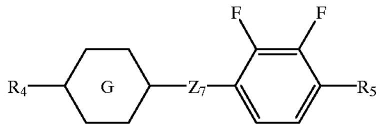

(8)

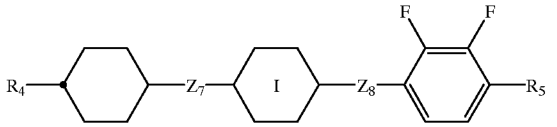

(9)

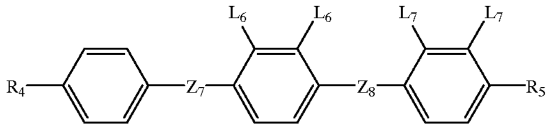

wherein $R_4$ and $R_5$ are each independently an alkyl group of 1–10 carbon atoms, at least one —$CH_2$— being optionally substituted by —O— or —CH═CH—, provided that two or more of —O— are not adjacent to each other, and at least one H atom being optionally substituted by F; Rings G and I are each independently a cyclohexane ring or a benzene ring; $L_6$ and $L_7$ are each independently H or F, provided that $L_6$ and $L_7$ are not simultaneously H; and $Z_7$ and $Z_8$ are each independently —$(CH_2)_2$—, —COO—, or a single bond.

The invention further provides a liquid crystal composition which comprises as a first component a fluoro-substituted alkenyl compound represented by the formula (1), as a second component a compound selected from the group consisting of the compounds represented by the formulas (2), (3) and (4), and as a third component a compound selected from the group consisting of the compounds represented by the formulas (10), (11) and (12)

(10)

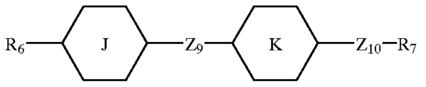

(11)

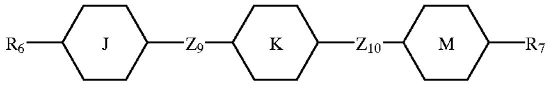

(12)

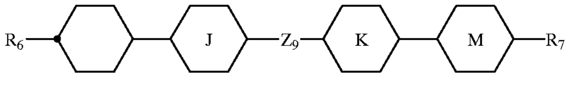

wherein $R_6$ and $R_7$ are each independently an alkyl group of 1–10 carbon atoms, at least one —$CH_2$— being optionally substituted by —O— or —CH═CH—, provided that two or more of —O— are not adjacent to each other, and any of H atoms in the group being optionally substituted by F; Rings J, K and M are each independently a cyclohexane ring, pyrimidine ring, a benzene ring, or a benzene ring having at least one H atom substituted by F; and $Z_9$ and $Z_{10}$ are each independently —C≡C—, —COO—, —$(CH_2)_2$—, —CH═CH—, or a single bond.

The invention further provides a liquid crystal composition which comprises as a first component a fluoro-substituted alkenyl compound represented by the formula (1), as a second component a compound selected from the group consisting of the compounds represented by the formulas (5) and (6), and as a third component a compound selected from the group consisting of the compounds represented by the formulas (10), (11) and (12).

The invention further provides a liquid crystal composition which comprises as a first component a fluoro-substituted alkenyl compound represented by the formula (1), as other components a compound selected from the group consisting of the compounds represented by the formulas (7), (8) and (9), and a compound selected from the group consisting of the compounds represented by the formulas (10), (11) and (12).

The invention further provides a liquid crystal composition which comprises as a first component a fluoro-substituted alkenyl compound, as a second component a compound selected from the group consisting of the compounds represented by the formulas (2), (3) and (4), as a third component a compound selected from the group consisting of the compounds represented by the formulas (5) and (6), and as a fourth component a compound selected from the group consisting of the compounds represented by the formulas (10), (11) and (12).

Further, the present invention provides the liquid crystal compositions which further comprise at least one optically active compound.

Furthermore, the present invention provides a liquid crystal display element comprising the liquid crystal composition of the invention.

Now, the invention will be described in detail below with reference to the preferred modes of the invention.

The fluoroalkenyl compounds represented by the formula (1):

(1)

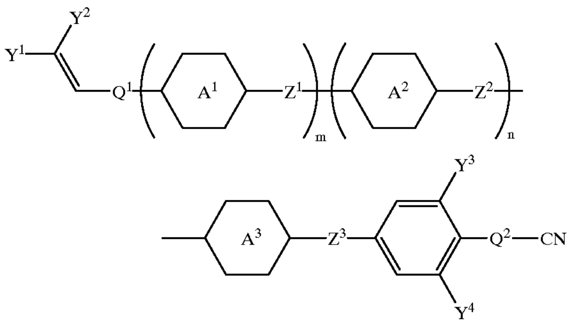

wherein the symbols are as defined above include compounds having 2 to 4 rings in the core and has no cyclohexane ring for Ring $A^3$ in the formula (1); compounds having a monofluoroalkenyl group or a difluoroalkenyl group when Ring $A^3$ is a cyclohexane ring and $Z^3$ is not a single bond and further having a cyano group; and compounds having a monofluoroalkneyl group or a difluoroalkenyl group when Ring $A^3$ is a cyclohexane ring and $Z^3$ is a single bond and further having a benzene ring with at least one H atom substituted by F, in addition to a cyano group.

The compounds represented by the formula (1) can show any $\Delta n$ depending on the combination of a ring structure and a substituent.

The compounds represented by the formula (1) with three or four rings have a broad liquid crystalline phase temperature range.

Accordingly, the compounds represented by the formula (1) can show a large $\Delta\epsilon$ and a large $K_{33}/K_{11}$ ratio owing to the above structure of the compounds.

In the compounds represented by the formula (1), any combination of $Y^1$ with $Y^2$ provides excellent physical properties of the compounds. Particularly, the compounds wherein $Y^1$ is a fluorine atom and $Y^2$ is a hydrogen atom have a high clearing point, and the compounds wherein both $Y^1$ and $Y^2$ are a fluorine atom show a low viscosity.

The compounds (1) wherein $Q^1$ is an alkylene group of 2–7 carbon atoms have a low viscosity and are preferable, and the compounds wherein $Q^1$ is the alkylene group having at least one —$CH_2$— substituted by —O— show an excellent compatibility with other liquid crystalline compounds or liquid crystal compositions.

The compounds (1) wherein $Q^2$ is a single bond have a high stability to light and the compounds wherein $Q^2$ is —C≡C— have a high clearing point and a low viscosity.

The compounds (1) wherein groups $Z^1$, $Z^2$ and $Z^3$ each are a single bond have a low viscosity and the compounds wherein groups $Z^1$, $Z^2$ and $Z^3$ each are —$CH_2CH_2$—, —$CH_2O$— or —$OCH_2$— have an excellent compatibility with other liquid crystalline compounds or liquid crystal compositions. Particularly, the compounds wherein groups $Z^1$, $Z^2$ and $Z^3$ each are —COO— or —$CF_2O$— show a large $\Delta\epsilon$ and the compounds wherein groups $Z^1$, $Z^2$ and $Z^3$ each are —CH═CH— or —C≡C— have a high clearing point and a low viscosity.

In the compounds represented by the formula (1), the core parts have various structures, which are illustrated in the compounds (1-1)–(1-7) below.

(1-1)

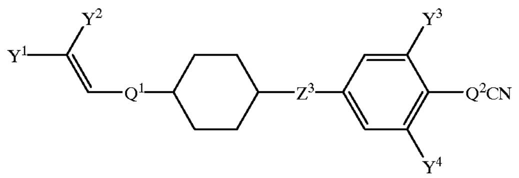

(1-2)

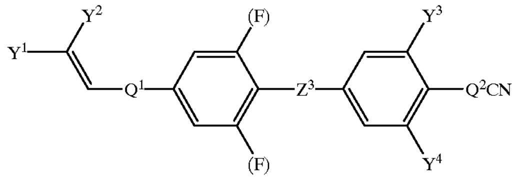

(1-3)

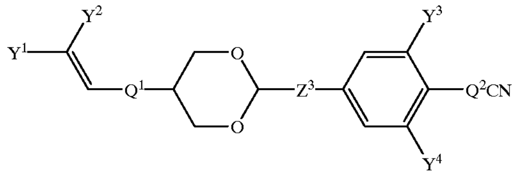

-continued (1-4)

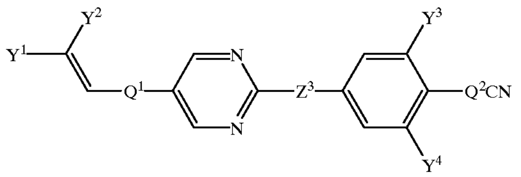

(1-5)

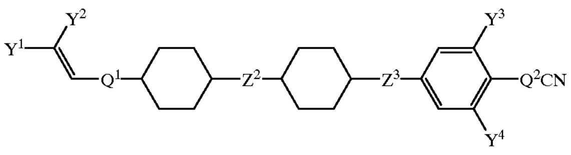

(1-6)

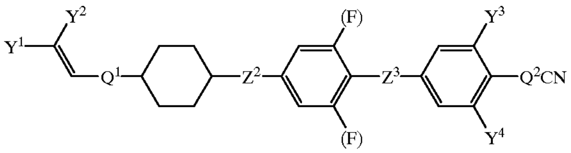

(1-7)

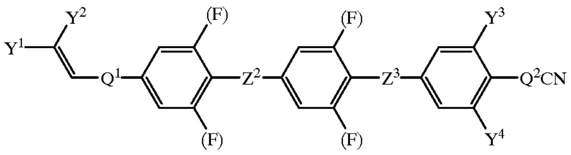

In the above formulas, $Y^1$, $Y^2$, $Y^3$, $Y^4$, $Q^1$, $Q^2$, $Z^2$ and $Z^3$ have the same meanings as defined above and each (F) is independently either F or H.

These compounds have a large $\Delta\epsilon$ and a large $K_{33}/K_{11}$ ratio.

Further characteristics of these compounds are mentioned below. The compounds (1-1) have a low viscosity, while the compounds (1-2) and (1-4) have a very large $\Delta\epsilon$, a large $\Delta n$ and a relatively low viscosity. The compounds (1-3) have a very large As, while the compounds (1-5)–(1-7) have a high clearing point. Further, $\Delta n$, $\Delta\epsilon$, and viscosity are increasingly larger or higher in the order of the compounds (1-5), (1-6) and (1-7).

The liquid crystal composition of the invention may comprise at least one liquid crystalline compound represented by the formula (1) as a first component. Preferably, the composition may comprise, in addition to the first component, at least one compound selected from the group consisting of the compounds represented by the formulas (2), (3) and (4) as a second component (hereinafter referred to as "Second component A") and/or at least one compound selected from the group consisting of the compounds represented by the formulas (5) and (6) (hereinafter referred to as "Second component B");

(2)

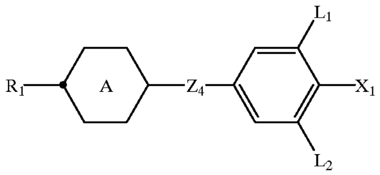

(3)

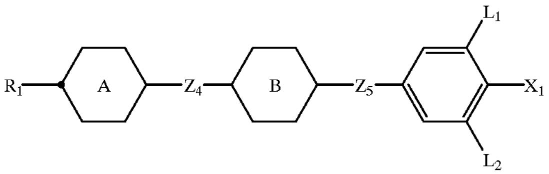

(4)

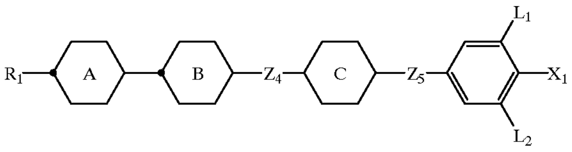

(5)

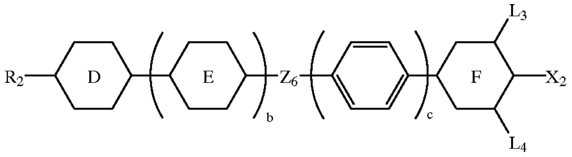

(6)

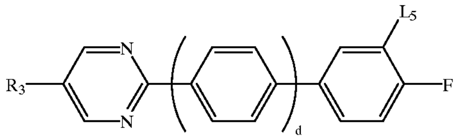

wherein the symbols are as defined above.

Further, the present composition may comprise as a third component at least one compound selected from the group consisting of the compounds represented by the formulas (10)–(12), which will be specifically illustrated later, in order to adjust threshold voltage (Vth), liquid crystal phase temperature range, optical anisotropy value, dielectric anisotropy value, viscosity and etc. Each of the components of the liquid crystal composition may be an analogue formed of respective isotopic elements because it has no significant difference in physical properties.

For the Second component A, preferred examples of the compound represented by the formula (2) include the following compounds (2-1)–(2-9); preferred examples of the compound represented by the formula (3) include the following compounds (3-1)–(3-97); and preferred examples of the compound represented by the formula (4) include the following compounds (4-1)–(4-33).

(2-1)

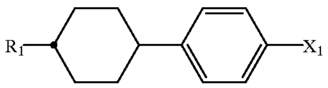

-continued (2-2)

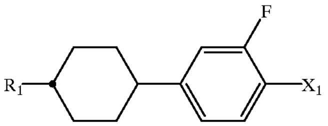

(2-3)

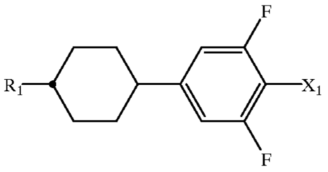

(2-4)

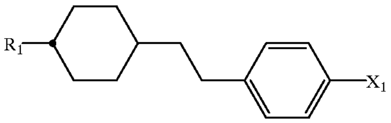

(2-5)

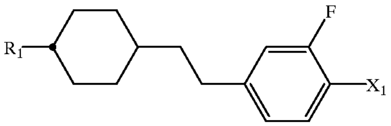

(2-6)

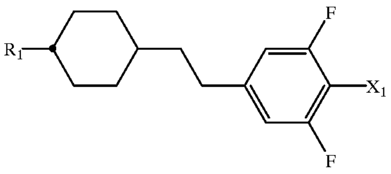

(2-7)

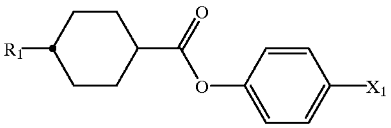

(2-8)

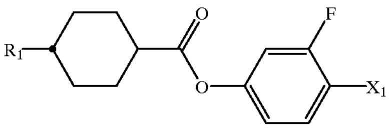

(2-9)

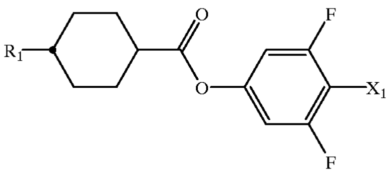

(3-1)

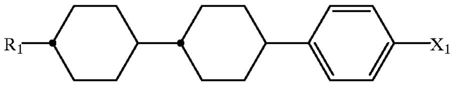

(3-2)

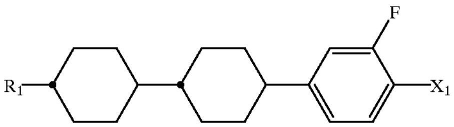

-continued
(3-3)
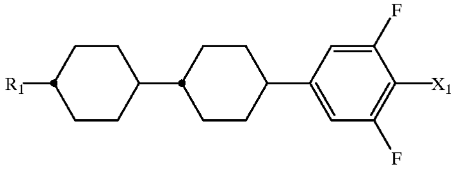
(3-4)
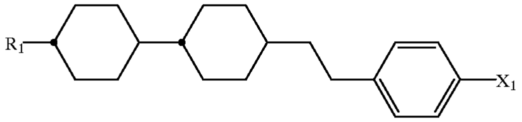
(3-5)
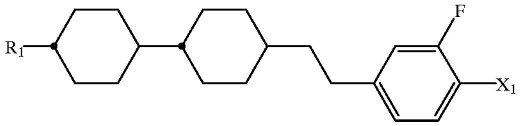
(3-6)
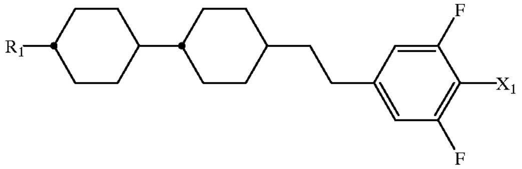
(3-7)
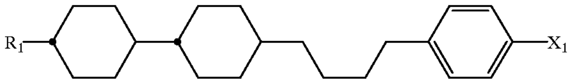
(3-8)
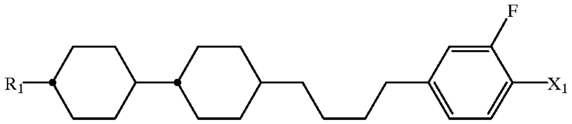
(3-9)
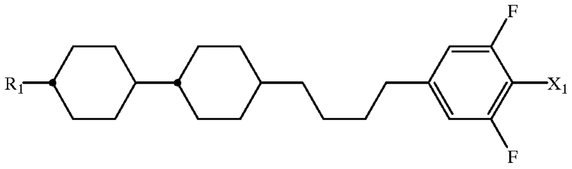
(3-10)
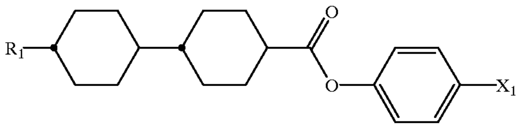
(3-11)
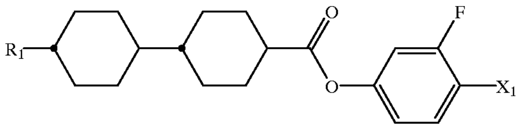
-continued
(3-12)
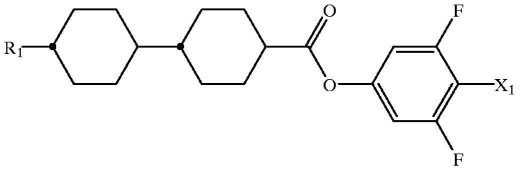
(3-13)
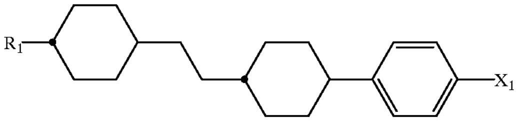
(3-14)
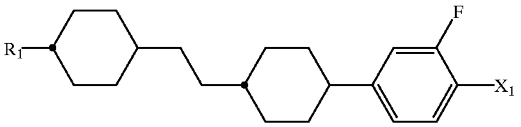
(3-15)
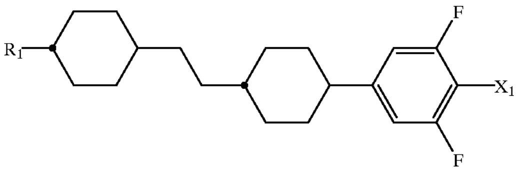
(3-16)
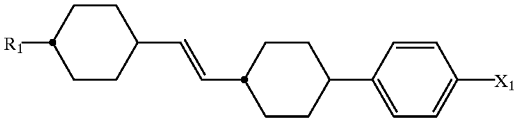
(3-17)
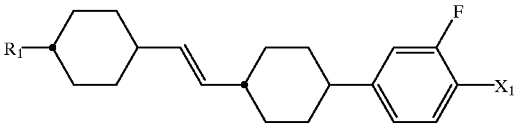
(3-18)
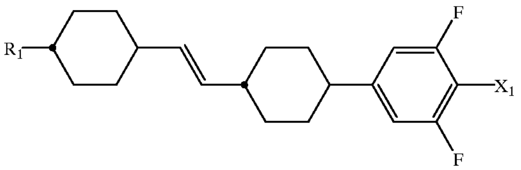
(3-19)
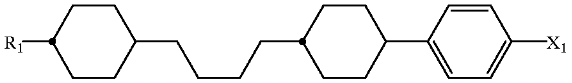
(3-20)
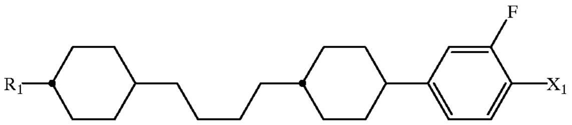

-continued
(3-21)
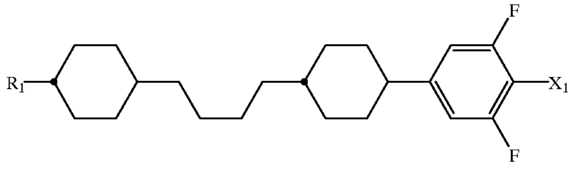
(3-22)
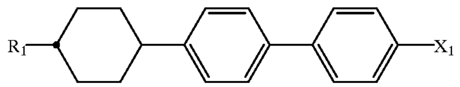
(3-23)
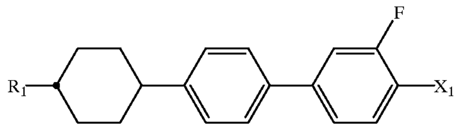
(3-24)
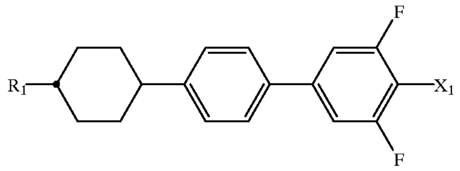
(3-25)
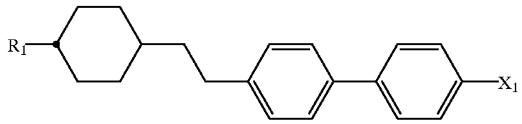
(3-26)
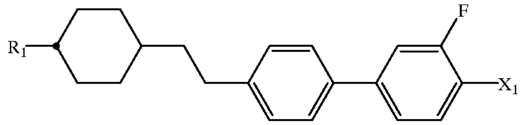
(3-27)
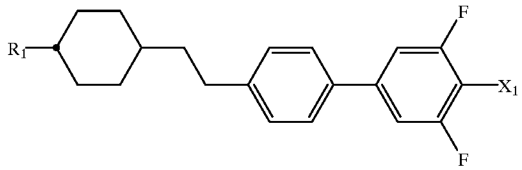
(3-28)
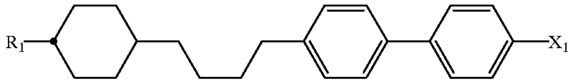
(3-29)
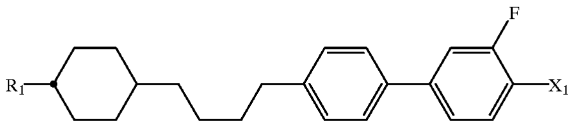
-continued
(3-30)
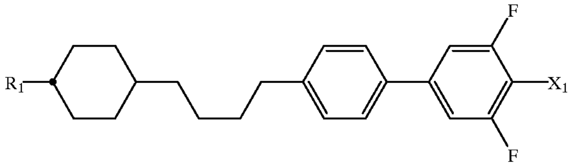
(3-31)
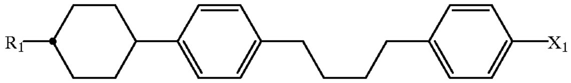
(3-32)
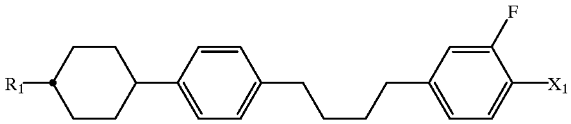
(3-33)
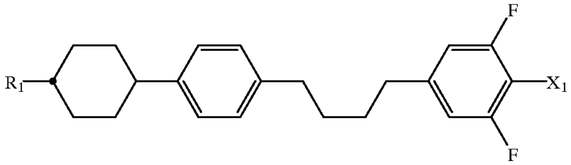
(3-34)
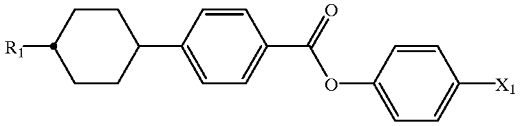
(3-35)
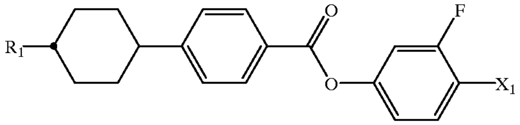
(3-36)
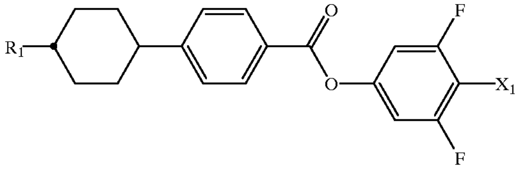
(3-37)
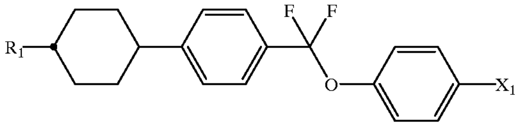
(3-38)
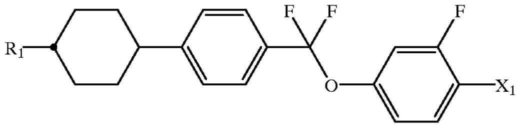

-continued
(3-39)
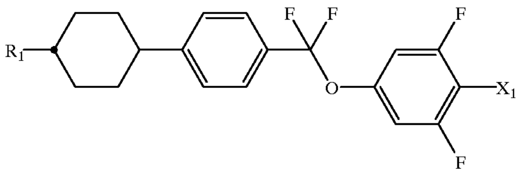
(3-40)
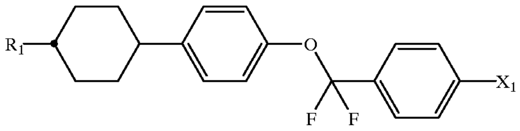
(3-41)
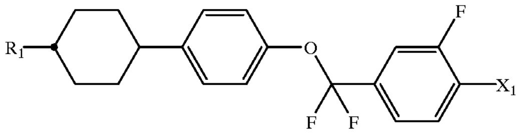
(3-42)
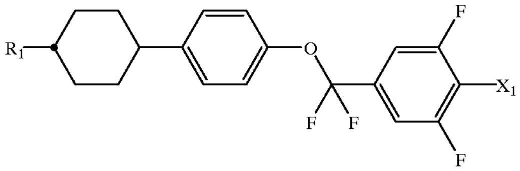
(3-43)
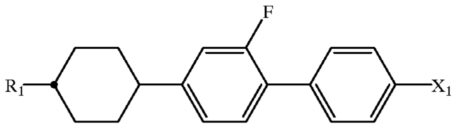
(3-44)
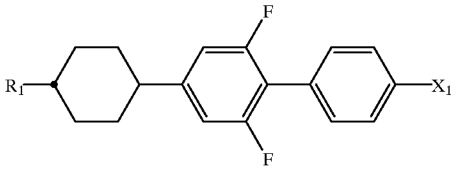
(3-45)
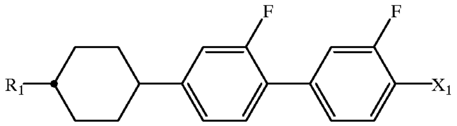
(3-46)
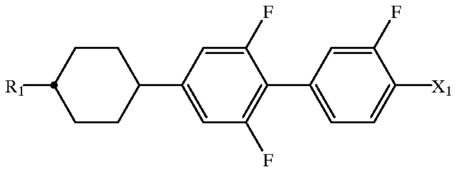
-continued
(3-47)
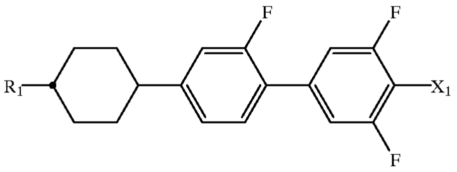
(3-48)
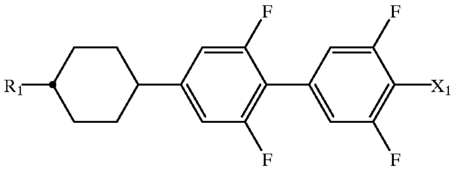
(3-49)
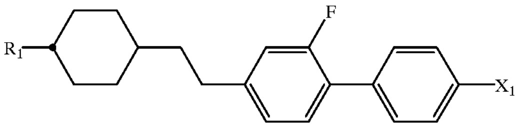
(3-50)
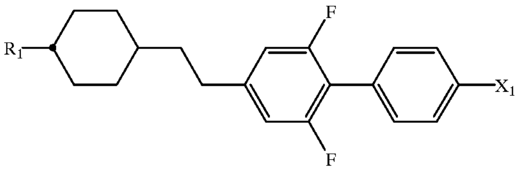
(3-51)
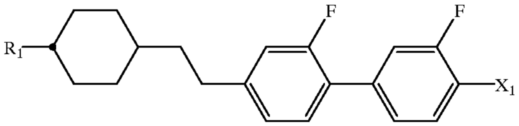
(3-52)
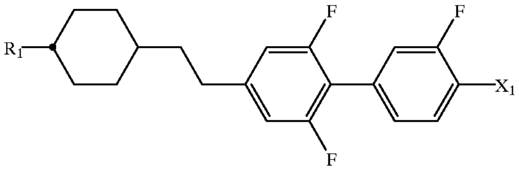
(3-53)
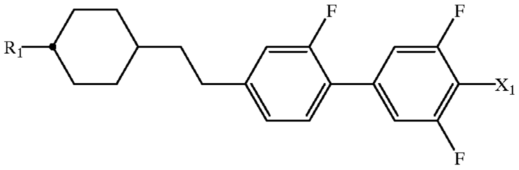
(3-54)
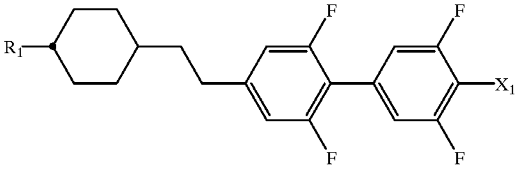

-continued
(3-55)
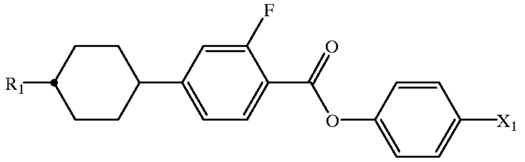
(3-56)
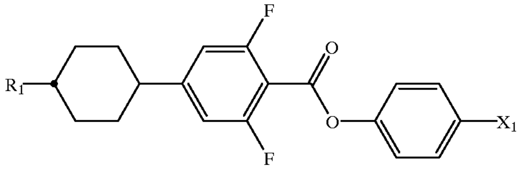
(3-57)
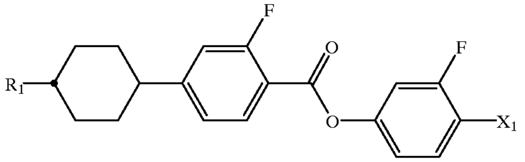
(3-58)
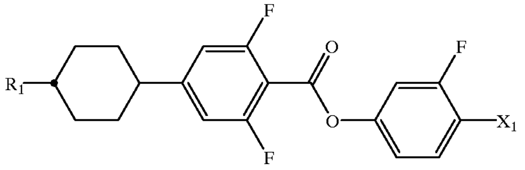
(3-59)
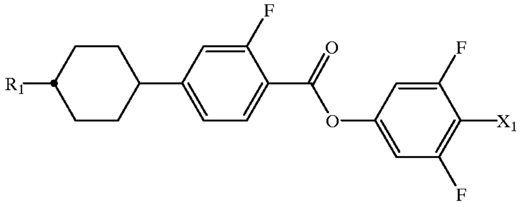
(3-60)
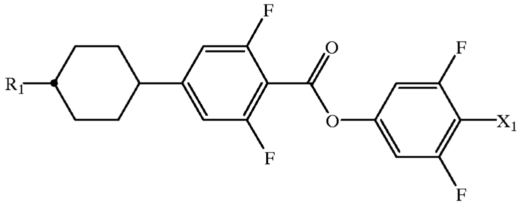
(3-61)
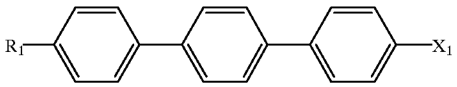
(3-62)
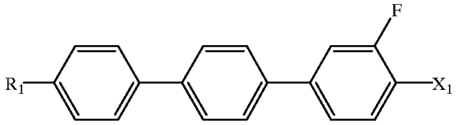
-continued
(3-63)
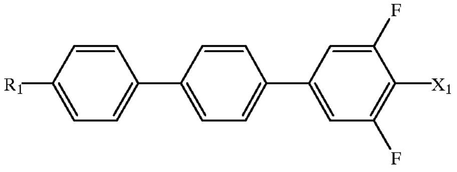
(3-64)
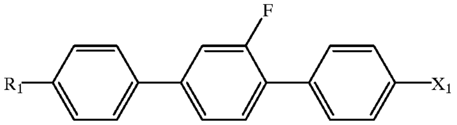
(3-65)
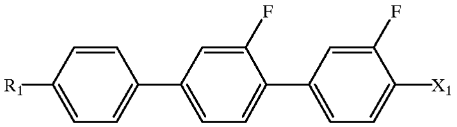
(3-66)
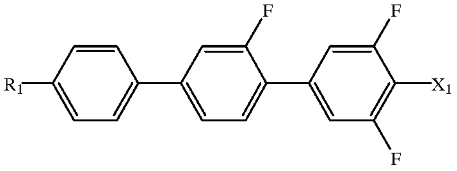
(3-67)
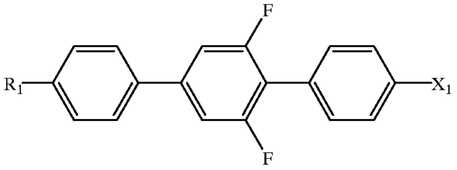
(3-68)
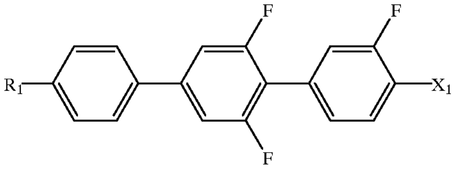
(3-68)
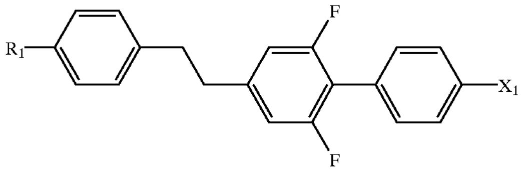
(3-70)
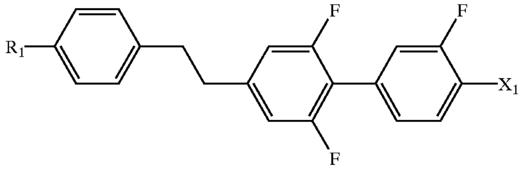

-continued
(3-71)
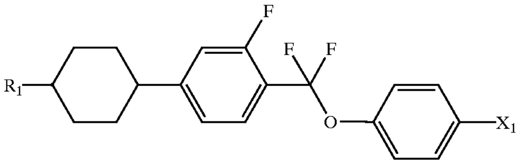
(3-72)
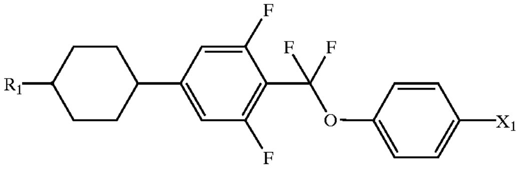
(3-73)
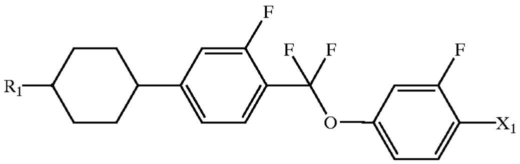
(3-74)
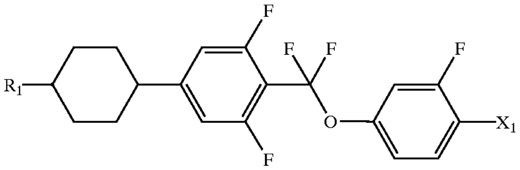
(3-75)
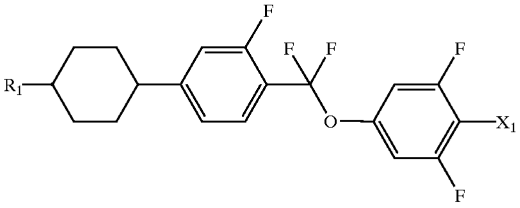
(3-76)
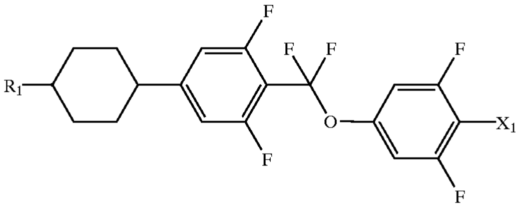
(3-77)
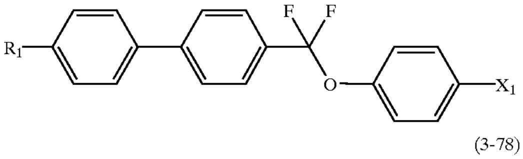
(3-78)
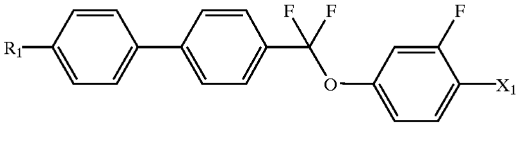
-continued
(3-79)
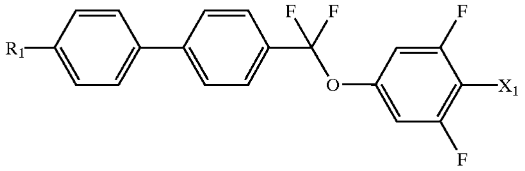
(3-80)
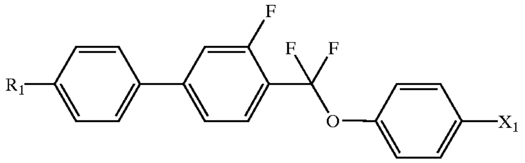
(3-81)
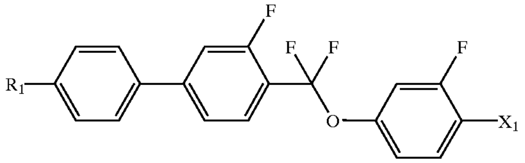
(3-82)
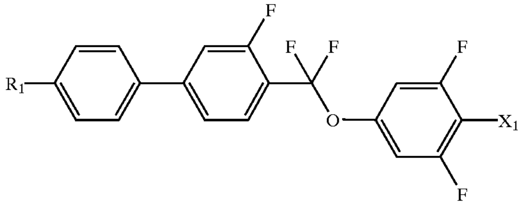
(3-83)
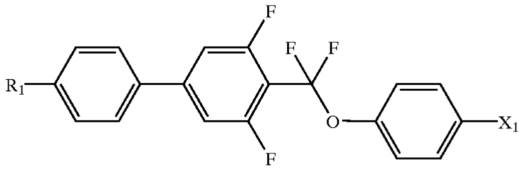
(3-84)
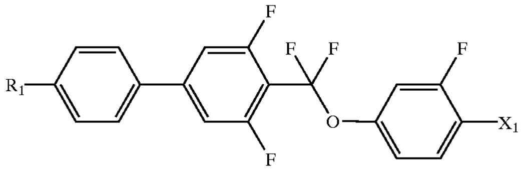
(3-85)
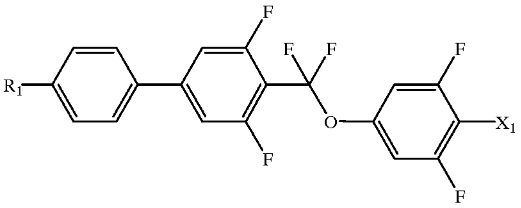

-continued
(3-86)
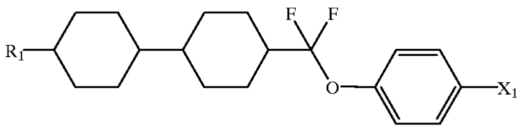
(3-87)
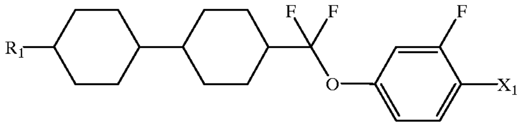
(3-88)
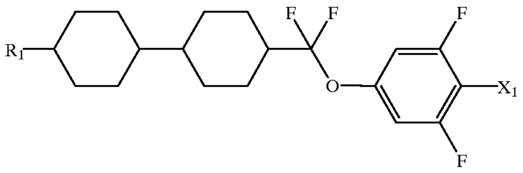
(3-89)
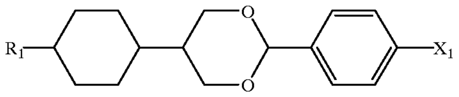
(3-90)
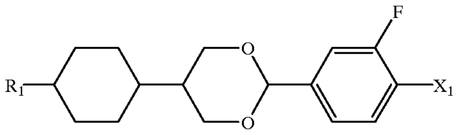
(3-91)
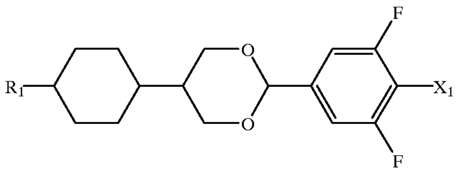
(3-92)
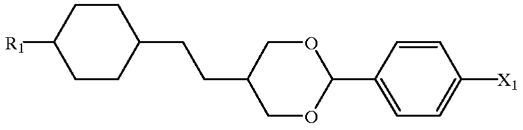
(3-93)
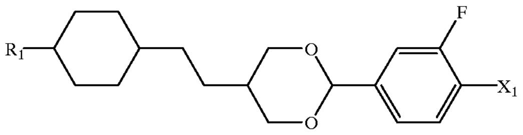
-continued
(3-94)
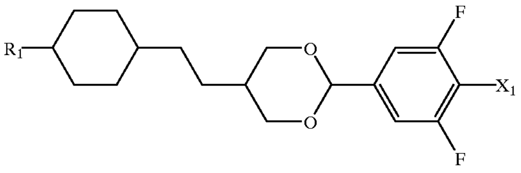
(3-95)
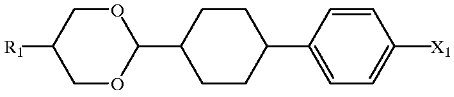
(3-96)
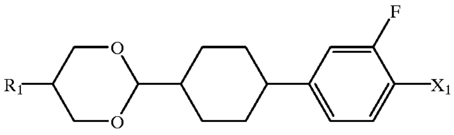
(3-97)
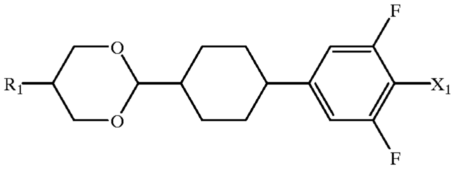
(4-1)
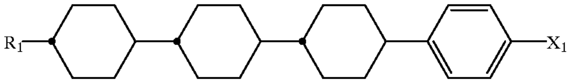
(4-2)
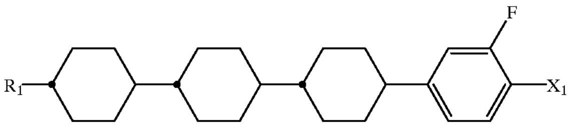
(4-3)
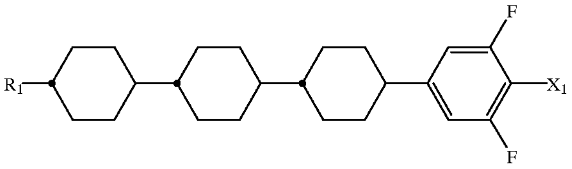
(4-4)
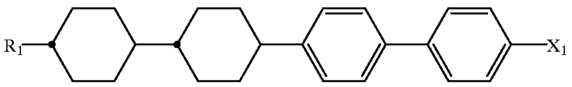
(4-5)
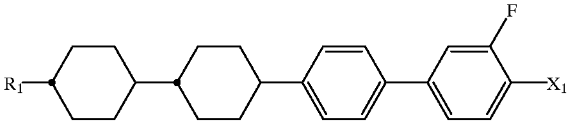

-continued
(4-6)
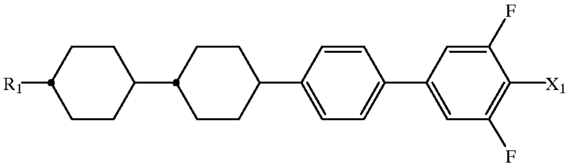
(4-7)
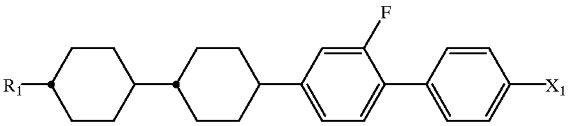
(4-8)
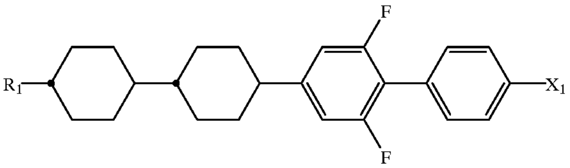
(4-9)
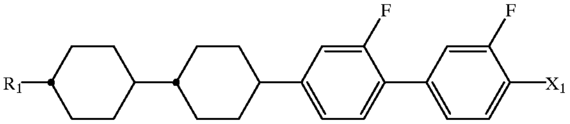
(4-10)
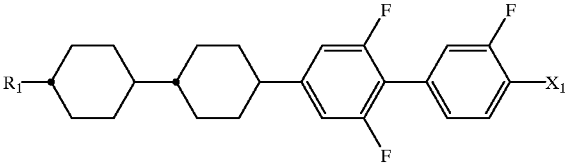
(4-11)
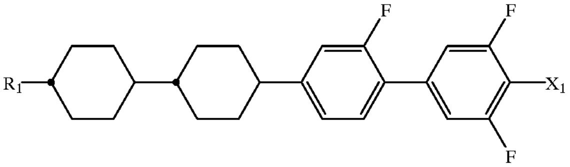
(4-12)
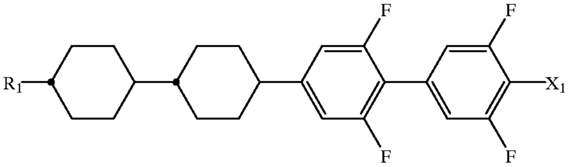
(4-13)
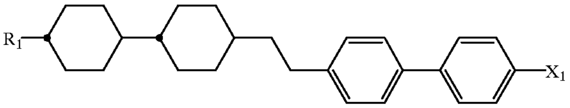
-continued
(4-14)
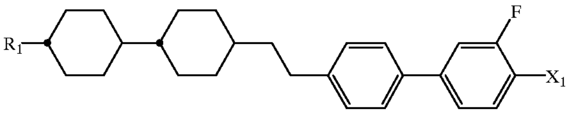
(4-15)
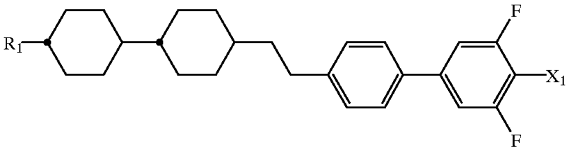
(4-16)
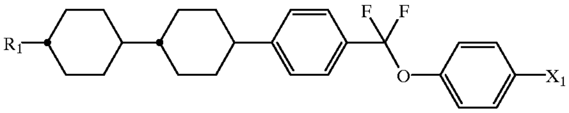
(4-17)
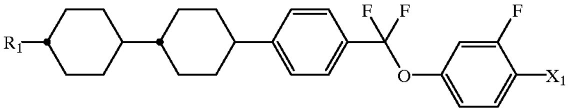
(4-18)
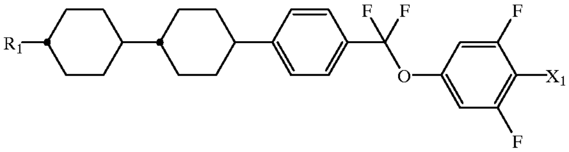
(4-19)
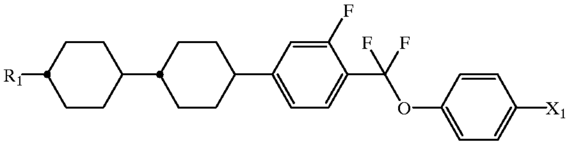
(4-20)
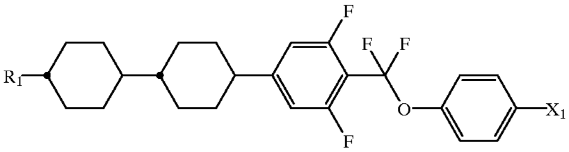
(4-21)
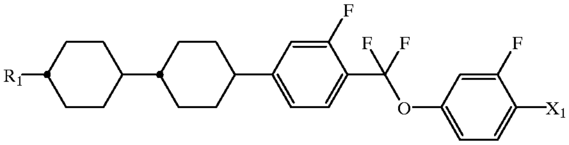
(4-22)
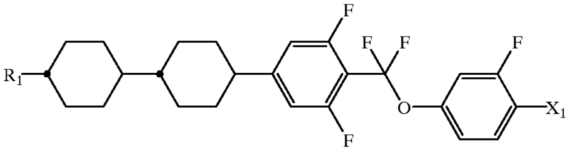

-continued (4-23)

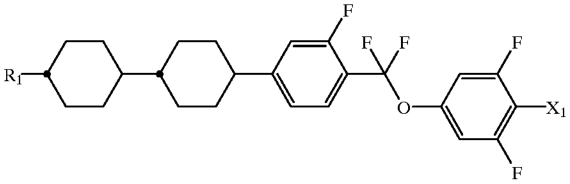

(4-24)

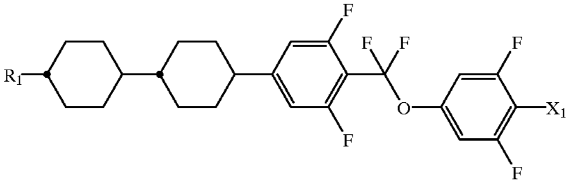

(4-25)

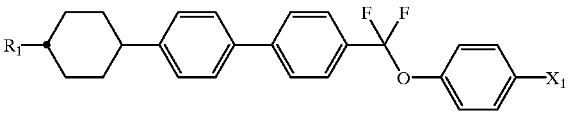

(4-26)

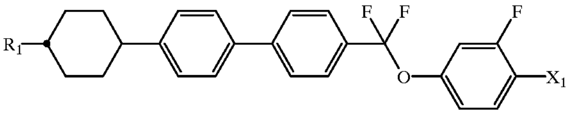

(4-27)

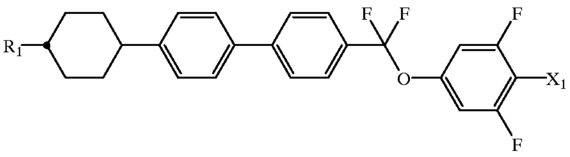

(4-28)

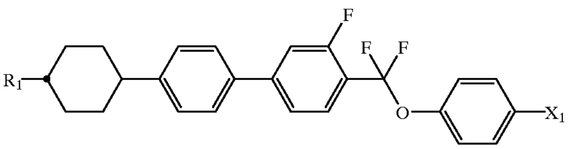

(4-29)

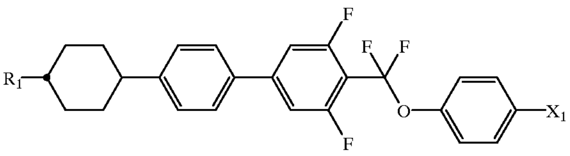

(4-30)

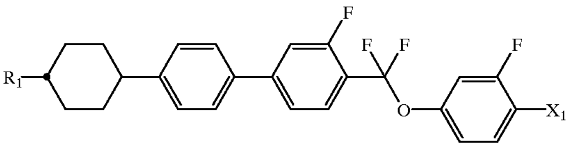

-continued (4-31)

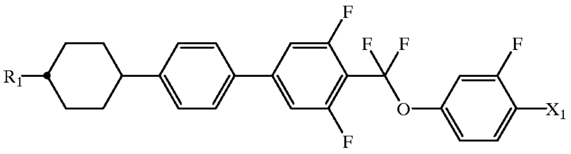

(4-32)

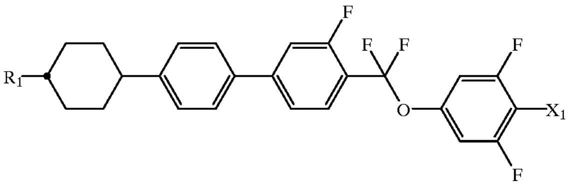

(4-33)

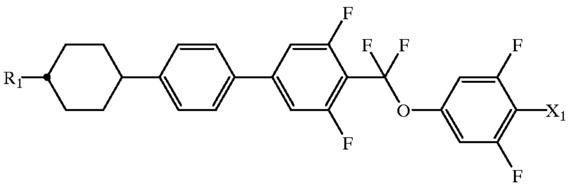

wherein $R_1$ and $X_1$ have the same meanings as defined above.

The compounds represented by the formulas (2)–(4) exhibit a positive dielectric anisotropy value and an excellent thermal stability and chemical stability. They are mainly used in the liquid crystal composition for the TFT mode. In the preparation of the liquid crystal composition for the TFT mode, the amount of the compound to be used is properly in the range of 1–99% by weight, preferably in the range of 10–97% by weight, and more preferably in the range of 40–95% by weight, based on the total weight of the composition.

Next, for the Second component B, preferred examples of the compounds represented by the formulas (5) and (6) include the following compounds (5-1)–(5-58) and (6-1)–(6-3), respectively.

(5-1)

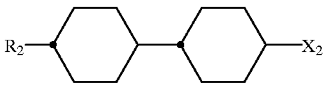

(5-2)

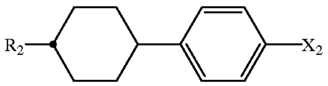

(5-3)

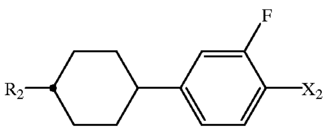

-continued
(5-4)
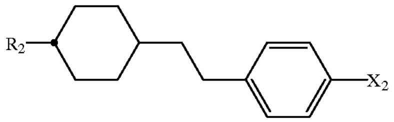
(5-5)
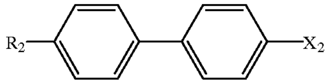
(5-6)
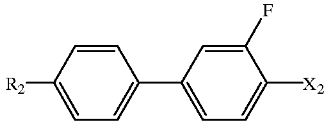
(5-7)
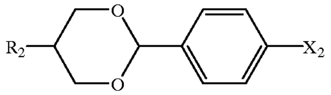
(5-8)
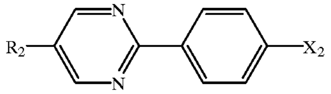
(5-9)
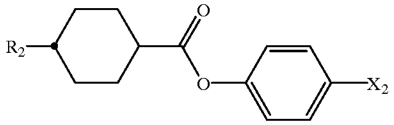
(5-10)
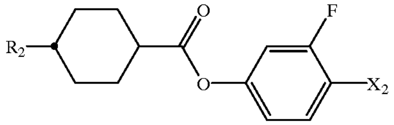
(5-11)
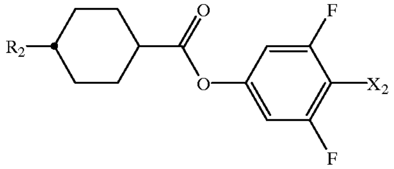
(5-12)
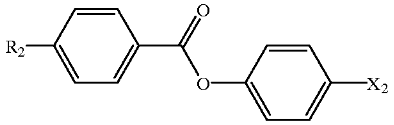
(5-13)
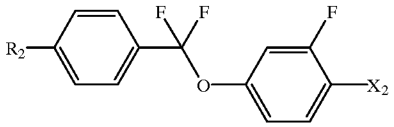
-continued
(5-14)
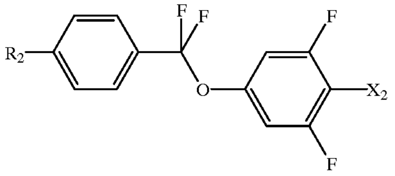
(5-15)
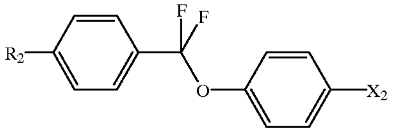
(5-16)
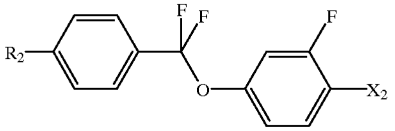
(5-17)
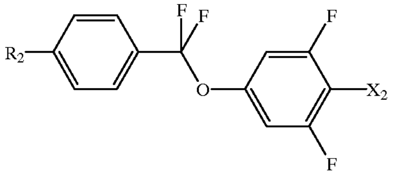
(5-18)
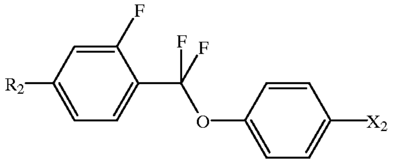
(5-19)
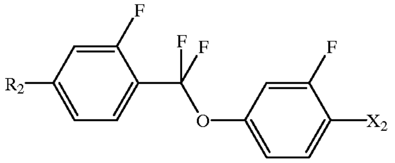
(5-20)
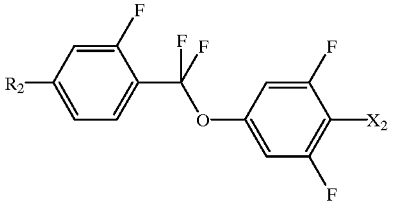
(5-21)
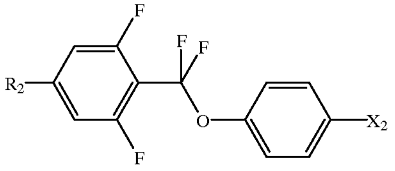

-continued
(5-22)
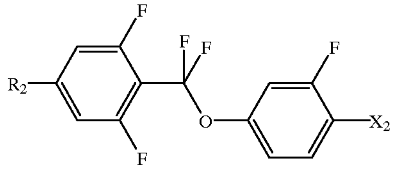
(5-23)
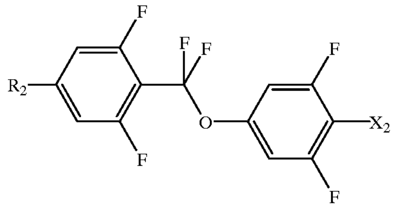
(5-24)
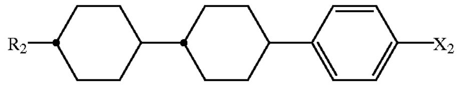
(5-25)
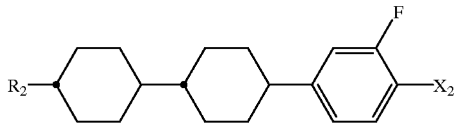
(5-26)
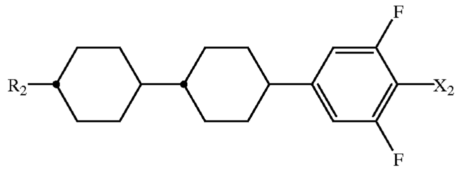
(5-27)
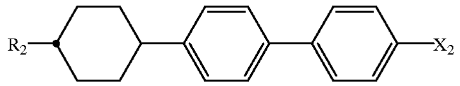
(5-28)
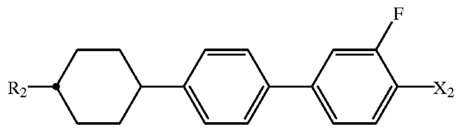
(5-29)
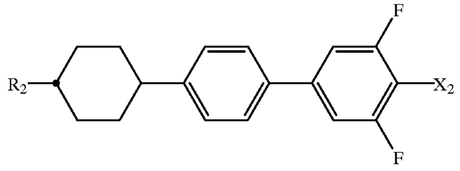
(5-30)
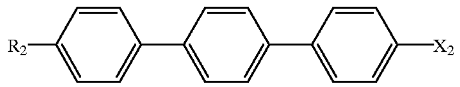
-continued
(5-31)
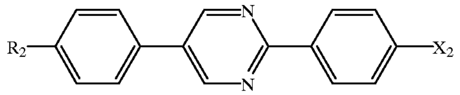
(5-32)
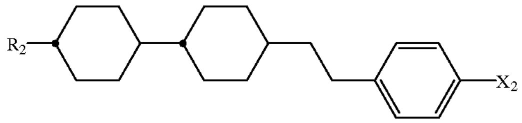
(5-33)
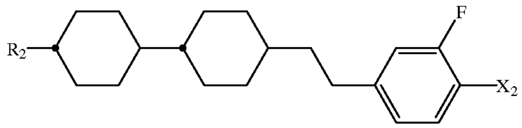
(5-34)
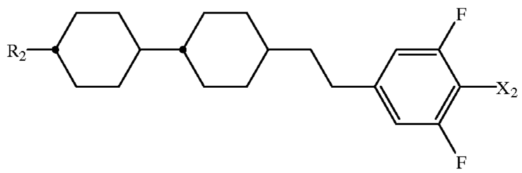
(5-35)
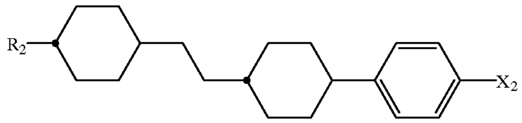
(5-36)
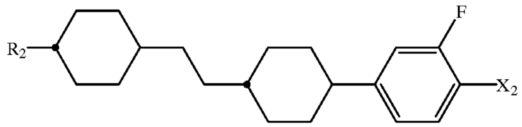
(5-37)
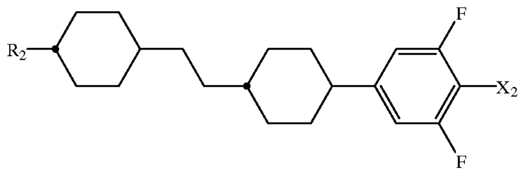
(5-38)
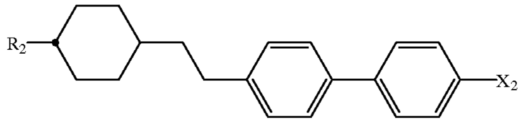
(5-39)
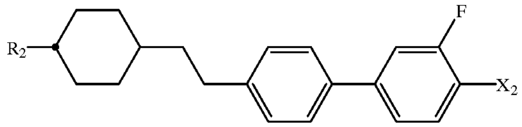

-continued
(5-40)
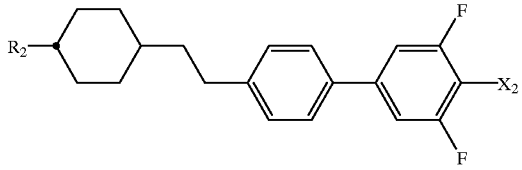
(5-41)
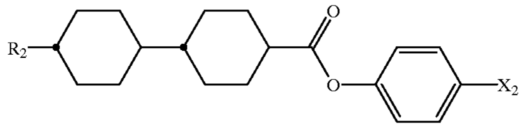
(5-42)
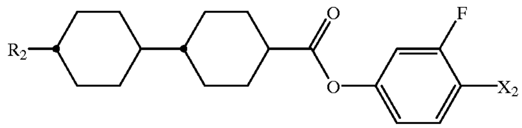
(5-43)
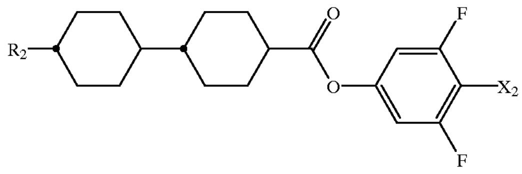
(5-44)
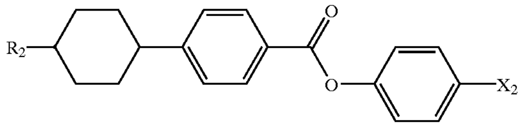
(5-45)
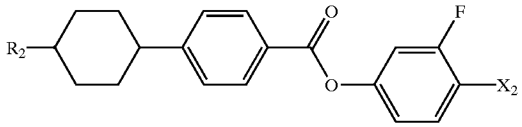
(5-46)
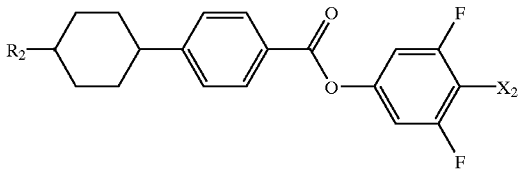
(5-47)
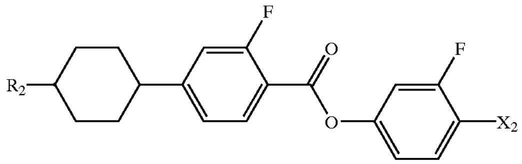
-continued
(5-48)
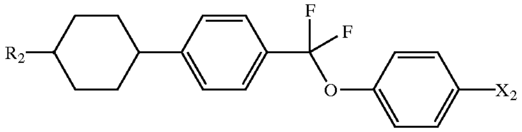
(5-49)
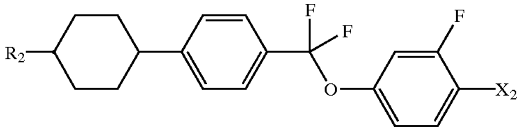
(5-50)
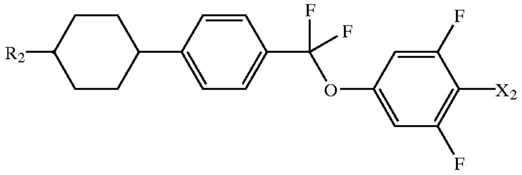
(5-51)
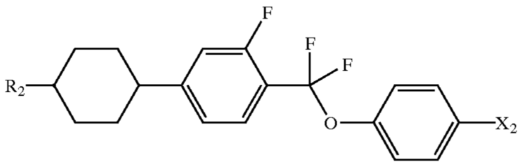
(5-52)
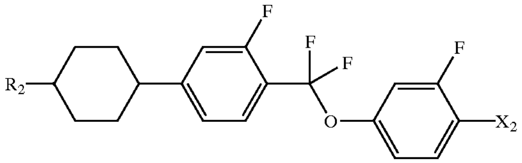
(5-53)
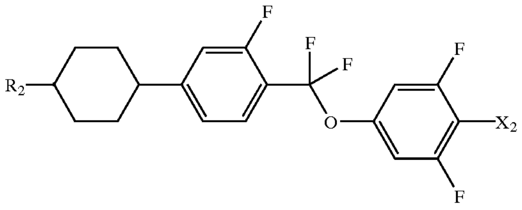
(5-54)
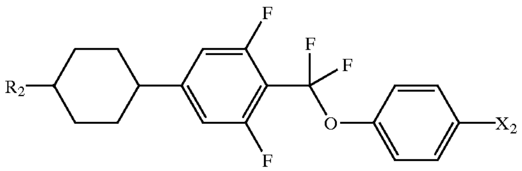
(5-55)
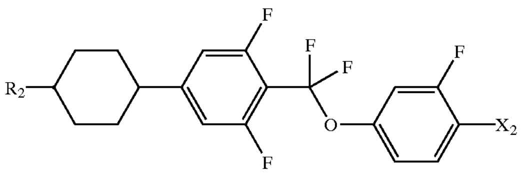

-continued (5-56)

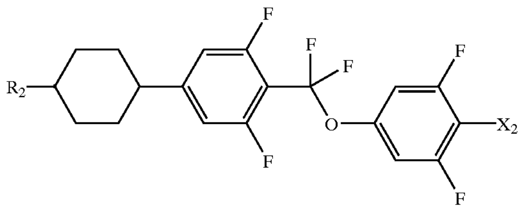

(5-57)

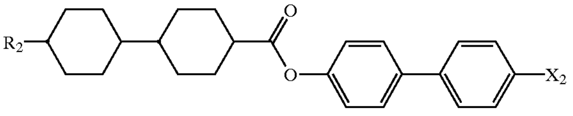

(5-58)

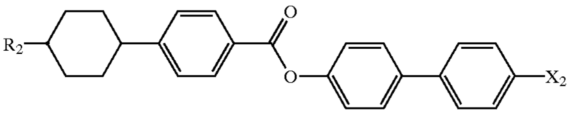

(6-1)

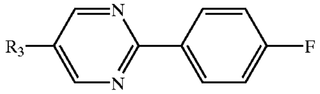

(6-2)

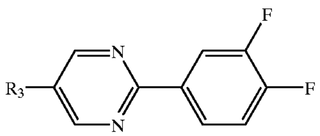

(6-3)

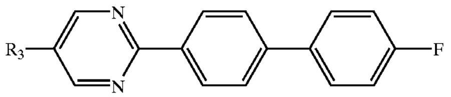

wherein $R_2$, $R_3$ and $X_2$ have the same meanings as defined above.

The compounds (5) and (6) exhibit a positive and large dielectric anisotropy value and thus are mainly used in the liquid crystal compositions for STN and TN. These compounds are used mainly for the purpose of lowering threshold voltage. They are also used for the purposes of adjusting viscosity and optical anisotropy value, broadening a liquid crystal phase temperature range and improving sharpness of the transmittance according to the electric field. In the preparation of liquid crystal compositions for STN or TN, the amounts of the compounds (5) and (6) to be used are properly in the range of 0.1–99.9% by weight, preferably in the range of 11–97% by weight, and more preferably in the range of 41–95% by weight.

In the preparation of liquid crystal compositions having a negative dielectric anisotropy value which are used for the vertical aligning mode (VA mode), it is advantageous to incorporate therein at least one compound selected from the group consisting of the compounds (7)–(9) (hereinafter called Second component C), in addition to at least one compound represented by the formula (1).

(7)

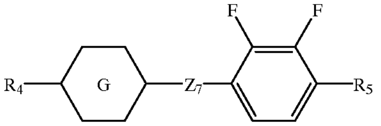

(8)

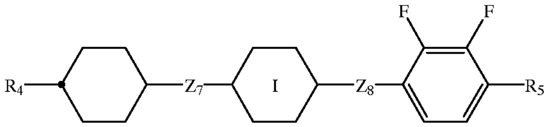

(9)

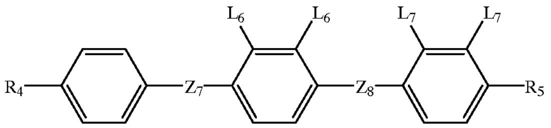

wherein $R_4$, $R_5$, Rings G and I, $L_6$, $L_7$, $Z_7$ and $Z_8$ are as defined above.

When these compounds (7)–(9) are used in the liquid crystal compositions, at least one compound selected from the group consisting of the below illustrated compounds (10)–(12) may be incorporated therein in order to adjust threshold voltage, liquid crystal phase temperature range, optical anisotropy value, dielectric anisotropy value, viscosity and etc.

Preferred examples of the compounds represented by the formulas (7), (8) and (9) include the compounds (7-1)–(7-3), the compounds (8-1)–(8-5) and the compounds (9-1)–(9-3), respectively.

(7-1)

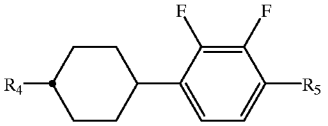

(7-2)

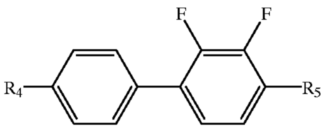

(7-3)

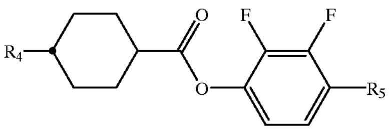

(8-1)

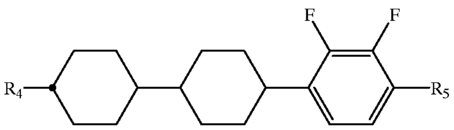

-continued (8-2)

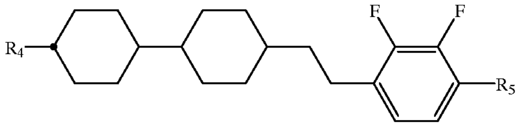

(8-3)

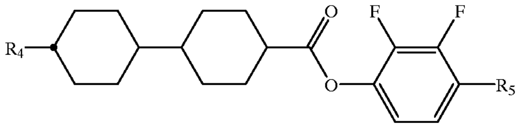

(8-4)

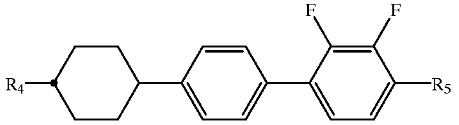

(8-5)

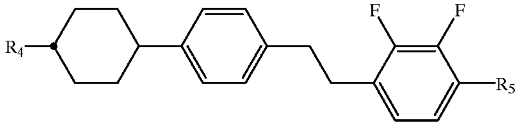

(9-1)

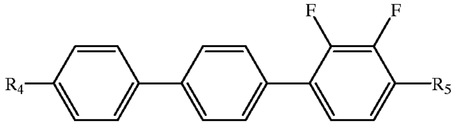

(9-2)

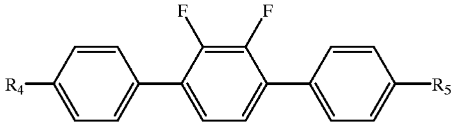

(9-3)

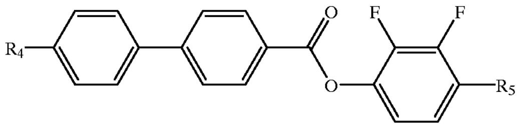

wherein $R_4$ and $R_5$ have the same meanings as defined above.

The compounds represented by the formulas (7)–(9) have a negative dielectric anisotropy value. The compounds represented by the formula (7) are a bicyclic compound and they are mainly used for the purpose of adjusting threshold voltage, viscosity or optical anisotropy value. The compounds represented by the formula (8) are used for the purposes of widening the nematic ranges for example by heightening clearing points, as well as decreasing the threshold voltage and increasing the optical anisotropy value.

The compounds represented by the formulas (7)–(9) are mainly used in the liquid crystal composition for VA having negative dielectric anisotropy value. When these compounds are used in an increased amount, the resulting composition shows decreased threshold voltage and increased viscosity. So long as the required threshold voltage is satisfied, the compounds are preferably used in the smallest possible amounts. Since the absolute value of dielectric anisotropy are not more than 5, when the compounds are used in an amount less than 40% by weight, the produced elements may not be effectively driven. The amount of the compounds represented by the formulas (7)–(9) used in preparing the liquid crystal composition for VA is preferably not less than 40% by weight and suitably in the range of 51–95% by weight.

The compounds represented by the formulas (7)–(9) may optionally be incorporated in the composition having a positive dielectric anisotropy value for the purposes of controlling the elastic constant and regulating the curves of voltage transmittance. For example, the compounds represented by the formulas (7)–(9) may be added as a second component C to the composition containing the compound represented by the formula (1) as the first component and the second component A and/or the second component B mentioned above. The amount of the compounds (7)–(9) to be added in this case are preferably not more than 30% by weight.

The compounds represented by the formulas (10)–(12) may be incorporated in the composition as the third component.

(10)

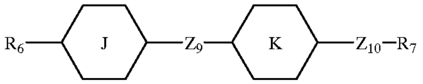

(11)

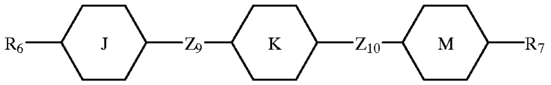

(12)

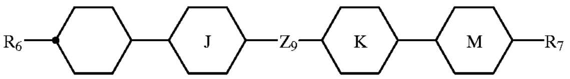

wherein $R_6$, $R_7$, Rings J, K and M, $Z_9$ and $Z_{10}$ are as defined above.

Preferred examples of the compounds represented by the formulas (10), (11) and (12) as the third component of the present liquid crystal composition include the compounds (10-1)–(10-11), the compounds (11-1)–(11-12) and the compounds (12-1)–(12-6), respectively.

(10-1)

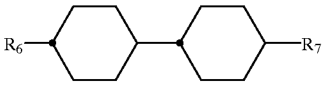

(10-2)

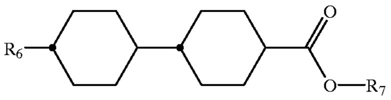

(10-3)

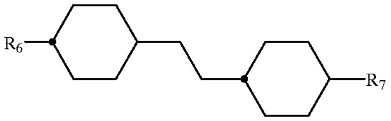

-continued
(10-4)
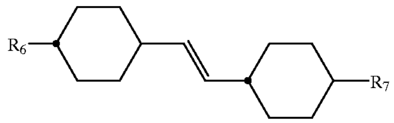
(10-5)
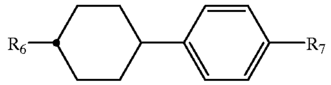
(10-6)
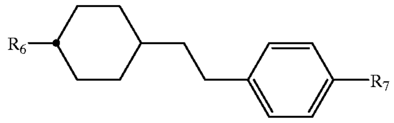
(10-7)
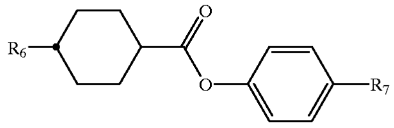
(10-8)
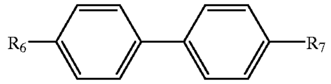
(10-9)
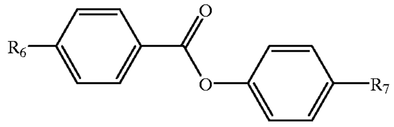
(10-10)
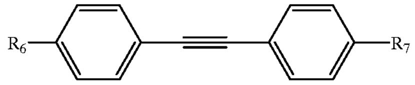
(10-11)
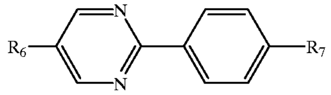
(11-1)
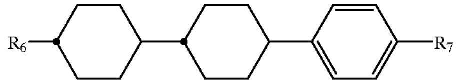
(11-2)
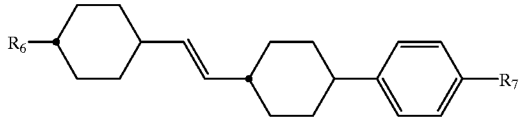
(11-3)
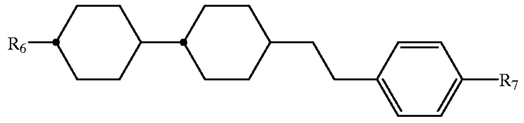
-continued
(11-4)
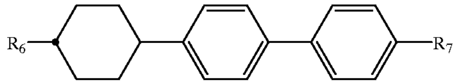
(11-5)
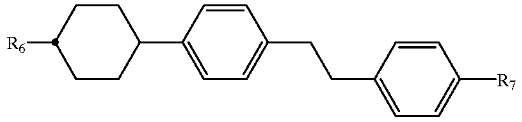
(11-6)
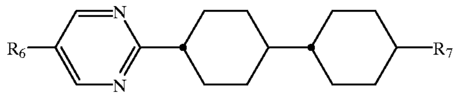
(11-7)
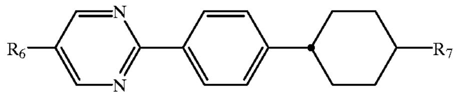
(11-8)
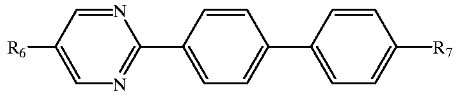
(11-9)
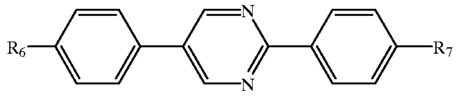
(11-10)
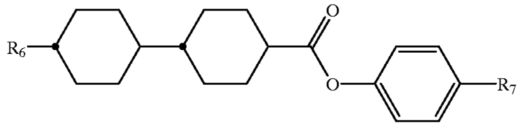
(11-11)
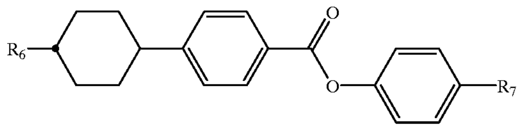
(11-12)
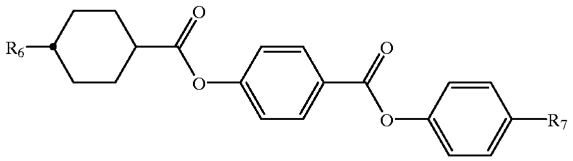
(12-1)
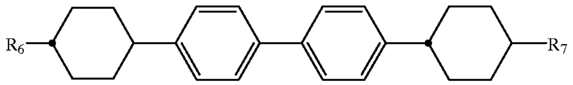

-continued (12-2)

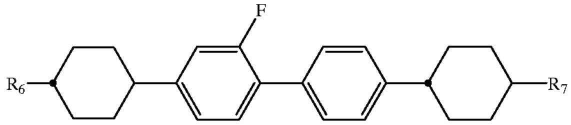

(12-3)

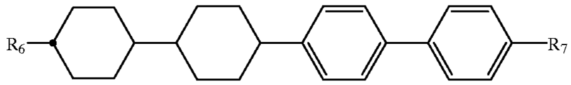

(12-4)

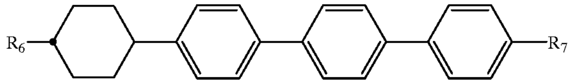

(12-5)

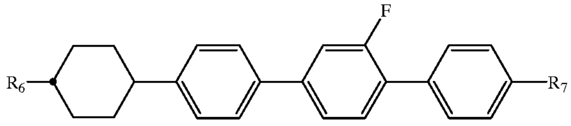

(12-6)

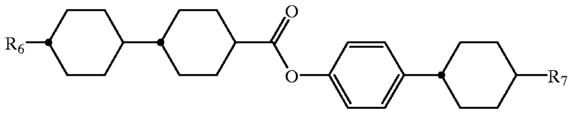

wherein $R_6$ and $R_7$ have the same meanings as defined above.

The compounds represented by the formulas (10)–(12) have a small absolute value of dielectric anisotropy. The compounds represented by the formula (10) are mainly used for the purpose of adjusting viscosity or optical anisotropy value. The compounds represented by the formulas (11) and (12) are used for the purpose of widening the nematic phase temperature range by heightening clearing points or adjusting the optical anisotropy value.

When the compounds (10)–(12) are used in an increased amount, the resulting composition shows increased threshold voltage and decreased viscosity. So long as the required threshold voltage is satisfied, these compounds are desirably used in the largest possible amounts. In the preparation of the liquid crystal composition for TFT, the amount of the compounds represented by the formulas (10)–(12) to be used is preferably not more than 40% by weight, more preferably not more than 35% by weight. In the preparation of the liquid crystal composition for STN or TN, the amount of the compounds (10)–(12) is preferably not more than 70% by weight, more preferably not more than 60% by weight.

The liquid crystal compositions of the invention preferably comprise at least one liquid crystalline compound represented by the formula (1) in the range of 0.1–99% by weight so as to provide excellent physical properties. The liquid crystal compositions are generally prepared by any of the methods known per se such as, for example, the method wherein various components are mutually dissolved at an elevated temperature. Addition of appropriate additives, if necessary, makes the liquid crystal composition improved and optimized for the intended uses. Such additives are well known to any person of ordinary skill in the art and are described in detail in the literatures. Generally added is a chiral doping agent, which is effective in inducing a liquid crystal to form a helical structure and consequently adjusting a twist angle as required and preventing an inverse twist. Examples of the chiral doping agent include the optically active compounds represented by the following formulas (OP-1) to (OP-8). is adjusted preferably in the range of 40–200 μm. In case of the compositions for STN, the adjustment is preferably in the range of 6–20 μm. In case of those for bistable TN mode, the adjustment is preferably in the range of 1.5–4 μm. Further, two or more of the optically active compounds may be added to adjust the temperature dependence of pitch.

The addition of dichroic dyes of merocyanine, styryl, azo, azomethine, azoxy, quinophthalone, anthraquinone and tetrazine types enables the liquid crystal composition to be used for GH. The composition of the invention are usable as the liquid crystal composition for electrically controlled birefringence (ECB) mode or DS mode as well as for NCAP manufactured by microcapsulating the nematic liquid crystal and the polymer dispersion type liquid crystal device (PDLCD) manufactured by forming a three-dimensional reticular macromolecule in a liquid crystal such as, for example, the polymer network liquid crystal device (PNLCD).

Examples of the nematic liquid crystal composition of the invention manufactured as described above include the following compositions 1–38. The compounds used in these compositions are expressed by the symbols shown in Table 1 below. The parenthesized numbers next to the compounds in the composition examples are identical with those shown in the working examples below. The content of the compound is in terms of "% by weight" unless otherwise specified. The physical property data of the compositions are expressed by $T_{NI}$ (nematic-isotropic liquid phase transition temperature), $\eta$ (viscosity: measured at 20.0° C.), An (optical anisotropy value: measured at 25.0° C.), $\Delta\epsilon$ (dielectric anisotropy value: measured at 25° C.), and $V_{TH}$ (threshold voltage: measured at 25.0° C.).

(OP-1)

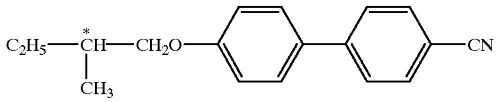

(OP-2)

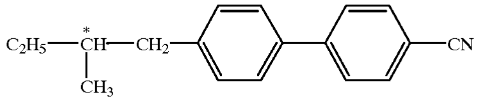

(OP-3)

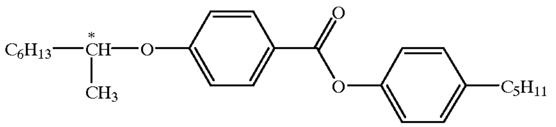

(OP-4)

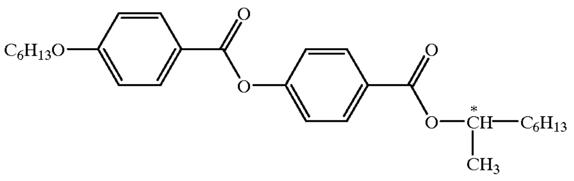

-continued (OP-5)

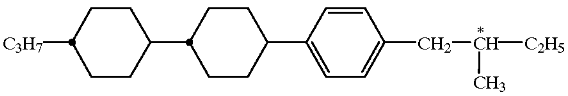

(OP-6)

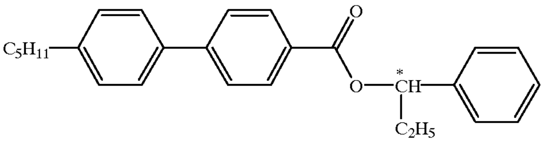

(OP-7)

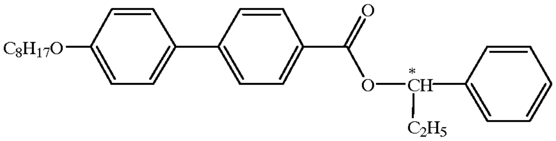

-continued (OP-8)

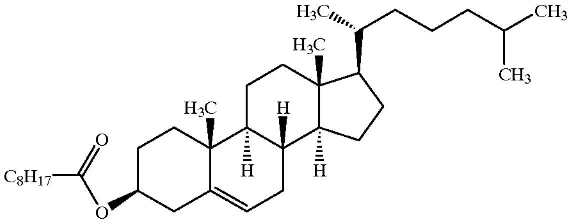

The liquid crystal compositions of the invention generally rely on the addition of such an optically active compound to adjust the pitch of twist. In case of the liquid crystal composition for TFT or TN, the pitch of twist

TABLE 1

Representation of compounds by the symbols
$R-(A_1)-Z_1-\ldots-Z_n-(A_n)-X$

| 1) Left terminal group R- | Symbol | 3) Bond group $-Z_1-$, $-Z_n-$ | Symbol |
|---|---|---|---|
| $C_nH_{2n+1}$— | n- | —$C_2H_4$— | 2 |
| $C_nH_{2n+1}O$— | nO- | —$C_4H_8$— | 4 |
| $C_nH_{2n+1}OC_mH_{2m}$— | nOm- | —COO— | E |
| $CH_2$=CH— | V- | —C≡C— | T |
| $CH_2$=CH—$C_nH_{2n}$— | Vn- | —CH=CH— | V |
| $C_nH_{n+1}CH$=$CHC_mH_{2m}$— | nVm- | —$CF_2O$— | CF2O |
| $C_nH_{2n+1}CH$=$CHC_mH_{2m}CH$=$CHC_kH_{2k}$— | nVmVk- | —$OCF_2$— | OCF2 |
| $CF_2$=CH— | VFF- | | |
| $CF_2$=$CHC_nH_{2n}$— | VFFn- | | |
| **2) Ring structure $-(A_1)-$, $-(A_n)-$** | **Symbol** | **4) Right terminal group -X** | **Symbol** |
| 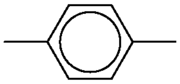 | B | —F | —F |
| 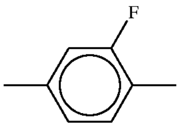 | B(F) | —Cl<br>—CN | —CL<br>—C |
| 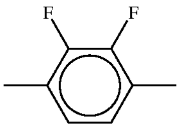 | B(2F,3F) | —$CF_3$<br>—$OCF_3$ | —CF3<br>—OCF3 |
| 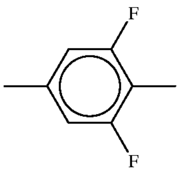 | B(F,F) | —$OCF_2H$<br>—$C_nH_{2n+1}$ | —OCF2H<br>-n |
| | | —$OC_nH_{2n+1}$ | -On |

TABLE 1-continued

| Representation of compounds by the symbols R-$(A_1)$-$Z_1$- . . . -$Z_n$-$(A_n)$-X | | | |
|---|---|---|---|
| 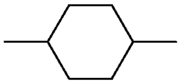 | H | $-COOCH_3$<br>$-C_nH_{2n}CH{=}CH_2$ | -EMe<br>-nV |
| 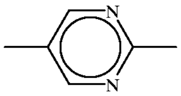 | Py | $-C_mH_{2m}CH{=}CHC_nH_{2n+1}$<br>$-C_mH_{2m}CH{=}CHC_nH_{2n}F$ | -mVn<br>-mVnF |
| 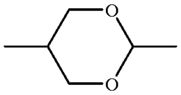 | G | $-CH{=}CF_2$<br>$-C_nH_{2n}CH{=}CF_2$ | -VFF<br>-nVFF |
| 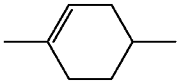 | Ch | $-C{\equiv}C-CN$ | -TC |

Examples of Representation

Ex. 1 3-H2B(F,F)B(F)-F

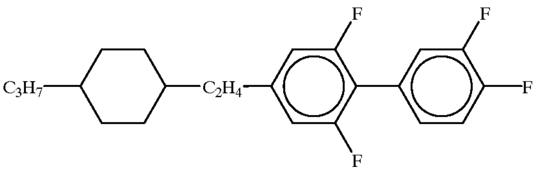

Ex. 3 1V2-BEB(F,F)-C

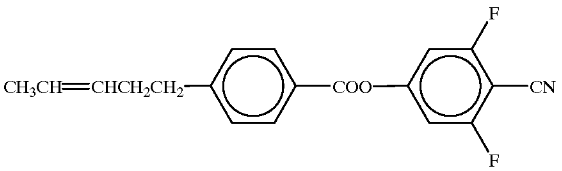

Ex. 2 3-HB(F)TB-2

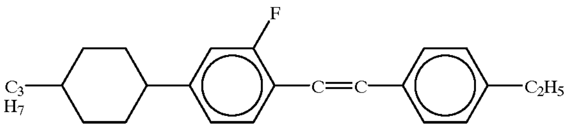

Composition Example 1

| | |
|---|---|
| VFF2-B(F,F)B-C (No. 7) | 5.0% |
| VFF2-B(F,F)B(F)-C (No. 8) | 5.0% |
| VFF-B(F,F)B-C (No. 1) | 5.0% |
| 1V2-BEB(F,F)-C | 5.0% |
| 3-HB-C | 10.0% |
| 1-BTB-3 | 5.0% |
| 2-BTB-1 | 10.0% |
| 3-HH-4 | 11.0% |
| 3-HHB-1 | 11.0% |
| 3-HHB-3 | 9.0% |
| 3-H2BTB-2 | 4.0% |
| 3-H2BTB-3 | 4.0% |
| 3-H2BTB-4 | 4.0% |
| 3-HB(F)TB-2 | 6.0% |
| 3-HB(F)TB-3 | 6.0% |

The physical properties of this composition are shown below.

$T_{NI}$=79.5 (° C.)

$\eta$=20.9 (mPa·s)

$\Delta n$=0.164

$\Delta\epsilon$=9.2

$V_{TH}$=1.60 (V)

0.8 Part by weight of the optically active compound represented by the formula (OP-4) was added to 100 parts by weight of this composition, and the resulting composition showed a pitch of 11.2 $\mu$m.

Composition Example 2

| | |
|---|---|
| VFF-B(F)B(F,F)-C (No. 9) | 5.0% |
| 3O1-BEB(F)-C | 15.0% |
| 4O1-BEB(F)-C | 13.0% |
| 5O1-BEB(F)-C | 13.0% |
| 2-HHB(F)-C | 15.0% |
| 3-HHB(F)-C | 15.0% |
| 3-HB(F)TB-2 | 4.0% |
| 3-HB(F)TB-3 | 4.0% |
| 3-HB(F)TB-4 | 4.0% |
| 3-HHB-1 | 8.0% |
| 3-HHB-O1 | 4.0% |

The physical properties of this composition are shown below.

$T_{NI}$=89.1 (° C.)

$\eta$=86.6 (mPa·s)

Δn =0.149

Δ∈=30.5

$V_{TH}$=0.92 (V)

Composition Example 3

| | |
|---|---|
| VFF-GB(F,F)-C (No. 29) | 4.0% |
| 5-PyB-F | 4.0% |
| 3-PyB(F)-F | 4.0% |
| 2-BB-C | 5.0% |
| 5-BB-C | 5.0% |
| 2-PyB-2 | 2.0% |
| 3-PyB-2 | 2.0% |
| 4-PyB-2 | 2.0% |
| 6-PyB-O5 | 3.0% |
| 6-PyB-O6 | 3.0% |
| 6-PyB-O7 | 3.0% |
| 6-PyB-O8 | 3.0% |
| 3-PyBB-F | 6.0% |
| 4-PyBB-F | 6.0% |
| 5-PyBB-F | 6.0% |
| 3-HHB-1 | 6.0% |
| 3-HHB-3 | 8.0% |
| 2-H2BTB-2 | 4.0% |
| 2-H2BTB-3 | 4.0% |
| 2-H2BTB-4 | 5.0% |
| 3-H2BTB-2 | 5.0% |
| 3-H2BTB-3 | 5.0% |
| 3-H2BTB-4 | 5.0% |

The physical properties of this composition are shown below.

$T_{NI}$=92.4 (° C.)

η=36.7 (mPa·s)

Δn=0.195

Δ∈=7.2

$V_{TH}$=2.11 (V)

Composition Example 4

| | |
|---|---|
| VFF2-B(F,F)B(F)-C (No. 8) | 5.0% |
| VFF-B(F,F)B(F)-C (No. 2) | 5.0% |
| 3-GB-C | 10.0% |
| 2-BEB-C | 12.0% |
| 3-BEB-C | 4.0% |
| 3-PyB(F)-F | 6.0% |
| 3-HEB-O4 | 8.0% |
| 4-HEB-O2 | 6.0% |
| 5-HEB-O1 | 6.0% |
| 3-HEB-O2 | 5.0% |
| 5-HEB-O2 | 4.0% |
| 5-HEE-5 | 5.0% |
| 4-HED-5 | 5.0% |
| 1O-BEB-2 | 4.0% |
| 3-HHB-1 | 6.0% |
| 3-HHEBB-C | 3.0% |
| 3-HBEBB-C | 3.0% |
| 5-HDEBD-C | 3.0% |

The physical properties of this composition are shown below.

$T_{NI}$=61.1 (° C.)

η=42.7 (mPa·s)

Δn=0.122

Δ∈=12.8

$V_{TH}$=1.14 (V)

Composition Example 5

| | |
|---|---|
| VFF-HEB(F,F)-C (No. 33) | 15.0% |
| 3-HB-C | 3.0% |
| 7-HB-C | 3.0% |
| 1O1-HB-C | 10.0% |
| 3-HB(F)-C | 10.0% |
| 2-PyB-2 | 2.0% |
| 3-PyB-2 | 2.0% |
| 4-PyB-2 | 2.0% |
| 1O1-HH-3 | 7.0% |
| 2-BTB-O1 | 7.0% |
| 3-HHB-1 | 7.0% |
| 3-HHB-F | 4.0% |
| 3-HHB-O1 | 4.0% |
| 3-HHB-3 | 8.0% |
| 3-H2BTB-2 | 3.0% |
| 3-H2BTB-3 | 3.0% |
| 2-PyBH-3 | 4.0% |
| 3-PyBH-3 | 3.0% |
| 3-PyBB-2 | 3.0% |

Composition Example 6

| | |
|---|---|
| VFF-B(F)B(F,F)-C (No. 9) | 5.0% |
| 3-BEB(F)-C | 4.0% |
| 4-BEB(F)-C | 12.0% |
| 1V2-BEB(F,F)-C | 10.0% |
| 3-HH-EMe | 10.0% |
| 3-HB-O2 | 18.0% |
| 7-HEB-F | 2.0% |
| 3-HHEB-F | 2.0% |
| 5-HHEB-F | 2.0% |
| 3-HBEB-F | 4.0% |
| 2O1-HBEB(F)-C | 2.0% |
| 3-HB(F)EB(F)-C | 2.0% |
| 3-HBEB(F,F)-C | 2.0% |
| 3-HHB-F | 4.0% |
| 3-HHB-O1 | 4.0% |
| 3-HHB-3 | 13.0% |
| 3-HEBEB-F | 2.0% |
| 3-HEBEB-1 | 2.0% |

The physical properties of this composition are shown below.

$T_{NI}$=75.4 (° C.)

η=36.2 (mPa·s)

Δn=0.117

Δ∈=24.0

$V_{TH}$=0.95 (V)

Composition Example 7

| | |
|---|---|
| VFF-HEB(F,F)-C (No. 33) | 5.0% |
| 3-BEB(F)-C | 4.0% |
| 4-BEB(F)-C | 12.0% |
| 1V2-BEB(F,F)-C | 16.0% |
| 3-HB-O2 | 10.0% |
| 3-HH-4 | 3.0% |
| 3-HHB-F | 3.0% |
| 3-HHB-1 | 8.0% |
| 3-HHB-O1 | 4.0% |
| 3-HBEB-F | 4.0% |
| 3-HHEB-F | 7.0% |
| 5-HHEB-F | 7.0% |
| 3-H2BTB-2 | 4.0% |
| 3-H2BTB-3 | 4.0% |

-continued

| | |
|---|---|
| 3-H2BTB-4 | 4.0% |
| 3-HB(F)TB-2 | 5.0% |

Composition Example 8

| | |
|---|---|
| VFF-GB(F,F)-C (No. 29) | 10.0% |
| VFF-HB(F,F)-C (No. 53) | 10.0% |
| 2-BEB-C | 12.0% |
| 3-BEB-C | 4.0% |
| 4-BEB-C | 6.0% |
| 3-HB-C | 8.0% |
| 3-HEB-O4 | 12.0% |
| 4-HEB-O2 | 8.0% |
| 5-HEB-O1 | 8.0% |
| 3-HEB-O2 | 6.0% |
| 5-HEB-O2 | 5.0% |
| 3-HHB-1 | 7.0% |
| 3-HHB-O1 | 4.0% |

Composition Example 9

| | |
|---|---|
| VFF-B(F,F)B-C (No. 1) | 7.0% |
| 2-BEB-C | 10.0% |
| 5-BB-C | 12.0% |
| 1-BTB-3 | 7.0% |
| 2-BTB-1 | 10.0% |
| 1O-BEB-2 | 10.0% |
| 1O-BEB-5 | 12.0% |
| 2-HHB-1 | 4.0% |
| 3-HHB-F | 4.0% |
| 3-HHB-1 | 7.0% |
| 3-HHB-O1 | 4.0% |
| 3-HHB-3 | 13.0% |

The physical properties of this composition are shown below.

$T_{NI}$=62.9 (° C.)

η=22.3 (mPa·s)

Δn=0.158

Δ∈=7.4

$V_{TH}$=1.58 (V)

Composition Example 10

| | |
|---|---|
| VFF-HEB(F,F)-C (No. 33) | 12.0% |
| 2-HB-C | 5.0% |
| 3-HB-O2 | 15.0% |
| 2-BTB-1 | 3.0% |
| 3-HHB-1 | 8.0% |
| 3-HHB-F | 4.0% |
| 3-HHB-O1 | 5.0% |
| 3-HHB-3 | 14.0% |
| 3-HHEB-F | 4.0% |
| 5-HHEB-F | 4.0% |
| 2-HHB(F)-F | 7.0% |
| 3-HHB(F)-F | 7.0% |
| 5-HHB(F)-F | 7.0% |
| 3-HHB(F,F)-F | 5.0% |

Composition Example 11

| | |
|---|---|
| VFF-B(F,F)B-C (No. 1) | 3.0% |
| 3-BEB(F)-C | 8.0% |
| 3-HB-C | 5.0% |
| V-HB-C | 8.0% |
| 1V-HB-C | 8.0% |
| 3-HB-O2 | 3.0% |
| 3-HH-2V | 14.0% |
| 3-HH-2V1 | 7.0% |
| V2-HHB-1 | 15.0% |
| 3-HHB-1 | 5.0% |
| 3-HHEB-F | 7.0% |
| 3-H2BTB-2 | 6.0% |
| 3-H2BTB-3 | 6.0% |
| 3-H2BTB-4 | 5.0% |

The physical properties of this composition are shown below.

$T_{NI}$=97.0 (° C.)

η=17.2 (mPa·s)

Δn =0.134

Δ∈=8.8

$V_{TH}$=2.08 (V)

Composition Example 12

| | |
|---|---|
| VFF-B(F,F)B-C (No. 1) | 5.0% |
| VFF-B(F)B(F,F)-C (No. 9) | 5.0% |
| VFF-GB(F,F)-C (No. 29) | 5.0% |
| VFF-HEB(F,F)-C (No. 33) | 5.0% |
| V2-HB-C | 12.0% |
| 1V2-HB-C | 12.0% |
| 3-HB-C | 4.0% |
| 3-HB(F)-C | 5.0% |
| 2-BTB-1 | 2.0% |
| 3-HH-4 | 8.0% |
| 3-HH-VFF | 6.0% |
| 2-HHB-C | 3.0% |
| 3-HHB-C | 6.0% |
| 3-HB(F)TB-2 | 8.0% |
| 3-H2BTB-2 | 5.0% |
| 3-H2BTB-3 | 5.0% |
| 3-H2BTB-4 | 4.0% |

Composition Example 13

| | |
|---|---|
| VFF2-B(F)B(F,F)-C (No. 6) | 5.0% |
| 5-BEB(F)-C | 5.0% |
| V-HB-C | 11.0% |
| 5-PyB-C | 6.0% |
| 4-BB-3 | 11.0% |
| 3-HH-2V | 10.0% |
| 5-HH-V | 11.0% |
| V-HHB-1 | 7.0% |
| V2-HHB-1 | 15.0% |
| 3-HHB-1 | 4.0% |
| 1V2-HBB-2 | 10.0% |
| 3-HHEBH-3 | 5.0% |

The physical properties of this composition are shown below.

$T_{NI}$=80.9 (° C.)

η=16.8 (mPa·s)

Δn 0.116

$\Delta\epsilon$=6.2

$V_{TH}$=1.89 (V)

Composition Example 14

| | |
|---|---|
| VFF-B(F,F)B(F)-C (No. 10) | 5.0% |
| 1V2-BEB(F,F)-C | 8.0% |
| 3-HB-C | 5.0% |
| V2V-HB-C | 14.0% |
| V2V-HH-3 | 19.0% |
| 3-HB-O2 | 4.0% |
| 3-HHB-1 | 10.0% |
| 3-HHB-3 | 15.0% |
| 3-HB(F)TB-2 | 4.0% |
| 3-HB(F)TB-3 | 4.0% |
| 3-H2BTB-2 | 4.0% |
| 3-H2BTB-3 | 4.0% |
| 3-H2BTB-4 | 4.0% |

The physical properties of this composition are shown below.

$T_{NI}$=96.7 (° C.)

η=19.6 (mPa·s)

Δn=0.130

$\Delta\epsilon$=8.8

$V_{TH}$=1.64 (V)

Composition Example 15

| | |
|---|---|
| VFF-HB(F,F)-C (No. 53) | 5.0% |
| V2-HB-TC | 10.0% |
| 3-HB-TC | 10.0% |
| 3-HB-C | 5.0% |
| 5-HB-C | 7.0% |
| 5-BB-C | 3.0% |
| 2-BTB-1 | 10.0% |
| 2-BTB-O1 | 5.0% |
| 3-HH-4 | 5.0% |
| 3-HHB-1 | 10.0% |
| 3-HHB-3 | 11.0% |
| 3-H2BTB-2 | 3.0% |
| 3-H2BTB-3 | 3.0% |
| 3-HB(F)TB-2 | 3.0% |
| 5-BTB(F)TB-3 | 10.0% |

Composition Example 16

| | |
|---|---|
| VFF2-B(F,F)B-C (No. 7) | 5.0% |
| VFF2-B(F,F)B(F)-C (No. 8) | 5.0% |
| VFF2-B(F)B(F,F)-C (No. 6) | 5.0% |
| 1V2-BEB(F,F)-C | 6.0% |
| 3-HB-C | 3.0% |
| 2-BTB-1 | 10.0% |
| 5-HH-VFF | 30.0% |
| 1-BHH-VFF | 8.0% |
| 1-BHH-2VFF | 11.0% |
| 3-H2BTB-2 | 5.0% |
| 3-H2BTB-3 | 4.0% |
| 3-H2BTB-4 | 4.0% |
| 3-HHB-1 | 4.0% |

The physical properties of this composition are shown below.

$T_{NI}$=68.3 (° C.)

η=18.2 (mPa·s)

Δn=0.130

$\Delta\epsilon$=9.0

$V_{TH}$=1.62 (V)

Composition Example 17

| | |
|---|---|
| VFF-B(F,F)B-C (No. 1) | 5.0% |
| VFF-B(F,F)B(F)-C (No. 10) | 5.0% |
| VFF-B(F)B(F,F)-C (No. 9) | 5.0% |
| 5-HBCF2OB(F,F)-C | 3.0% |
| 3-HB(F,F)CF2OB(F,F)-C | 3.0% |
| 3-HB-C | 3.0% |
| 2-BTB-1 | 10.0% |
| 5-HH-VFF | 30.0% |
| 1-BHH-VFF | 8.0% |
| 1-BHH-2VFF | 11.0% |
| 3-H2BTB-2 | 5.0% |
| 3-H2BTB-3 | 4.0% |
| 3-H2BTB-4 | 4.0% |
| 3-HHB-1 | 4.0% |

The physical properties of this composition are shown below.

$T_{NI}$=71.6 (° C.)

η=19.0 (mPa·s)

Δn =0.127

$\Delta\epsilon$=7.0

$V_{TH}$=1.87 (V)

Composition Example 18

| | |
|---|---|
| VFF-HB(F,F)-C (No. 53) | 16.0% |
| 2-HHB(F)-F | 17.0% |
| 3-HHB(F)-F | 17.0% |
| 2-H2HB(F)-F | 10.0% |
| 3-H2HB(F)-F | 5.0% |
| 5-H2HB(F)-F | 10.0% |
| 2-HBB(F)-F | 6.0% |
| 3-HBB(F)-F | 6.0% |
| 5-HBB(F)-F | 13.0% |

Composition Example 19

| | |
|---|---|
| VFF-HEB(F,F)-C (No. 33) | 10.0% |
| 7-HB(F,F)-F | 3.0% |
| 3-HB-O2 | 7.0% |
| 2-HHB(F)-F | 10.0% |
| 3-HHB(F)-F | 10.0% |
| 2-HBB(F)-F | 9.0% |
| 3-HBB(F)-F | 9.0% |
| 5-HBB(F)-F | 16.0% |
| 2-HBB-F | 4.0% |
| 3-HBB-F | 4.0% |
| 5-HBB-F | 3.0% |
| 3-HBB(F,F)-F | 5.0% |
| 5-HBB(F,F)-F | 10.0% |

Composition Example 20

| | |
|---|---|
| VFF2-B(F,F)B-C (No. 7) | 3.0% |
| VFF2-B(F,F)B(F)-C (No. 8) | 3.0% |
| VFF2-B(F)B(F,F)-C (No. 6) | 3.0% |
| 5-HB-CL | 16.0% |

-continued

| | |
|---|---|
| 3-HH-4 | 12.0% |
| 3-HH-5 | 4.0% |
| 3-HHB-F | 4.0% |
| 3-HHB-CL | 3.0% |
| 4-HHB-CL | 4.0% |
| 3-HHB(F)-F | 10.0% |
| 4-HHB(F)-F | 9.0% |
| 7-HHB(F)-F | 8.0% |
| 5-HBB(F)-F | 4.0% |
| 5-HBBH-1O1 | 3.0% |
| 3-HHBB(F,F)-F | 2.0% |
| 4-HHBB(F,F)-F | 3.0% |
| 5-HHBB(F,F)-F | 3.0% |
| 3-HH2BB(F,F)-F | 3.0% |
| 4-HH2BB(F,F)-F | 3.0% |

The physical properties of this composition are shown below.

$T_{NI}$=100.8 (° C.)

η=23.0 (mPa·s)

Δn=0.095

Δ∈=5.8

$V_{TH}$=2.47 (V)

Composition Example 21

| | |
|---|---|
| VFF-HB(F,F)-C (No. 53) | 4.0% |
| VFF-HEB(F,F)-C (No. 33) | 4.0% |
| VFF-GB(F,F)-C (No. 29) | 4.0% |
| VFF-B(F,F)B-C (No. 1) | 4.0% |
| VFF-B(F,F)B(F)-C (No. 10) | 4.0% |
| VFF-B(F)B(F,F)-C (No. 9) | 4.0% |
| VFF2-B(F)B(F,F)-C (No. 6) | 4.0% |
| 3-HHB(F,F)-F | 9.0% |
| 3-H2HB(F,F)-F | 8.0% |
| 4-H2HB(F,F)-F | 8.0% |
| 3-HBB(F,F)-F | 21.0% |
| 3-H2BB(F,F)-F | 10.0% |
| 5-HHBB(F,F)-F | 3.0% |
| 5-HHEBB-F | 2.0% |
| 3-HH2BB(F,F)-F | 3.0% |
| 4-HBBH-1O1 | 4.0% |
| 5-HBBH-1O1 | 4.0% |

Composition Example 22

| | |
|---|---|
| VFF-GB(F,F)-C (No. 29) | 10.0% |
| 5-HB-F | 12.0% |
| 6-HB-F | 9.0% |
| 7-HB-F | 7.0% |
| 2-HHB-OCF3 | 7.0% |
| 3-HHB-OCF3 | 7.0% |
| 4-HHB-OCF3 | 7.0% |
| 5-HHB-OCF3 | 5.0% |
| 3-HH2B-OCF3 | 4.0% |
| 5-HH2B-OCF3 | 4.0% |
| 3-HHB(F,F)-OCF3 | 5.0% |
| 3-HBB(F)-F | 10.0% |
| 3-HH2B(F)-F | 3.0% |
| 3-HB(F)BH-3 | 3.0% |
| 5-HBBH-3 | 3.0% |
| 3-HHB(F,F)-OCF2H | 4.0% |

The physical properties of this composition are shown below.

$T_{NI}$=74.8 (° C.)

η=20.0 (mPa·s)

Δn=0.082

Δ∈=6.7

$V_{TH}$=1.91 (V)

Composition Example 23

| | |
|---|---|
| VFF-GB(F,F)-C (No. 29) | 5.0% |
| VFF-B(F,F)B-C (No. 1) | 5.0% |
| VFF-B(F)B(F,F)-C (No. 9) | 5.0% |
| 2-HHB(F)-F | 3.0% |
| 2-HBB(F)-F | 7.0% |
| 3-HBB(F)-F | 7.0% |
| 4-HBB(F)-F | 2.0% |
| 2-H2BB(F)-F | 10.0% |
| 3-H2BB(F)-F | 10.0% |
| 3-HBB(F,F)-F | 22.0% |
| 5-HBB(F,F)-F | 6.0% |
| 2-HHB(F,F)-F | 5.0% |
| 3-HHB(F,F)-F | 5.0% |
| 4-HHB(F,F)-F | 5.0% |
| 3-HHB-F | 3.0% |

Composition Example 24

| | |
|---|---|
| VFF2-B(F,F)B-C (No. 7) | 5.0% |
| VFF-B(F,F)B-C (No. 1) | 5.0% |
| VFF-HEB(F,F)-C (No. 33) | 5.0% |
| 5-HB-CL | 11.0% |
| 3-HH-4 | 8.0% |
| 3-HBB(F,F)-F | 20.0% |
| 3-HHB(F,F)-F | 8.0% |
| 3-HHEB(F,F)-F | 10.0% |
| 4-HHEB(F,F)-F | 3.0% |
| 5-HHEB(F,F)-F | 3.0% |
| 2-HBEB(F,F)-F | 3.0% |
| 3-HBEB(F,F)-F | 5.0% |
| 5-HBEB(F,F)-F | 3.0% |
| 3-HHBB(F,F)-F | 6.0% |
| 3-HHB-1 | 5.0% |

Composition Example 25

| | |
|---|---|
| VFF-HEB(F,F)-C (No. 33) | 11.0% |
| 7-HB(F)-F | 6.0% |
| 5-H2B(F)-F | 6.0% |
| 3-HB-O2 | 4.0% |
| 3-HH-4 | 12.0% |
| 2-HHB(F)-F | 11.0% |
| 3-HHB(F)-F | 11.0% |
| 2-HBB(F)-F | 2.0% |
| 3-HBB(F)-F | 2.0% |
| 5-HBB(F)-F | 4.0% |
| 3-HBB(F,F)-F | 3.0% |
| 2-HHBB(F,F)-F | 4.0% |
| 3-HHBB(F,F)-F | 5.0% |
| 3-HHEB-F | 4.0% |
| 5-HHEB-F | 4.0% |
| 3-HHB-1 | 7.0% |
| 3-HHB-3 | 4.0% |

Composition Example 26

| | |
|---|---|
| VFF-HEB(F,F)-C (No. 33) | 16.0% |
| VFF-GB(F,F)-C (No. 29) | 16.0% |
| 3-HH-4 | 4.0% |
| 3-H2HB(F,F)-F | 10.0% |
| 4-H2HB(F,F)-F | 10.0% |
| 5-H2HB(F,F)-F | 8.0% |
| 3-HBB(F,F)-F | 33.0% |
| 3-HHBB(F,F)-F | 3.0% |

Composition Example 27

| | |
|---|---|
| VFF2-B(F,F)B(F)-C (No. 8) | 5.0% |
| 7-HB(F,F)-F | 5.0% |
| 3-H2HB(F,F)-F | 12.0% |
| 4-H2HB(F,F)-F | 10.0% |
| 3-HHB(F,F)-F | 10.0% |
| 3-HBB(F,F)-F | 10.0% |
| 3-HHEB(F,F)-F | 10.0% |
| 4-HHEB(F,F)-F | 3.0% |
| 5-HHEB(F,F)-F | 3.0% |
| 2-HBEB(F,F)-F | 3.0% |
| 3-HBEB(F,F)-F | 5.0% |
| 5-HBEB(F,F)-F | 3.0% |
| 3-HGB(F,F)-F | 15.0% |
| 3-HHBB(F,F)-F | 6.0% |

The physical properties of this composition are shown below.

$T_{NI}$=69.2 (° C.)

η=35.9 (mPa·s)

Δn=0.086

Δ∈=14.1

$V_{TH}$=1.26 (V)

Composition Example 28

| | |
|---|---|
| VFF-B(F,F)B(F)-C (No. 10) | 5.0% |
| 5-H4HB(F,F)-F | 7.0% |
| 5-H4HB-OCF3 | 15.0% |
| 3-H4HB(F,F)-CF3 | 8.0% |
| 5-H4HB(F,F)-CF3 | 10.0% |
| 3-HB-CL | 6.0% |
| 5-HB-CL | 4.0% |
| 2-H2BB(F)-F | 5.0% |
| 3-H2BB(F)-F | 10.0% |
| 5-H2HB(F,F)-F | 5.0% |
| 3-HHB-OCF3 | 5.0% |
| 3-H2HB-OCF3 | 5.0% |
| V-HHB(F)-F | 5.0% |
| 3-HHB(F)-F | 5.0% |
| 3-HBEB(F,F)-F | 5.0% |

The physical properties of this composition are shown below.

$T_{NI}$=61.6 (° C.)

η=27.9 (mPa·s)

Δn=0.099

Δ∈=9.5

$V_{TH}$=1.57 (V)

Composition Example 29

| | |
|---|---|
| VFF-B(F)B(F,F)-C (No. 9) | 7.0% |
| 5-HB-CL | 17.0% |
| 7-HB(F,F)-F | 3.0% |
| 3-HH-4 | 10.0% |
| 3-HH-5 | 5.0% |
| 3-HB-O2 | 15.0% |
| 3-H2HB(F,F)-F | 5.0% |
| 4-H2HB(F,F)-F | 5.0% |
| 3-HHB(F,F)-F | 6.0% |
| 2-HHB(F)-F | 7.0% |
| 3-HHB(F)-F | 7.0% |
| 3-HHB-1 | 8.0% |
| 3-HHB-O1 | 5.0% |

The physical properties of this composition are shown below.

$T_{NI}$=59.9 (° C.)

η=16.4 (mPa·s)

Δn=0.076

Δ∈=4.5

$V_{TH}$=2.39 (V)

Composition Example 30

| | |
|---|---|
| VFF2-B(F)B(F,F)-C (No. 6) | 3.0% |
| 5-HB-CL | 4.0% |
| 4-HHB(F)-F | 10.0% |
| 5-HHB(F)-F | 9.0% |
| 7-HHB(F)-F | 9.0% |
| 3-HHB(F,F)-F | 8.0% |
| 3-H2HB(F,F)-F | 12.0% |
| 3-HBB(F,F)-F | 22.0% |
| 2-HHBB(F,F)-F | 6.0% |
| 3-GHB(F,F)-F | 3.0% |
| 4-GHB(F,F)-F | 8.0% |
| 5-GHB(F,F)-F | 6.0% |

The physical properties of this composition are shown below.

$T_{NI}$=76.3 (° C.)

η=32.8 (mPa·s)

Δn=0.091

Δ∈=9.3

$V_{TH}$=1.59 (V)

Composition Example 31

| | |
|---|---|
| VFF-HB(F,F)-C (No. 53) | 7.0% |
| 2-HHB(F)-F | 7.0% |
| 3-HHB(F)-F | 8.0% |
| 3-HHB(F,F)-F | 8.0% |
| 3-HBB(F,F)-F | 21.0% |
| 3-H2HB(F,F)-F | 10.0% |
| 3-HHEB(F,F)-F | 10.0% |
| 4-HHEB(F,F)-F | 3.0% |
| 2-HBEB(F,F)-F | 2.0% |
| 3-HBEB(F,F)-F | 3.0% |
| 3-GHB(F,F)-F | 3.0% |
| 4-GHB(F,F)-F | 7.0% |
| 5-GHB(F,F)-F | 7.0% |
| 3-HHBB(F,F)-F | 4.0% |

Composition Example 32

| | |
|---|---|
| VFF-B(F,F)B(F)-C (No. 10) | 5.0% |
| 7-HB(F)-F | 7.0% |
| 5-HB-CL | 3.0% |
| 3-HH-4 | 9.0% |
| 3-HH-EMe | 23.0% |
| 3-HHEB(F,F)-F | 10.0% |
| 3-HHEB-F | 8.0% |
| 5-HHEB-F | 8.0% |
| 4-HGB(F,F)-F | 5.0% |
| 5-HGB(F,F)-F | 6.0% |
| 2-H2GB(F,F)-F | 4.0% |
| 3-H2GB(F,F)-F | 5.0% |
| 5-GHB(F,F)-F | 7.0% |

The physical properties of this composition are shown below.

$T_{NI}$=72.2 (° C.)

η=21.6 (mPa·s)

Δn=0.066

Δ∈=6.8

$V_{TH}$=1.80 (V)

Composition Example 33

| | |
|---|---|
| VFF-HB(F,F)-C (No. 53) | 15.0% |
| VFF-HEB(F,F)-C (No. 33) | 15.0% |
| 3-H2HB(F,F)-F | 5.0% |
| 5-H2HB(F,F)-F | 5.0% |
| 3-HBB(F,F)-F | 30.0% |
| 5-HBB(F)B-2 | 10.0% |
| 5-HBB(F)B-3 | 10.0% |
| 3-BB(F)B(F,F)-F | 5.0% |
| 5-B2B(F,F)B(F)-F | 5.0% |

Composition Example 34

| | |
|---|---|
| VFF-B(F)B(F,F)-C (No. 9) | 3.0% |
| 3-HB(F,F)CF2OB(F,F)-F | 11.0% |
| 5-HB(F,F)CF2OB(F,F)-F | 11.0% |
| 5-HB-CL | 7.0% |
| 3-HH-4 | 14.0% |
| 2-HH-5 | 4.0% |
| 3-HHB-1 | 4.0% |
| 3-HHEB-F | 6.0% |
| 5-HHEB-F | 6.0% |
| 3-HHB(F,F)-F | 6.0% |
| 3-HHEB(F,F)-F | 8.0% |
| 4-HHEB(F,F)-F | 3.0% |
| 5-HHEB(F,F)-F | 2.0% |
| 2-HBEB(F,F)--F | 3.0% |
| 3-HBEB(F,F)-F | 3.0% |
| 5-HBEB(F,F)-F | 3.0% |
| 2-HHBB(F,F)-F | 3.0% |
| 3-HHBB(F,F)-F | 3.0% |

The physical properties of this composition are shown below.

$T_{NI}$=77.5 (° C.)

η=21.7 (mPa·s)

Δn=0.080

Δ∈=8.9

$V_{TH}$=1.63 (V)

Composition Example 35

| | |
|---|---|
| VFF2-B(F,F)B-C (No. 7) | 5.0% |
| 3-BB(F,F)CF2OB(F,F)-F | 35.0% |
| 3-HH-4 | 8.0% |
| 3-HHB(F,F)-F | 10.0% |
| 3-H2HB(F,F)-F | 9.0% |
| 3-HBB(F,F)-F | 10.0% |
| 2-HHBB(F,F)-F | 3.0% |
| 3-HHBB(F,F)-F | 3.0% |
| 3-HH2BB(F,F)-F | 4.0% |
| 3-HHB-1 | 6.0% |
| 5-HBBH-1O1 | 7.0% |

The physical properties of this composition are shown below.

$T_{NI}$=76.8 (° C.)

η=29.6 (mPa·s)

Δn=0.117

Δ∈=12.9

$V_{TH}$=1.33 (V)

Composition Example 36

| | |
|---|---|
| VFF-B(F,F)B-C (No. 1) | 7.0% |
| VFF-B(F)B(F,F)-C (No. 9) | 7.0% |
| 3-HEB-O4 | 28.0% |
| 4-HEB-O2 | 20.0% |
| 5-HEB-O1 | 20.0% |
| 3-HEB-O2 | 18.0% |

The physical properties of this composition are shown below.

$T_{NI}$=60.7 (° C.)

η=24.6 (mPa·s)

Δn=0.097

Composition Example 37

| | |
|---|---|
| VFF2-B(F,F)B-C (No. 7) | 6.0% |
| 3-HH-2 | 5.0% |
| 3-HH-O1 | 4.0% |
| 3-HH-O3 | 5.0% |
| 5-HH-O1 | 4.0% |
| 3-HB(2F,3F)-O2 | 12.0% |
| 5-HB(2F,3F)-O2 | 11.0% |
| 3-HHB(2F,3F)-O2 | 14.0% |
| 5-HHB(2F,3F)-O2 | 15.0% |
| 3-HHB(2F,3F)-2 | 24.0% |

The physical properties of this composition are shown below.

$T_{NI}$=80.5 (° C.)

Δn=0.088

Δ∈=−2.5

Composition Example 38

| | |
|---|---|
| VFF-HB(F,F)-C (No. 53) | 5.0% |
| 3-HH-5 | 5.0% |
| 3-HH-O1 | 6.0% |
| 3-HH-O3 | 6.0% |
| 3-HB-O1 | 5.0% |
| 3-HB-O2 | 5.0% |
| 3-HB(2F,3F)-O2 | 10.0% |
| 5-HB(2F,3F)-O2 | 10.0% |
| 3-HHB(2F,3F)-O2 | 12.0% |
| 5-HHB(2F,3F)-O2 | 13.0% |
| 3-HHB(2F,3F)-2 | 4.0% |
| 2-HHB(2F,3F)-1 | 4.0% |
| 3-HHEH-3 | 5.0% |
| 3-HHEH-5 | 5.0% |
| 4-HHEH-3 | 5.0% |

The compounds represented by the formula (1) can be easily prepared by the known methods, for example, those disclosed in A. Suzuki, *Metal-Catalyzed Cross-coupling Reactions*, Eds. F. Dietrich, P. J. Stang, Wiley-VCH, Weinheim, 1998, pp. 49–97 and EP 0330216A. The descriptions of the relevant parts in the literatures are incorporated herein by reference.

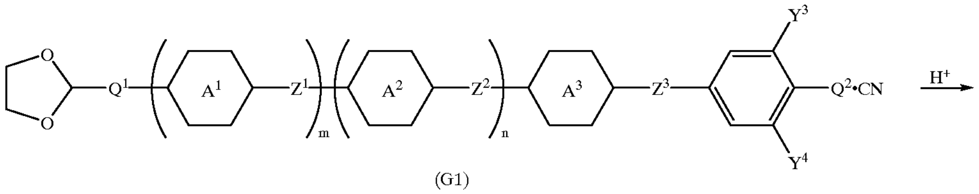

(G1)

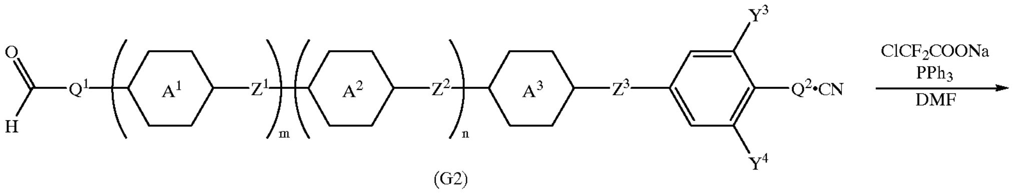

(G2)

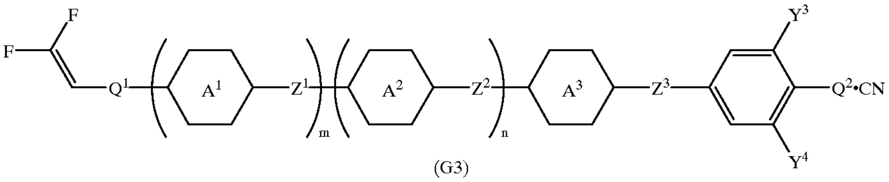

(G3)

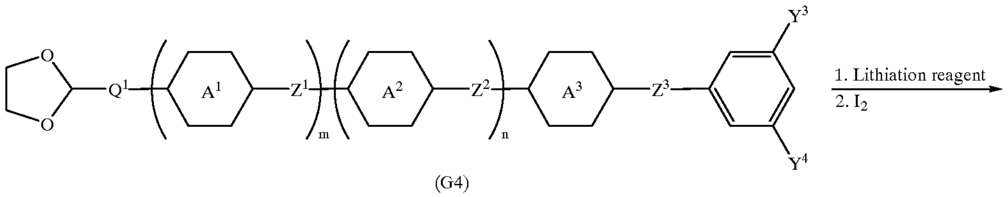

(G4)

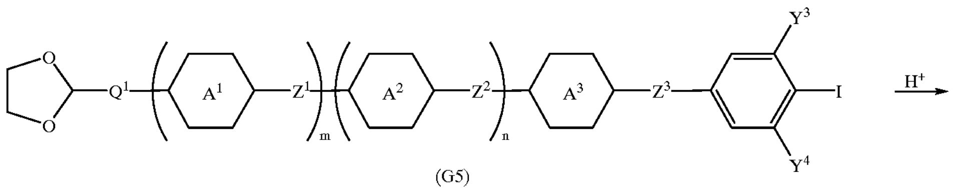

(G5)

-continued

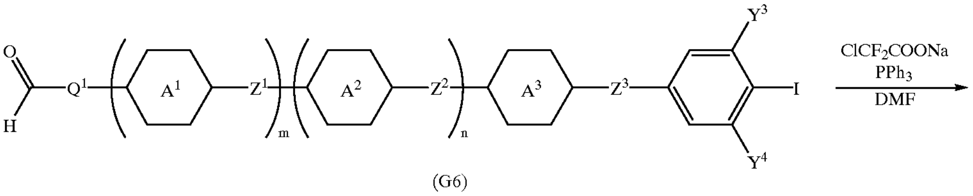

(G6)

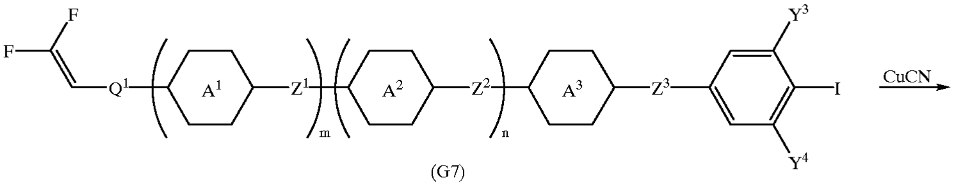

(G7)

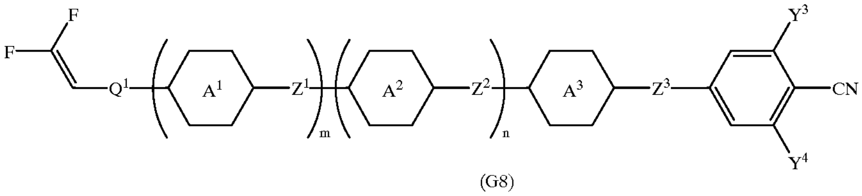

(G8)

The compound represented by the formula (1) wherein both $Y^1$ and $Y^2$ are a fluorine atom (compound (G3)) can be synthesized by treating a compound (G1) with an acid thereby converting it into aldehyde (G2), which is then reacted with triphenylphosphine and sodium chlorodifluoroacetate. A compound (G7) can be synthesized by reacting a compound (G4) with a lithiation reagent and then iodine, or alternatively with periodic acid, iodine and sulfuric acid (H. Suzuki, *Org. Synth.*, VI, p. 700 (1988)), to produce an iodine compound (G5), which is then treated in the similar manner used in synthesizing the compound (G3) from the compound (G1). The descriptions of the related parts in the literature are incorporated herein by reference. The compound (G7) is then cyanated with a metal cyanide such as copper cyanide to prepare the compound represented by the formula (1) wherein $Q^2$ is a single bond (compound (G8)).

Now, the method for synthesizing the compound represented by the formula (1) wherein both m and n is 0 will be described in detail below.

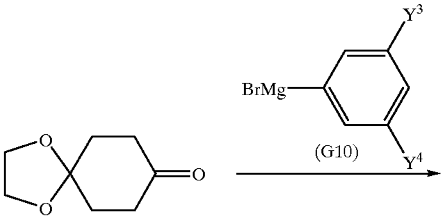

(G9) (G10)

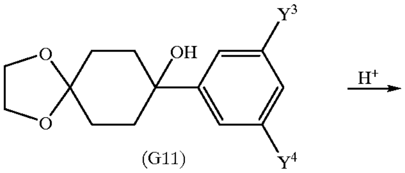

(G11)

-continued

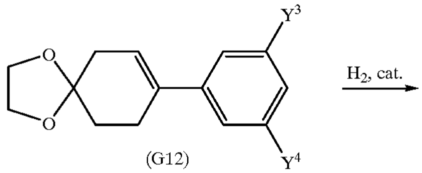

(G12)

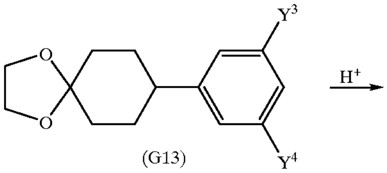

(G13)

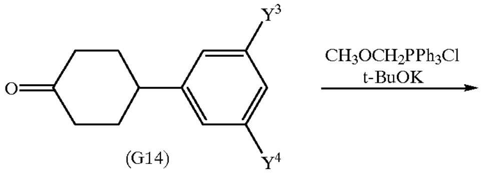

(G14)

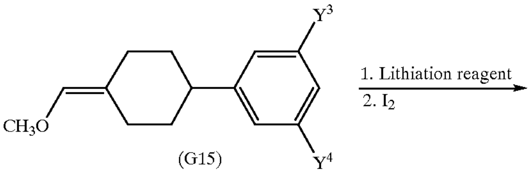

(G15)

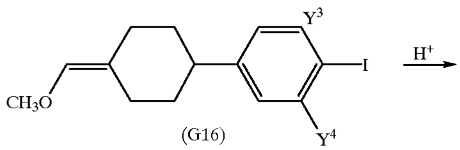

(G16)

-continued

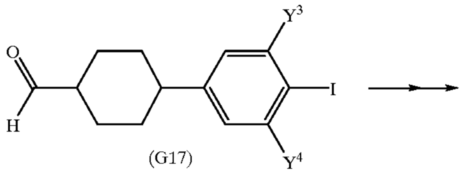

(G17)

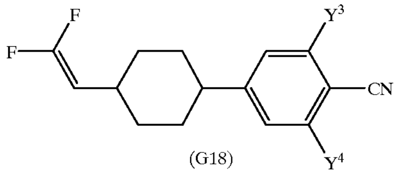

(G18)

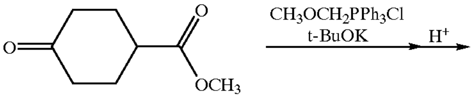

(G19)

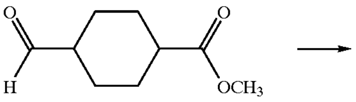

(G20)

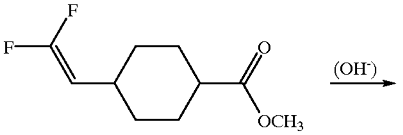

(G21)

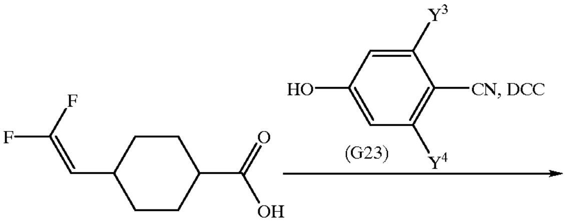

(G22)

(G23)

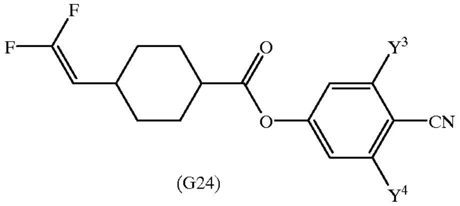

(G24)

Synthesis of Compound (G18)

Cyclohexanedion monoacetal (G9) is reacted with Grignard reagent (G10) to give an alcohol (G11), which is then dehydrated with an acid to prepare a compound (G12). The compound (G12) is hydrogenated in the presence of a catalyst such as palladium/carbon or Raney nickel to produce a compound (G13), which is then treated with an acid to form a ketone (G14). Ketone (G14) is subjected to Wittig reaction using methoxymethyl triphenyl phohsphonium chloride to produce a compound (G15), which is then iodinated to produce a compound (G16). The compound (G16) is then treated with an acid to prepare an aldehyde (G17). The compound represented by the formula (1) wherein the alkylene group for $Q^1$ has a longer chain length can be synthesized by repeatedly subjecting the aldehyde (G17) to Wittig reaction using methoxymethyl triphenylphohsphonium chloride and the treatment with an acid.

The compound (18) can be synthesized in the same manner as used in synthesizing the compound (G8), except for using the aldehyde (G17) instead of the compound (G6).

Synthesis of Compound (G24)

The compound (G20) can be synthesized by subjecting the compound (G19) to Wittig reaction using methoxymethyl triphenylphosphonium chloride, followed by treatment with an acid. The compound (21) can be synthesized in the same manner as used in synthesizing the compound (G7), except for using the compound (G20) instead of the compound (G6). The compound (G21) is saponified to produce carboxylic acid (G22), which is then reacted with phenol (G23) using a dehydrating agent such as dicyclohexyl carbodiimide (DCC) to prepare a compound (24). The compound (G24) can also be prepared by dehydration condensation of carboxylic acid (G22) and phenol (G23) in the presence of sulfuric acid as a catalyst, or reacting carboxylic acid (G22) with thionyl chloride to form an acid chloride, which is then reacted with phenol (G23) in a basic solvent such as pyridine.

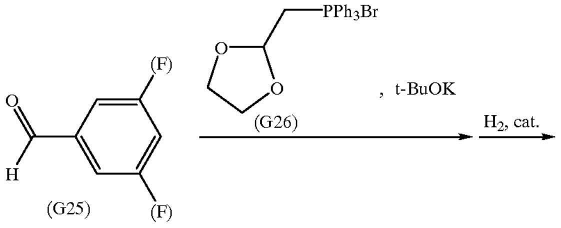

(G25)

(G26)

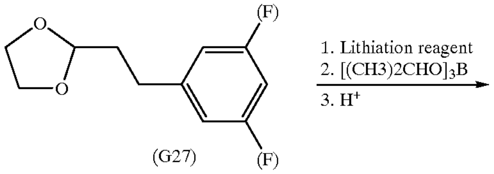

(G27)

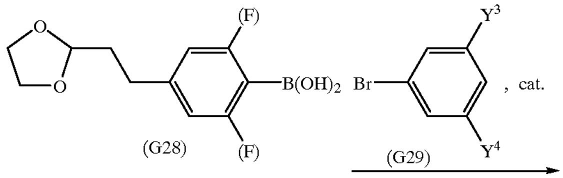

(G28)

(G29)

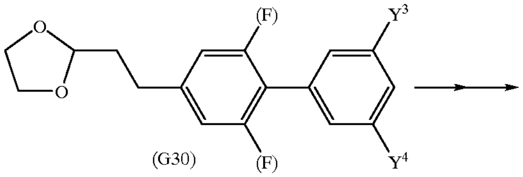

(G30)

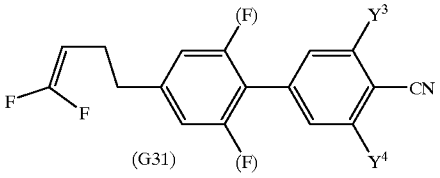

(G31)

(G27)

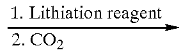

-continued

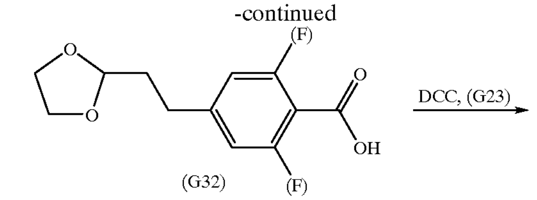

(G32)

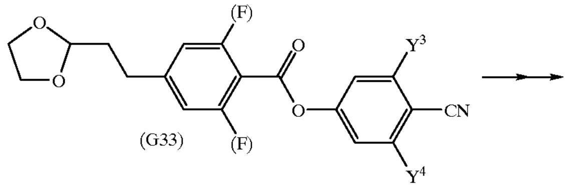

(G33)

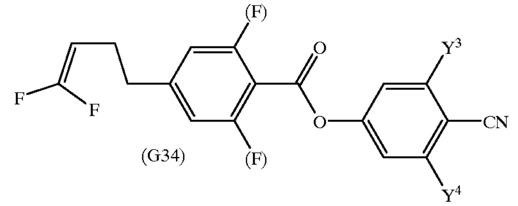

(G34)

In the formulas (G25), (G27), (G28), (G30), (G31), (G32), (G33) and (G34), the symbol (F) denotes F or H.

Synthesis of Compound (G31)

The compound (G27) can be prepared by subjecting the aldehyde (G25) to Wittig reaction using 1,3-dioxolan-2-ylmethyltriphenyl phosphonium bromide and then hydrogenating the resultant substance in the presence of a catalyst such as Raney nickel or palladium/carbon. The compound (G27) is reacted with a lithiation reagent such as n-butyl lithium or sec-butyl lithium and then triisopropyl borate, followed by treatment with an acid thereby producing boronic acid (G28). The boronic acid (G28) is reacted with the compound (G29) following the procedure disclosed in A. Suzuki, *Metal-Catalyzed Cross-coupling Reactions*, Eds. F. Dietrich, P. J. Stang, Wiley-VCH, Weinheim, 1998, pp. 49–97 to prepare the compound (G30). When the phenylene group of the compound (G28) is 3-fluoro-1,4-phenylene or 1,4-phenylene, the compound (G30) can also be synthesized by the method disclosed in *J. Chem. Soc. Perkin Trans.* 2, 2041 (1989). The compound (31) can be synthesized in the same manner as used in synthesizing the compound (G8), except for using the compound (G30) instead of the compound (G4). The compound (G31) wherein each of the symbol (F) is H can be synthesized by initiating the process using 4-bromobenzaldehyde in place of the compound (G25). The descriptions of the related parts in the literatures are incorporated herein by reference.

Synthesis of Compound (G34)

The compound (G27) is subjected to a lithiation reaction with n-butyl lithium or sec-butyl lithium followed by a reaction with dry ice to produce carboxylic acid (G32). Carboxylic acid (G32) is then reacted with phenol (G23) using a dehydrating agent such as dicyclohexyl carbodiimide (DCC) to form an ester (G33). The compound (34) can be synthesized in the same manner as used in synthesizing the compound (G3), except for using the compound (G33) instead of the compound (G1). The ester (G33) and the compound (G34) wherein each of the symbol (F) is H can be synthesized by initiating the process using 4-(1,3-dioxolan-1-ylethyl)-bromobenzene in the place of the compound (G27).

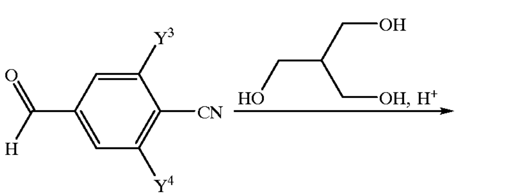

(G35)

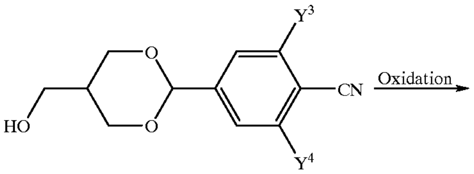

(G36)

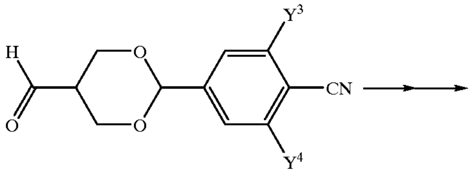

(G37)

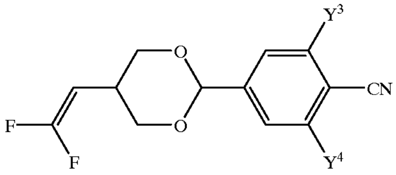

(G38)

Synthesis of Compound (G38)

An aldehyde (G35) is reacted with 2-hydroxymethyl-1,3-propane diol in the presence of an acid catalyst such as p-toluenesulfonic acid to produce a compound (G36). The compound (G36) is oxidated by the Swern oxidation or the PCC oxidation disclosed in A. J. Mancuso, S. L. Huang, D. Swern, *J. Org. Chem.,* 43, p. 2480 (1978) and K. Hori, Y. Ohfune, ibid., 53, p. 3886 (1988) to produce a compound (G37). The compound (G38) can be synthesized in the same manner as used in synthesizing the compound (G3), except for using the compound (G37) instead of the compound (G2). The descriptions of the related parts in the literatures are incorporated herein by reference.

The compounds represented by the formula (1) wherein n is 1 can be synthesized by suitably combining the methods described above, the methods in the following examples and the ordinary methods used in organic synthesis. Any person of ordinary skill in the art will understand that various alterations and improvements are suitably allowable within the spirit and the scope of the claimed invention.

EXAMPLES

The present invention will be more specifically illustrated below with reference to the following examples, which should not be construed to limit the invention in any way.

In the examples, the symbol C-I denotes a crystal-isotropic liquid phase transition temperature.

Example 1

Preparation of 1-(4,4-difluoro-3-butenyl)-3,5-difluoro-4-(4-cyanophenyl)benzene (Compound No. 7)

[The compound of the formula (1) wherein $Y^1=Y^2=F$, $Y^3=Y^4=H$, $Q^1=—CH_2CH_2—$, m=n=0, ring $A^3$ is a 3,5-difluoro-1,4-phenylene group, $Z^3$ is a single bond, and $Q^2$ is a single bond]

Step 1

To 95.0 g (221 mmol) of dried 1,3-dioxolan-2-ylmethyl triphenylphosphonium bromide was added 800 ml of tetrahydrofuran (hereinafter abbreviated as "THF"), and the mixture was cooled to 0° C. 25.0 g (223 mmol) of potassium-t-butoxide was gradually added thereto at that temperature and the mixture was stirred for one hour. To the resulting mixture was added dropwise a solution of 25.0 g (176 mmol) of 3,5-difluorobenzaldehyde in 50 ml of THF and the mixture was stirred at 0° C. for one hour and then stirred at room temperature for 12 hours. 500 ml of water was added thereto and the reaction product was extracted with toluene. The extract was washed with brine, dried over magnesium sulfate, and the solvent was distilled off under reduced pressure. The residue was purified by column chromatography on silica gel (eluting solvent: toluene) and the solvent was distilled off under reduced pressure. The residue thus obtained was dissolved in 600 ml of ethanol and the resultant solution was hydrogenated with 5% palladium/carbon as a catalyst and filtered to separate the catalyst. The solvent was distilled off under reduced pressure to afford 30.9 g (154 mmol) of 1-(1,3-dioxolan-2-ylethyl)-3,5-difluorobenzene. (Yield: 87.5%)

Step 2

30.9 g (154 mmol) of 1-(1,3-dioxolan-2-ylethyl)-3,5-difluorobenzene obtained above was dissolved in 250 ml of THF under an atmosphere of nitrogen, and the solution was cooled to −70° C. To the solution was added dropwise 100 ml of a solution of n-butyl lithium in hexane (1.54 mol/L) and the mixture was stirred at that temperature for one hour. Further, 32.0 g of triisopropyl borate was added dropwise thereto while keeping the temperature at −70° C., and the mixture were stirred for one hour followed by addition of 100 ml of water. The resultant mixture was added to 200 ml of ice water and adjusted to pH 3 by the addition of 6N-hydrochloric acid. The reaction product was extracted with ether and the solvent was distilled off under reduced pressure to afford 30 g (116 mmol) of 4-(1,3-dioxolan-2-ylethyl)-2,6-difluorophenylboronic acid.

(Yield: 75.3%)

Step 3

To 150 ml of N,N-dimethyl formamide (hereinafter abbreviated as "DMF") were added 7.0 g (27 mmol) of 4-(1,3-dioxolan-2-ylethyl)-2,6-difluruphenyl boronic acid obtained in Step 2, 5.0 g (27 mmol) of 4-bromobenzonitrile, 10 g (99 mmol) of triethyl amine, 0.20 g (0.89 mmol) of palladium acetate and 0.50 g (1.9 mmol) of triphenylphosphine and the mixture was refluxed for 4 hours. The solvent was distilled off under reduced pressure. To the residue of this distillation were added 500 ml of methylene chloride and 250 ml of a 10% aqueous ammonia and the mixture was stirred. The organic layer was dried over magnesium sulfate and the solvent was distilled off under reduced pressure. The residue was purified by column chromatography on silica gel (eluting solvent: toluene/ethyl acetate=5/1) and then the solvent was distilled off under reduced pressure. The residue thus obtained was washed with ethanol and then dried under reduced pressure to afford 4.4 g (14 mmol) of 1-(1,3-dioxolan-2-ylethyl)-3,5-difluoro-4-(4-cyanophenyl)benzene. (Yield: 52%)

Step 4

4.4 g (14 mmol) of 1-(1,3-dioxolan-2-ylethyl)-3,5-difluoro-4-(4-cyanophenyl)benzene obtained above was added to a mixed solvent of 75 ml of acetone and 75 mmol of 3N-hydrochloric acid and the mixture was stirred for 3 hours. The reaction product was extracted with toluene. The extract was washed with saturated aqueous sodium bicarbonate and then with water and dried over magnesium sulfate. The solvent was distilled off under reduced pressure to afford 3.3 g (12 mmol) of 3-(4-(4-cyanophenyl)-3,5-difluorophenyl)propanal.

(Yield: 86%)

Step 5

3.0 g (11 mmol) of 3-(4-(4-cyanophenyl)-3,5-difluorophenyl)propanal obtained above and 4.4 g (17 mmol) of triphenylphosphine were added to 100 ml of DMF and the mixture was heated to 120° C. To the solution was added dropwide a solution of 3.5 g of sodium chlorodifluoroacetate in 50 ml DMF and the mixture was stirred for 2 hours while keeping the temperature at 120° C. The reaction solution was cooled down to room temperature and filtered with Celite. 300 ml of water was added to the filtrate and the reaction product was extracted with toluene. The organic layer was washed with saturated aqueous sodium bicarbonate and then with water and dried over magnesium sulfate. The solvent was distilled off under reduced pressure and the residue was purified by column chromatography on silica gel (eluting solvent: heptane/ethyl acetate=3/1). The solvent was distilled off under reduce pressure and the residue thus obtained was recrystallied twice with ethanol to afford 0.9 g (2.9 mmol) of 1-(4,4-difluoro-3-butenyl)-3,5-difluoro-4-(4-cyanophenyl)benzene.

(Yield: 26%)

$^1$H-NMR ($CDCl_3$) δ (ppm):

7.79–7.52 (m, 4H), 6.97–6.74 (m, 2H), 4.18 (ddt, 1H), 2.73 (t, 2H), 2.47–2.30 (m, 2H) C-I 89.1° C.

Example 2

Preparation of 1-(4,4-difluoro-3-butenyl)-3,5-difluoro-4-(3-fluoro-4-cyanophenyl)benzene (Compound No. 8)

[the compound of the formula (1) wherein $Y^1=Y^2=Y^3=F$, $Y^4=H$, $Q^1=—CH_2CH_2—$, m=n=0, Ring $A^3$ is a 3,5-difluoro-1,4-phenylene group, $Z^3$ is a single bond, and $Q^2$ is a single bond]

Step 1

To 300 ml of DMF were added 14 g (54 mmol) of 4-(1,3-dioxolan-2-ylethyl)-2,6-difluorophenylboric acid obtained in Step 2 of Example 1, 10 g (50 mmol) of 2-floro-4-bromobenzonitrile, 20 g (198 mol) of triethyl amine, 0.50 g (2.2 mmol) of palladium acetate, and 0.50 g (3.8 mmol) of triphenylphosphine, and the mixture was refluxed for 7 hours. The solvent was distilled off under reduced pressure. To the residue were added 700 ml of methylene chloride and 300 ml of a 10% aqueous ammonia, and the mixture was stirred. The organic layer was dried over magnesium sulfate. The solvent was distilled off under reduced pressure and the residue was purified by column chromatography on silica gel (eluting solvent: toluene/ethyl acetate=5/1). The solvent was distilled under reduced pressure and the residue was washed with ethanol and then dried under reduced pressure to afford 11 g (33 mmol) of 1-(1,3-dioxolan-2-ylethyl)-3,5-difluoro-4-(3-fluoro-4-cyanophenyl)benzene.

(Yield: 61%)

Step 2

11 g (33 mmol) of 1-(1,3-dioxolan-2-ylethyl)-3,5-difluoro-4-(3-fluoro-4-cyanophenyl)benzene obtained above was added to a mixed solvent of 150 ml of acetone and 150 mmol of 3N-hydrochloric acid, and the mixture was stirred for 3 hours. The reaction product was extracted with toluene. The extract was washed with saturated aqueous sodium bicarbonate and then with water and dried over magnesium sulfate. The solvent was distilled off under reduced pressure to afford 8.0 g (28 mmol) of 3-(4-(3-fluoro-4-cyanophenyl)-3,5-difluorophenyl)propanal.

(Yield: 85%)

Step 3

8.0 g (28 mmol) of 3-(4-(3-fluoro-4-cyanophenyl)-3,5-difluorophenyl)propanal obtained above and 15 g (57 mmol) of triphenylphosphine were added to 300 ml of DMF, and the mixture was heated to 130° C. To the resultant mixture was added dropwise a solution of 12 g (79 mmol) of sodium chlorodifluoroacetate in 100 ml of DMF, and the mixture was stirred for 2 hours at that temperature. The reaction solution was cooled down to room temperature and filtered with Celite. 300 ml of water was then added to the filtrate, and the resulting product was extracted with toluene. The organic layer was washed with saturated aqueous sodium bicarbonate and then with water and dried over magnesium sulfate. The solvent was distilled off under reduced pressure and the residue was purified by column chromatography on silica gel (eluting solvent: toluene). The solvent was distilled off under reduced pressure and the residue was recrystallized twice with ethanol to afford 3.2 g (9.9 mmol) of 1-(4,4-difluoro-3-butenyl)-3,5-difluoro-4-(3-fluoro-4-cyanophenyl)benzene.

(Yield: 35%)

$^1$H-NMR ($CDCl_3$) δ (ppm): 7.71–7.68 (m, 1H), 7.40–7.26 (m, 2H), 6.88–6.86 (m, 2H), 4.17 (ddt, 1H), 2.73 (t, 2H), 2.37 2.32 (m, 2H) C-I 72.1° C.

Example 3

Preparation of 1-(2,2-difluorovinyl)-4-(3,5-difluoro-4-cyanophenyl)cyclohexane (Compound No. 53)

[the compound of the formula (1) wherein $Y^1=Y^2=Y^3=Y^4=F$, $Q^1$ is a single bond, m=n=0, Ring $A^3$ is a trans-1,4-cyclohexylene group, $Z^3$ is a single bond, and $Q^2$ is a single bond]

Step 1

A Grignard reagent prepared from dried magnesium and 50 g (0.26 mol) of 1-bromo-3,5-diflorobenzene in THF was added dropwide at room temperature to a solution of 34 g (0.22 mol) of cyclohexanedion monoethylene ketal in 500 ml of THF and the mixture was stirred for 5 hours. The reaction solution was added to 500 ml of a saturated ammonium chloride and the mixture was stirred. The reaction product was extracted with ether. The extract was dried over magnesium sulfate and the solvent was distilled off. The residue and 2 g of p-toluenesulfonic acid were added to 300 ml of toluene, and the mixture was refluxed for 3 hours, while removing the produced water using Dean-Stark. The reaction solution was washed successively with water, a saturated aqueous sodium carbonate and water, dried over magnesium sulfate, and then the solvent was distilled off. The residue was purified by column chromatography on silica gel (eluting solvent: heptane/ethyl acetate=3/1), and the solvent was distilled off under reduced pressure. The residue thus obtained was hydrogenated in ethanol in the presence of 2 g of 5% palladium/carbon. The catalyst was filtered off and then the solvent was distilled off to afford 31 g (0.12 mol) of 4-(3,5-difluorophenyl)-cyclohexanone mono-ethylene ketal.

(Yield: 55%)

Step 2

To 50 ml of toluene was added 31 g (0.12 mol) of 4-(3,5-difluorophenyl)cyclohexanone monoethylene ketal obtained above and 76 g (1.7 mol) of formic acid, and the mixture was refluxed for 4 hours. The reaction solution was successively with water, a saturated aqueous sodium carbonate and water, dried over magnesium sulfate, and then the solvent was distilled off to afford 26 g of 4-(3,5-difluorophenyl)cyclohexanone.

To 600 ml of THF was added 60 g (0.18 mol) of dried methoxymethyltriphenylphosphonium chloride and the mixture was cooled to 0° C. 20 g (0.18 mol) of potassium t-butoxide was gradually added thereto, and the mixture was stirred for 2 hours as at that temperature. To the reaction solution was added dropwise a solution of 26 g (0.12 mol) of 4-(3,5-difluorophenyl)cyclohexanone obtained above in 200 ml of THF, and the mixture was warmed to room temperature and stirred for 10 hours. After adding water to the reaction solution, the reaction product was extracted with toluene, the extract was washed with water and the solvent was distilled off. The residue was purified by column chromatography on silica gel (eluting solvent: toluene) and the solvent was distilled off under reduced pressure. The residue thus obtained was added to a mixed solvent of 300 ml of 3N hydrochloric acid and 600 ml of acetone and the mixture was stirred for 3 hours. The reaction product was extracted with toluene, the extract was washed successively with a saturated aqueous sodium bicarbonate and water, dried over magnesium sulfate, and the solvent was then distilled off. The residue thus obtained, 1 g of p-toluenesulfonic acid and 14 g of trimethylene glycol were refluxed in 200 ml of toluene for 3 hours. The reaction solution was washed successively with a saturated aqueous sodium bicarbonate and water, and the solvent was then distilled off. The residue was purified by column chromatography on silica gel (eluting solvent: toluene) and the solvent was then distilled off under reduced pressure to afford 30 g (0.11 mol) of 4-(3,5-difluorophenyl) cyclohexanecarboaldehyde propylene ketal.

(Yield: 92%)

Step 3

30 g (0.11 mol) of 4-(3,5-difluorophenyl)-cyclohexanecarboaldehyde propylene ketal obtained above dissolved in 400 ml of THF was cooled to −78° C. To the solution was added dropwise 80 ml (0.12 mol) of n-butyl lithium (1.5 mol/L) added and the mixture was stirred for 2 hours. Then a solution of 32 g (0.13 mol) of iodine in 200 ml of THF was added dropwise thereto followed by stirring for 3 hours. The reaction solution was added to a saturated aqueous sodium thiosulfate, the product thus obtained was extracted with toluene. The extract was dried over magnesium sulfate and the solvent was distilled off. The residue thus obtained was recrystallized with ethanol to afford 33 g (0.081 mol) of 4-(3,5-difluoro-4-iodophenyl) cyclohexanecarboaldehyde propylene ketal.

(Yield: 74%)

Step 4

To 50 ml of toluene were added 23 g (56 mmol) of 4-(3,5-difluoro-4-iodophenyl)cyclohexanecarboaldehyde propylene ketal obtained above and 39 g (848 mmol) of formic acid, and the mixture was refluxed for 2 hours. The reaction solution was washed with water, further with a saturated aqueous sodium bicarbonate and then with water and dried over magnesium sulfate. The solvent was distilled off to afford 19 g (54 mmol) of 4-(3,5-difluoro-4-iodophenyl)cyclohexanecarboaldehyde.

19 g (54 mmol) of 4-(3,5-difluoro-4-iodophenyl) cyclohexane carboaldehyde obtained above and 30 g (114 mmol) of triphenylphosphine in 300 ml of DMF were heated to 130° C. To the resultant solution was added dropwise a solution of 26 g (170 mmol) of sodium chlorodifluoroacetate in 300 ml of DMF and the mixture was stirred for 2 hours. The reaction solution was cooled down to room temperature and filtered with Celite. After adding 300 ml of water to the filtrate, the reaction product was extracted with toluene. The organic layer was washed with a saturated aqueous sodium bicarbonate and then with water and dried over magnesium sulfate. The solvent was distilled off under reduced pressure and the residue was purified by column chromatography on silica gel (eluting solvent: heptane). The solvent was distilled off under reduced pressure and the residue was recrystallized with ethanol to afford 11 g (29 mmol) of 1-(2,2-diflorovinyl)-4-(3,5-difluoro-4-iodophenyl)cyclohexane.

(Yield 52%)

Step 5

8.0 g (21 mmol) of 1-(2,2-diflorovinyl)-4-(3,5-difluoro-4-iodophenyl)cyclohexane obtained above and 2.3 g (26 mmol) of copper cyanide were added to 100 ml of DMF and the mixture was stirred at 140° C. for 10 hours. The reaction product was extracted with toluene, the extract was washed three times with aqueous ammonia and three times with water and dried over magnesium sulfate. The solvent was distilled off and the residue was purified by column chromatography on silica gel (eluting solvent: heptane/toluene=1/1). The solvent was distilled off under reduced pressure and the residue was recrystallized with ethanol to afford 3.5 g (12 mmol) of 1-(2,2-difluorovinyl)-4-(3,5-difluoro-4-cyanophenyl)cyclohexane.

(Yield: 57%)

$^1$H-NMR ($CDCl_3$) δ (ppm): 6.90–6.88 (m, 2H), 4.06 (ddd, 1H), 2.55 (m, 1H), 2.22 (m, 1H), 1.93–1.24 (m, 8H) C-I 50.2° C.

Example 4

Preparation of 1-(trans-2-fluorovinyl)-4-(3,5-difluoro-4-cyanophenyl)cyclohexane (Compound No. 81)

[the compound of the formula (1) wherein $Y^1=Y^3=Y^4$=F, $Y^2$=H, $Q^1$ is a single bond, m=n=0, Ring $A^3$ is a trans-1,4-cyclohexylene group, $Z^3$ is a single bond, and $Q^2$ is a single bond]

To a mixture of 2.0 g (7.06 mmol) of 1-(2,2-difluorovinyl)-4-(3,5-difluoro-4-cyanophenyl)cyclohexane prepared in Example 3 and 50 ml of toluene was added 3.3 g of bis(2-methoxyethoxy)aluminum hydride (a 65% toluene solution, equivalent to 10.6 mmol). The reaction mixture was stirred for 15 hours under reflux.

The resultant reaction mixture was cooled to room temperature and introduced in 100 ml of water. The toluene layer separated was washed three times with 50 ml of 6M hydrochloric acid, further washed with water until it became neutral, and dried over anhydrous magnesium sulfate. The solid was filtered off and the solvent was distilled off to obtain the concentrated product. The residue thus obtained was purified by column chromatography on silica gel (eluting solvent: toluene) and recrystallized 8 times with heptane to afford 225 mg (0.85 mmol) of 1-(trans-2-fluorovinyl)-4-(3,5-difluoro-4-cyanophenyl)cyclohexane.

(Yield: 12%) IR (KBr): δ=2221 $cm^{-1}$ (Ar—CN) $^1$H-NMR ($CDCl_3$) δ (ppm):

1.25–1.95 (m, 8H), 2.25 (m, 1H), 2.56 (m, 1H), 5.09 (ddd, 1H), 6.40 (ddd, 1H), 6.79–6.88 (m, 4H)

HRMS: Calcd. ($C_{15}H_{14}F_3N$): 265.10783, Found: 265.1077.

According to the descriptions in Examples 1–4 and the section of the "Detailed Description of the Invention", the following compounds 1–81 can be prepared, which include the compounds prepared in Examples 1–4.

No. 1

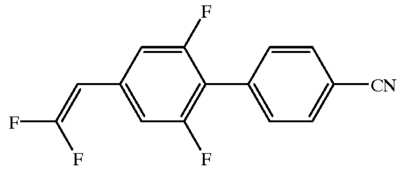

No. 2

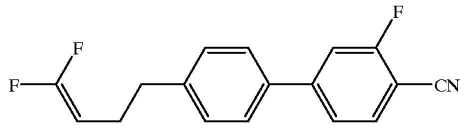

No. 3

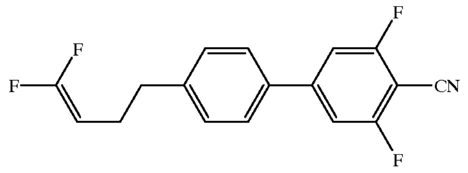

No. 4

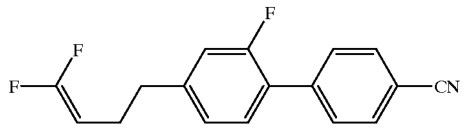

No. 5

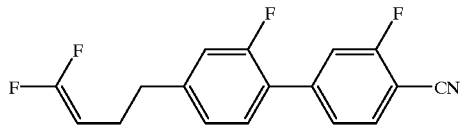

No. 6

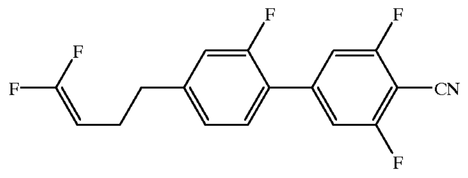

No. 7

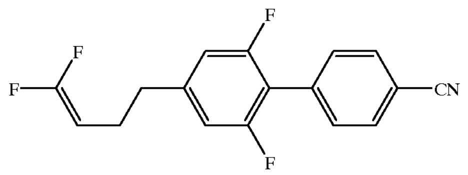

-continued
No. 8
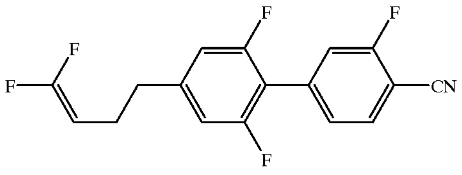
No. 9
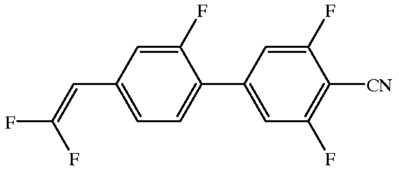
No. 10
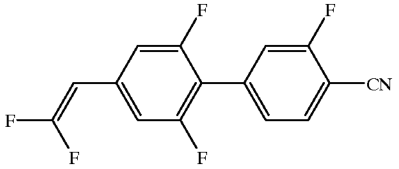
No. 11
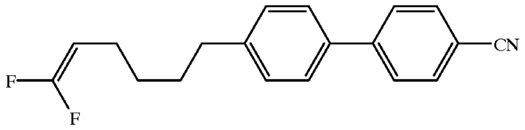
No. 12
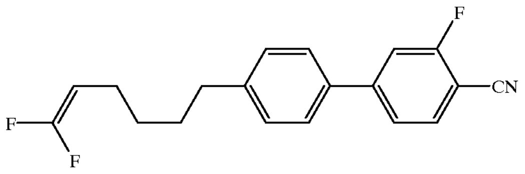
No. 13
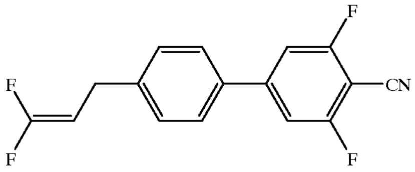
No. 14
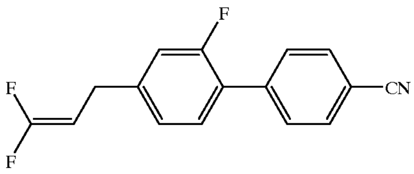
No. 15
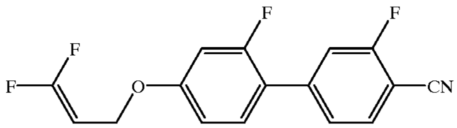
-continued
No. 16
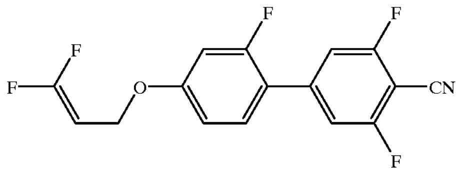
No. 17
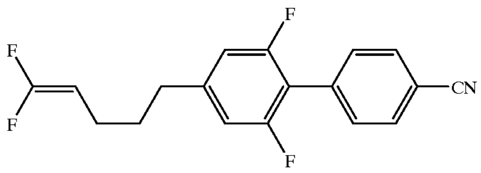
No. 18
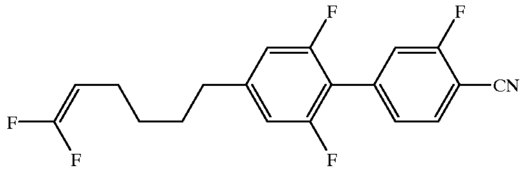
No. 19
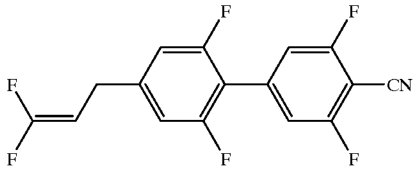
No. 20
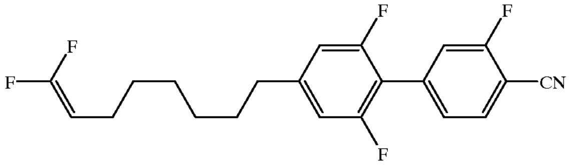
No. 21
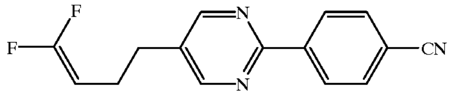
No. 22
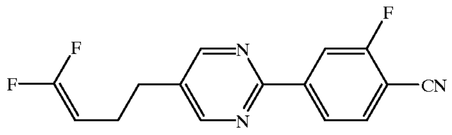
No. 23
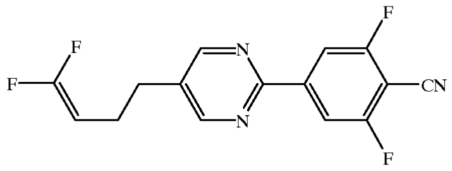
No. 24
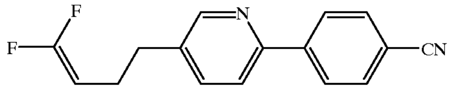

-continued
No. 25
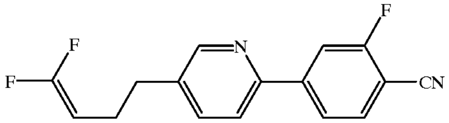
No. 26
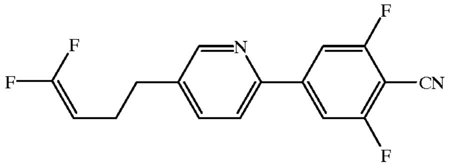
No. 27
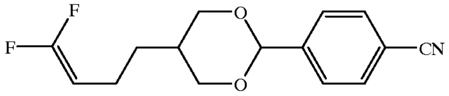
No. 28
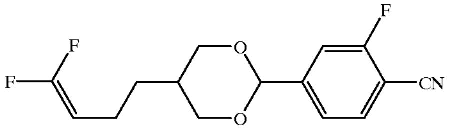
No. 29
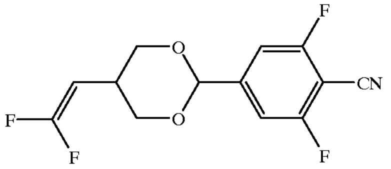
No. 30
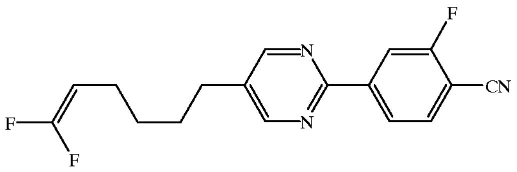
No. 31
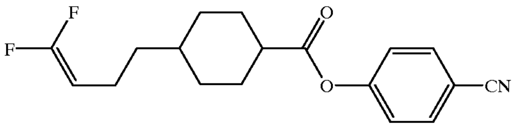
No. 32
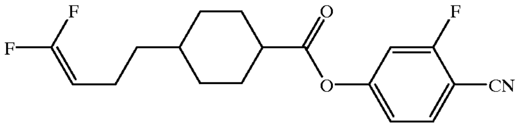
No. 33
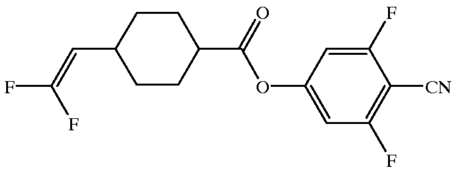
-continued
No. 34
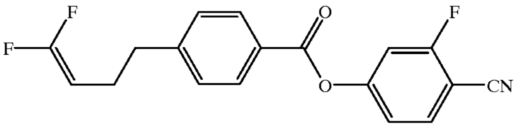
No. 35
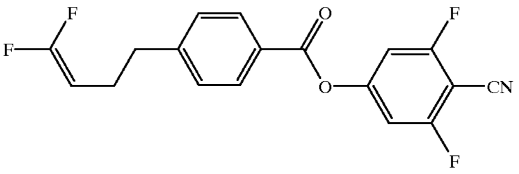
No. 36
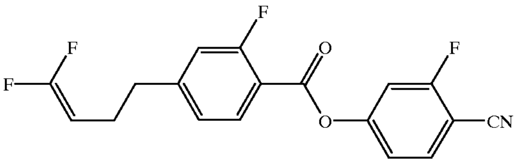
No. 37
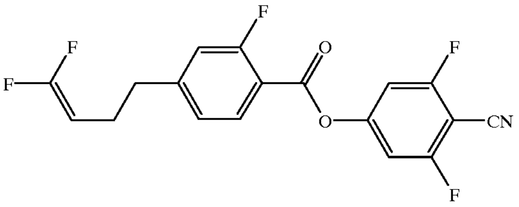
No. 38
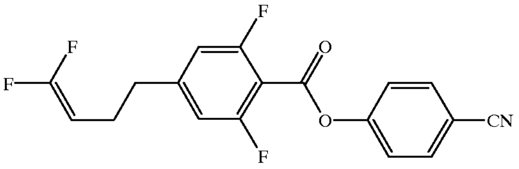
No. 39
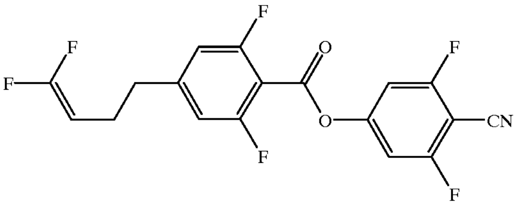
No. 40
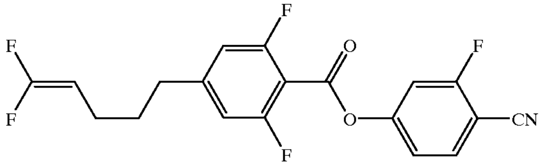
No. 41
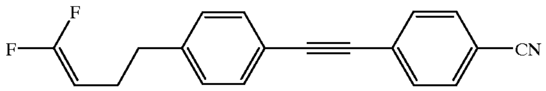

-continued
No. 42
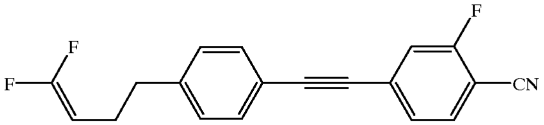
No. 43
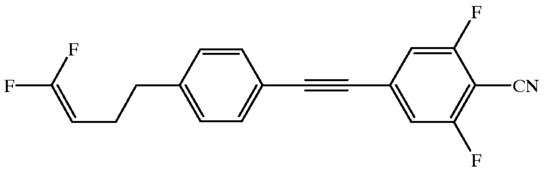
No. 44
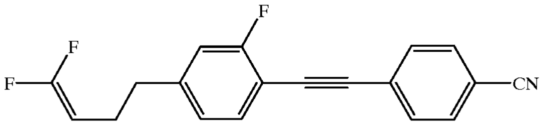
No. 45
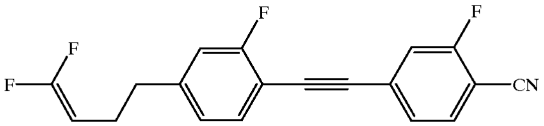
No. 46
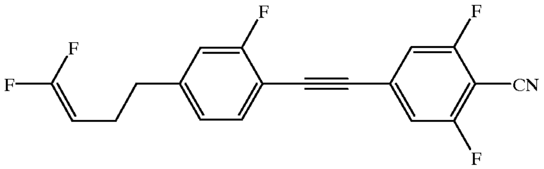
No. 47
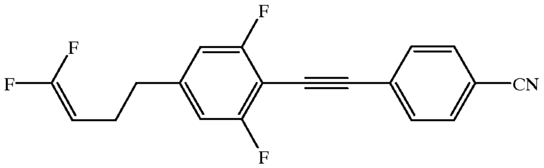
No. 48
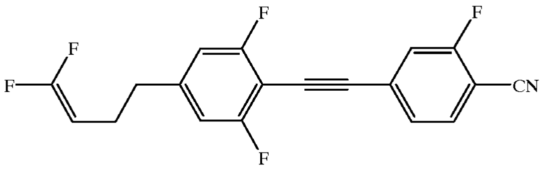
No. 49
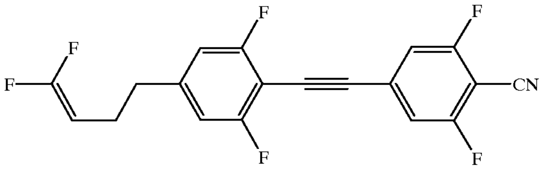
-continued
No. 50
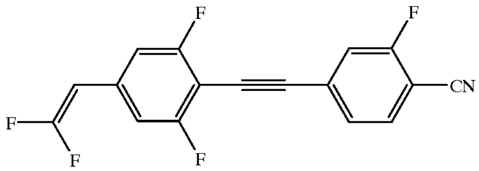
No. 51
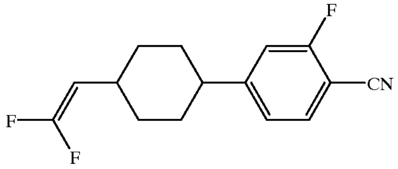
No. 52
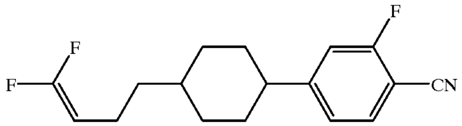
No. 53
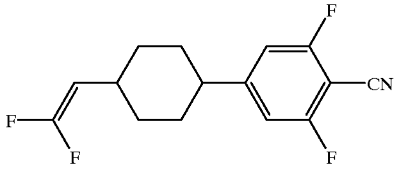
No. 54
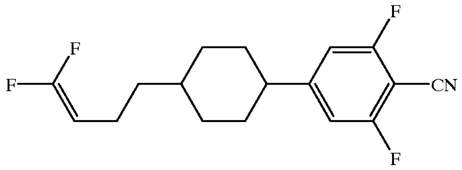
No. 55
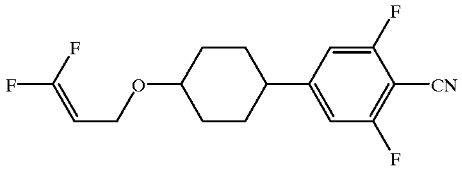
No. 56
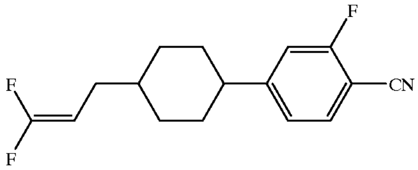
No. 57
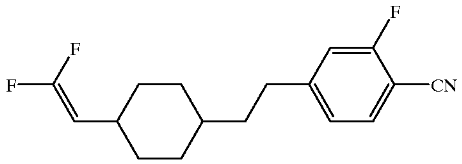

-continued
No. 58
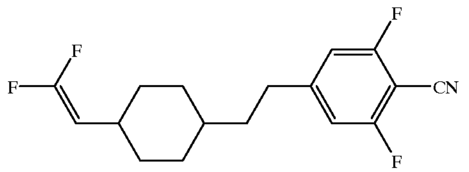
No. 59
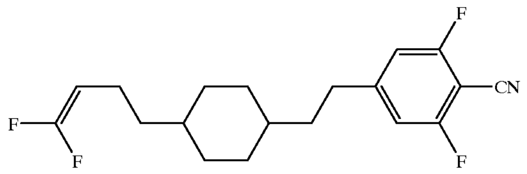
No. 60
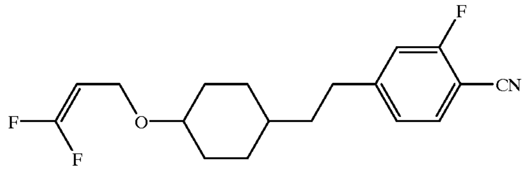
No. 61
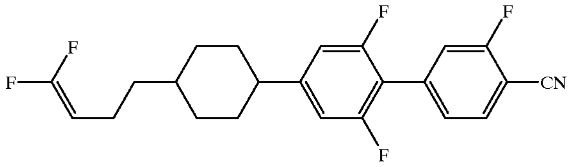
No. 62
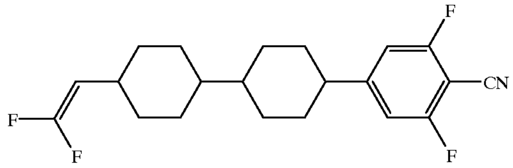
No. 63
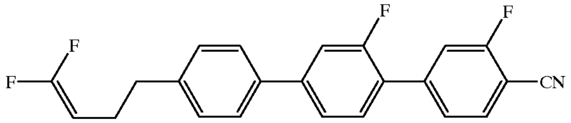
No. 64
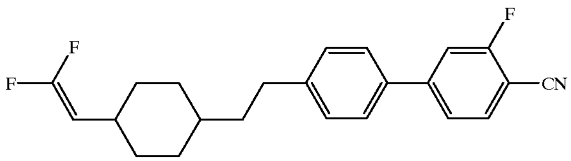
No. 65
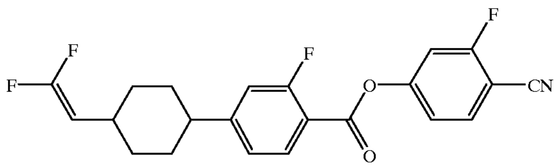
-continued
No. 66
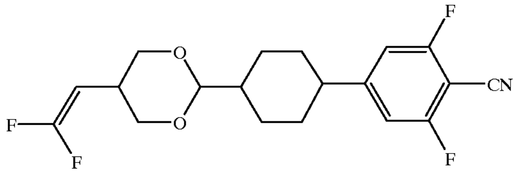
No. 67
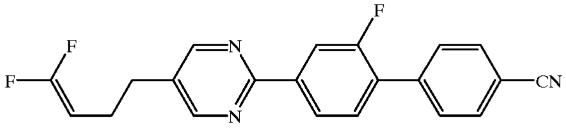
No. 68
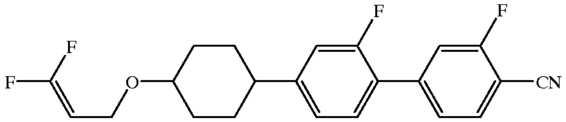
No. 69
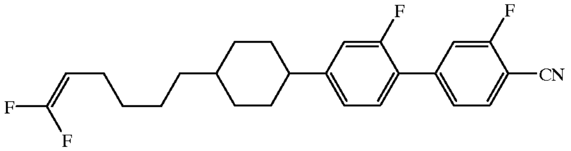
No. 70
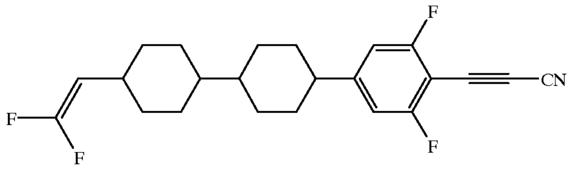
No. 71
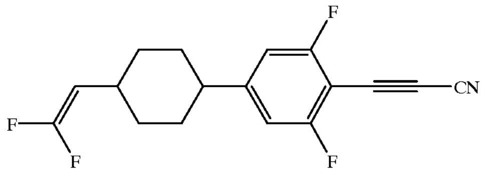
No. 72
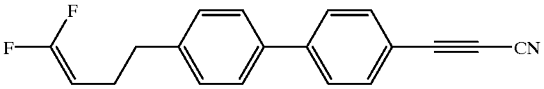
No. 73
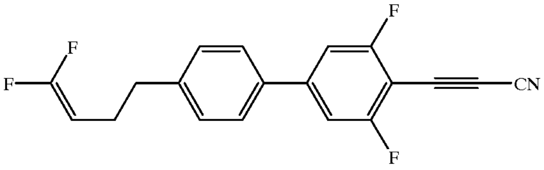
No. 74
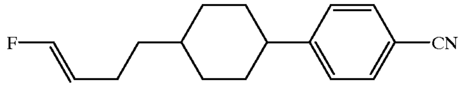

-continued

No. 75

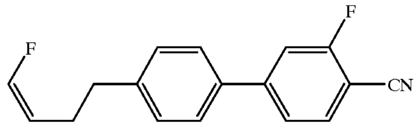

No. 76

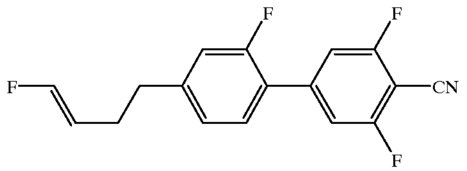

No. 77

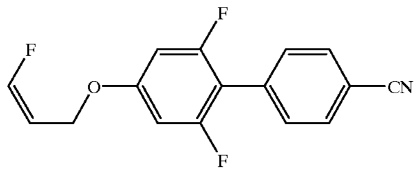

No. 78

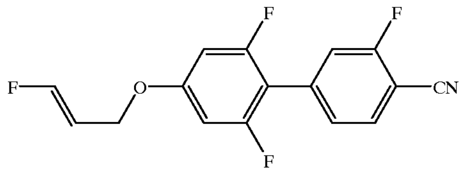

No. 79

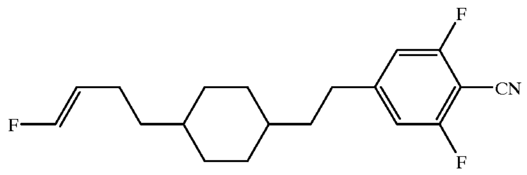

No. 80

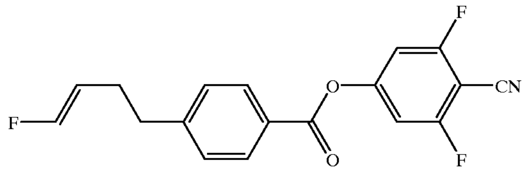

No. 81

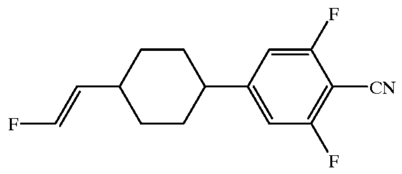

Example 5

Use Example 1

A nematic liquid crystal composition comprising cyanophenylcyclohexane type liquid crystalline compounds

| | |
|---|---|
| 4-(4-propylcyclohexyl)benzonitrile | 24% |
| 4-(4-pentylcyclohexyl)benzonitrile | 36% |
| 4-(4-heptylcyclohexyl)benzonitrile | 25% |
| 4-[4-(4-pentylcyclohexyl)phenyl]-benzonitrile | 15% |

(hereinafter referred to as "liquid crystal composition A1") has the following physical properties:

$T_{NI}$: 71.7° C., $V_{th}$ (cell thickness 8.8 μm): 1.78 V, Δε: 11.0, Δn: 0.137, η: 26.3 mPa·s.

A liquid crystal composition B1 consisting of 90% by weight of the liquid crystal composition A1 and 10% by weight of 1-(4,4-difluoro-3-butenyl)-3,5-difluoro-4-(4-cyalophenyl)benzene (No. 7) prepared in Example 1 was prepared. The physical properties of the composition B1 was as follows.

$T_{NI}$: 61.9° C., Vth (cell thickness 8.8 μm): 1.58 V, Δε: 12.3, Δn: 0.139, η: 30.3 mPa·s.

The physical properties of compound No. 7 calculated by the extrapolation based on the physical properties of these compositions A1 and B1 and the mixing ratio of the relevant compounds were as follows:

$T_{NI}$: −26.3° C., Δε: 24.0, Δn: 0.157, η: 60.0 mPa·s.

Example 6

Use Example 2

A liquid crystal composition B2 consisting of 85% by weight of the aforementioned liquid crystal composition A1 and 15% by weight of 1-(4,4-difluoro-3-butenyl)-3,5-difluoro-4-(3-fluoro-4-cyanophenyl)benzene (No. 8) prepared in Example 2 was prepared. The physical properties of the composition B2 was as follows:

$T_{NI}$: 52.5° C., $V_{th}$ (cell thickness 8.8 μm): 1.34 V, Δε: 14.0, Δn: 0.133, η: 33.1 mPa·s, $K_{33}/K_{11}$=2.6.

The physical properties of compound No. 8 calculated by the extrapolation based on the physical properties of these compositions Al and B2 and the mixing ratio of the relevant compounds were as follows:

$T_{NI}$: −56.3° C., Δε: 31.0, Δn: 0.110, η: 67.7 mPa·s.

Example 7

Use Example 3

A liquid crystal composition B3 consisting of 85% by weight of the liquid crystal composition A1 and 15% by weight of 1-(2,2-difluorovinyl)-4-(3,5-difluoro-4-cyanophenyl)cyclohexane (No. 53) prepared in Example 3 was prepared. The physical properties of the composition B3 was as follows:

$T_{NI}$: 50.8° C., $V_{th}$ (cell thickness 8.7 μm): 1.25 V, Δε: 12.1, Δn: 0.119, η: 29.3 mPa·s.

The physical properties of compound No. 8 calculated by the extrapolation based on the physical properties of these compositions Al and B3 and the mixing ratio of the relevant compounds were as follows:

$T_{NI}$: −67.6° C., Δε: 18.3, Δn: 0.017, η: 42.3 mPa·s.

Example 8

Comparative Example 1

A liquid crystal composition C1 was prepared following the procedures of Example 6, but using 1-(4,4-difluorobutenyl)-4-(4-cyanophenyl)cyclohexane (the aforementioned compound (1-a)) instead of the compound No. 8. The physical properties of the composition C1 was as follows:

$T_{NI}$: 66.3° C., $V_{th}$ (cell thickness 8.7 μm): 1.79 V, Δ∈: 10.7, Δn: 0.136, $K_{33}/K_{11}$=2.3.

The physical properties of the compound (1-a) calculated by the extrapolation based on the physical properties of the compositions used and the mixing ratio of the relevant compounds were as follows:

$T_{NI}$: 31.7° C., Δ∈: 9.0, Δn: 0.130.

Comparison of the above results with those of Examples 4–6 reveals that the compounds of the present invention have a larger Δ∈ than that of the conventional compounds and consequently are more effective in lowering the threshold voltage ($V_{TH}$) of the relevant compositions. It is further shown that the compound No. 8 has a larger $K_{33}/K_{11}$ ratio than that of the conventional compounds.

What is claimed is:

1. A fluoro-substituted alkenyl compound represented by the formula (1)

(1)

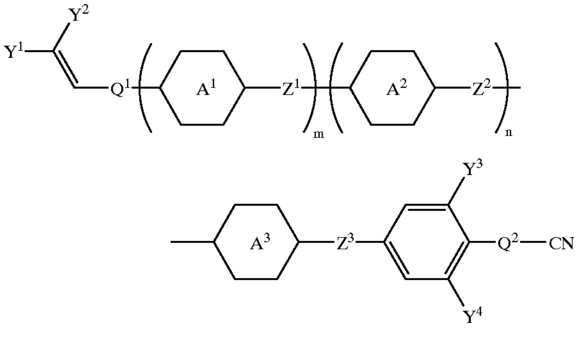

wherein both $Y^1$ and $Y^2$ are F, and $Y^3$ and $Y^4$ are each independently H or F, $Q^1$ is a single bond or an alkylene group of 1–20 carbon atoms, at least one —$CH_2$— being optionally substituted by —O—, provided that two or more —O— are not adjacent to each other;

$Q^2$ is a single bond or —C≡C—;

Rings $A^1$, $A^2$ and $A^3$ are each independently a cyclohexane ring, a dioxane ring, a cyclohexene ring, a pyrimidine ring, a pyridine ring, or a benzene ring, or a benzene ring having at least one hydrogen atom substituted by F;

$Z^1$, $Z^2$ and $Z^3$ are each independently a single bond, —$CH_2CH_2$—, —$CH_2O$—, —$OCH_2$—, —COO—, —OCO—, —CH=CH—, —C≡C—, —$CF_2O$—, or —$OCF_2$; and m and n are each independently 0 or 1;

provided that $Y^3$ is F when Ring $A^3$ is a cyclohexane ring and $Z^3$ is a single bond.

2. The fluoro-substituted alkenyl compound according to claim 1, wherein both m and n are 0.

3. The fluoro-substituted alkenyl compound according to claim 2, wherein Ring $A^3$ is a dioxane ring, a cyclohexene ring, a pyrimidine ring, a pyridine ring, a benzene ring, or a benzene ring having at least one hydrogen atom substituted by F.

4. The fluoro-substituted alkenyl compound according to claim 2, wherein Ring $A^3$ is a cyclohexane ring.

5. The fluoro-substituted alkenyl compound according to claim 4, wherein $Z^3$ is —COO—.

6. A liquid crystal composition which comprises at least two components, at least one of which is a fluoro-substituted alkenyl compound represented by the formula (1)

(1)

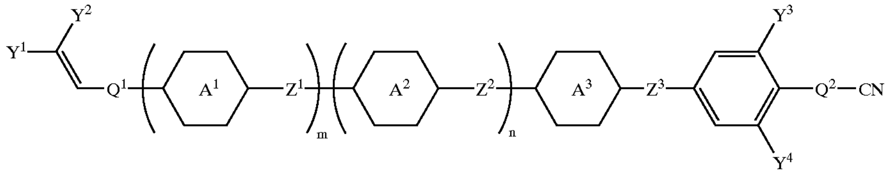

wherein both $Y^1$ and $Y^2$ are F, and $Y^3$ and $Y^4$ are each independently H or F, $Q^1$ is a single bond or an alkylene group of 1–20 carbon atoms, at least one —$CH_2$— being optionally substituted by —O—, provided that two or more —O— are not adjacent to each other;

$Q^2$ is a single bond or —C≡C—;

Rings $A^1$, $A^2$ and $A^3$ are each independently a cyclohexane ring, a dioxane ring, a cyclohexene ring, a pyrimidine ring, a pyridine ring, or a benzene ring, or a benzene ring having at least one hydrogen atom substituted by F;

$Z^1$, $Z^2$ and $Z^3$ are each independently a single bond, —$CH_2CH_2$—, —$CH_2O$—, —$OCH_2$—, —COO—, —OCO—, —CH=CH—, —C≡C—, —$CF_2O$—, or —$OCF_2$; and m and n are each independently 0 or 1;

provided that $Y^3$ is F when Ring $A^3$ is a cyclohexane ring and $Z^3$ is a single bond.

7. A liquid crystal composition which comprises as a first component at least one fluoro-substituted alkenyl compound set forth in any one of claims 1–5 and as a second component a compound selected from the group consisting of the compounds represented by the formulas (2), (3) and (4):

(2)

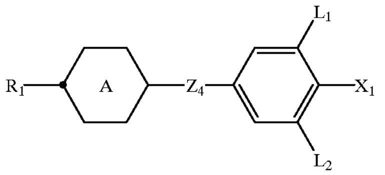

(3)

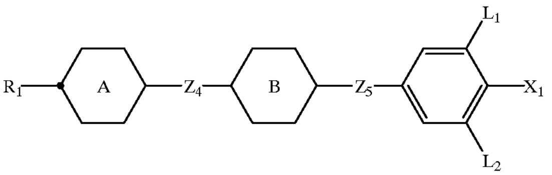

(4)

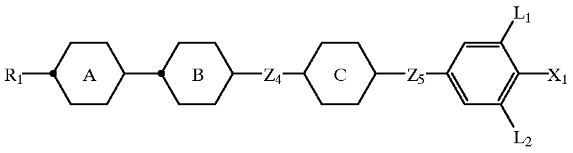

wherein $R_1$ is an alkyl group of 1–10 carbon atoms, at least one —$CH_2$— being optionally substituted by —O— or —CH═CH—, provided that two or more of—O— are not adjacent to each other, and at least one H atom being optionally substituted by F;

$X_1$ is F, Cl, $OCF_3$, —$OCF_2H$, —$CF_3$, —$CF_2H$, —$CFH_2$, —$OCF_2CF_2H$, or —$OCF_2CFHCF_3$;

$L_1$ and $L_2$ are each independently H or F;

$Z_4$ and $Z_5$ are each independently —$(CH_2)_2$, —$(CH_2)_4$—, —COO—, —$CF_2O$—, —$OCF_2$—, —CH═CH—, or a single bond;

Rings A and B are each independently a cyclohexane ring, a dioxane ring, or a benzene ring, or a benzene ring having at least one hydrogen atom substituted by F; and Ring C is a cyclohexane ring, a benzene ring, or a benzene ring having at least one hydrogen atom substituted by F.

8. A liquid crystal composition which comprises as a first component at least one fluoro-substituted alkenyl compound set forth in any one of claims 1–5 and as a second component a compound selected from the group consisting of the compounds represented by the formulas (5) and (6):

(5)

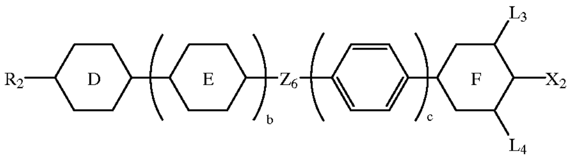

-continued (6)

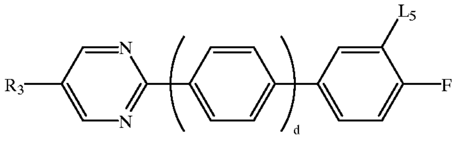

wherein $R_2$ and $R_3$ are each independently an alkyl group of 1–10 carbon atoms, at least one —$CH_2$— being optionally substituted by —O— or —CH═CH—, provided that two or more of—O— are not adjacent to each other, and at least one H atom being optionally substituted by F;

$X_2$ is —CN or —C≡C—CN;

Ring D is a cyclohexane ring, a benzene ring, a dioxane ring, or a pyrimidine ring;

Ring E is a cyclohexane ring, a benzene ring, a benzene ring having at least one hydrogen atom substituted by F, or a pyrimidine ring;

Ring F is a cyclohexane ring or a benzene ring;

$Z_6$ is —$(CH_2)_2$—, —COO—, —$CF_2O$—, —$OCF_2$—, or a single bond;

$L_3$, $L_4$ and $L_5$ are each independently H or F; and b, c and d are each independently 0 or 1.

9. A liquid crystal composition which comprises as a first component at least one fluoro-substituted alkenyl compound set forth in any one of claims 1–5 and as a second component a compound selected from the group consisting of the compounds represented by the formulas (7), (8) and (9):

(7)

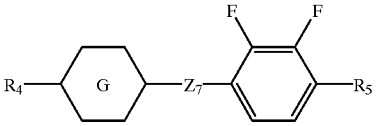

(8)

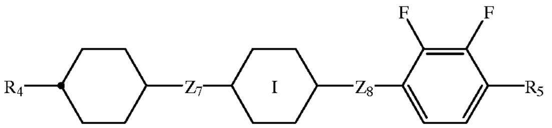

(9)

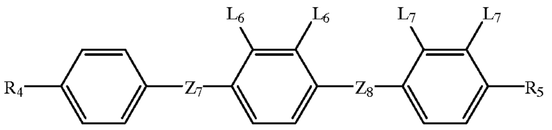

wherein $R_4$ and $R_5$ are each independently an alkyl group of 1–10 carbon atoms, at least one —$CH_2$— being optionally substituted by —O— or —CH═CH—, provided that two or more of—O— are not adjacent to each other, and at least one H atom being optionally substituted by F;

Rings G and I are each independently a cyclohexane ring or a benzene ring;

$L_6$ and $L_7$ are each independently H or F, provided that $L_6$ and $L_7$ are not simultaneously H; and $Z_7$ and $Z_8$ are each independently —$(CH_2)_2$—, —COO—, or a single bond.

10. The liquid crystal composition according to claim 7, which further comprises as a third component a compound selected from the group consisting of the compounds represented by the formulas (10), (11) and (12):

(10)

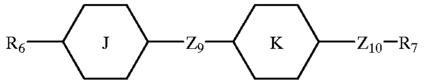

(11)

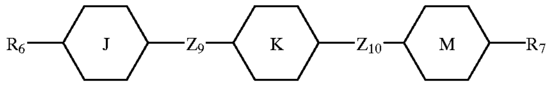

(12)

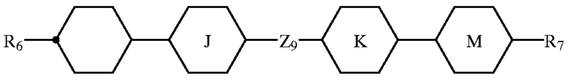

wherein $R_6$ and $R_7$ are each independently an alkyl group of 1–10 carbon atoms, provided that at least one of —$CH_2$— groups in the substituted group may be substituted for an —O— group or a —CH═CH— group each but two or more of the substituted —O— groups are not adjacent to each other, and at least one of H atoms in these groups may be substituted for F;

Rings J, K and M are each independently a cyclohexane ring, pyrimidine ring, a benzene ring, or a benzene ring having not less than one H atoms thereof substituted for F; and $Z_9$ and $Z_{10}$ are each independently —C≡C—, —COO—, —$(CH_2)_2$—, —CH═CH—, or a single bond.

11. The liquid crystal composition according to claim 8, which further comprises as a third component a compound selected from the group consisting of the compounds represented by the formulas (10), (11) and (12):

(10)

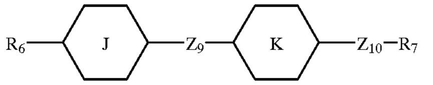

(11)

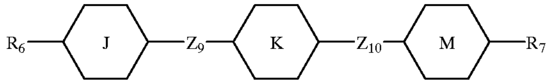

(12)

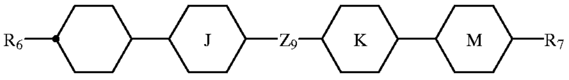

wherein $R_6$ and $R_7$ are each independently an alkyl group of 1–10 carbon atoms, at least one —$CH_2$— being optionally substituted by —O— or —CH═CH—, provided that two or more of —O— are not adjacent to each other, and any of H atoms in the group being optionally substituted by F;

Rings J, K and M are each independently a cyclohexane ring, pyrimidine ring, a benzene ring, or a benzene ring having at least one H atom substituted by F; and $Z_9$ and $Z_{10}$ are each independently —C≡C—, —COO—, —$(CH_2)_2$—, —CH═CH—, or a single bond.

12. The liquid crystal composition according to claim 9, which further comprises as a third component a compound selected from the group consisting of the compounds represented by the formulas (10), (11) and (12):

(10)

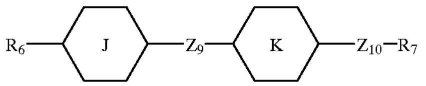

(11)

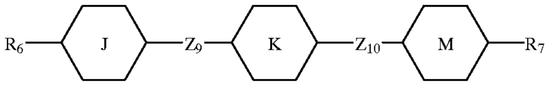

(12)

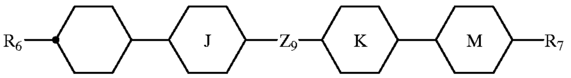

wherein $R_6$ and $R_7$ are each independently an alkyl group of 1–10 carbon atoms, at least one —$CH_2$— being optionally substituted by —O— or —CH═CH—, provided that two or more of —O— are not adjacent to each other, and any of H atoms in the group being optionally substituted by F;

Rings J, K and M are each independently a cyclohexane ring, pyrimidine ring, a benzene ring, or a benzene ring having at least one H atom substituted by F; and $Z_9$ and $Z_{10}$ are each independently —C≡C—, —COO—, —$(CH_2)_2$—, —CH═CH—, or a single bond.

13. The liquid crystal composition according to claim 7, which further comprises as a third component a compound selected from the group consisting of the compounds represented by the formulas (5) and (6):

(5)

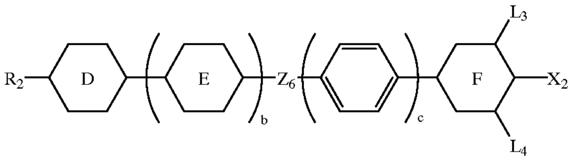

(6)

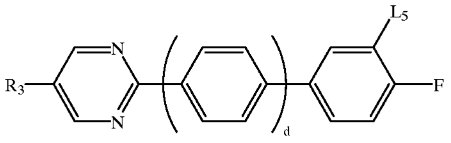

wherein $R_2$ and $R_3$ are each independently an alkyl group of 1–10 carbon atoms, at least one —$CH_2$— being optionally substituted by —O— or —CH═CH—, provided that two or more of —O— are not adjacent to each other, and at least one H atom being optionally substituted by F;

$X_2$ is —CN or —C≡C—CN;

Ring D is a cyclohexane ring, a benzene ring, a dioxane ring, or a pyrimidine ring;

Ring E is a cyclohexane ring, a benzene ring, a benzene ring having at least one hydrogen atom substituted by F, or a pyrimidine ring;

Ring F is a cyclohexane ring or a benzene ring;

$Z_6$ is —$(CH_2)_2$—, —COO—, —$CF_2O$—, —$OCF_2$—, or a single bond;

$L_3$, $L_4$ and $L_5$ are each independently H or F; and b, c and d are each independently 0 or 1, and as a fourth component at least one compound selected from the group consisting of the compounds represented by the formulas (10), (11) and (12):

(10)

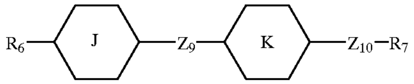

(11)

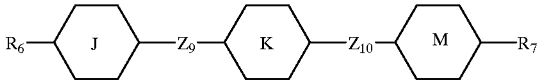

(12)

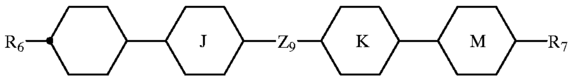

wherein $R_6$ and $R_7$ are each independently an alkyl group of 1–10 carbon atoms, at least one —$CH_2$— being optionally substituted by —O— or —CH═CH—, provided that two or more of —O— are not adjacent to each other, and any of H atoms in the group being optionally substituted by F;

Rings J, K and M are each independently a cyclohexane ring, pyrimidine ring, a benzene ring, or a benzene ring having at least one H atom substituted by F; and $Z_9$ and $Z_{10}$ are each independently —C≡C—, —COO—, —$(CH_2)_2$—, —CH═CH—, or a single bond.

14. The liquid crystal composition according to claim 6, which further comprises at least one optically active compound.

15. A liquid crystal display element comprising the liquid crystal composition set forth in claim 6.

16. The liquid crystal composition according to claim 7, which further comprises at least one optically active compound.

17. The liquid crystal composition according to claim 8, which further comprises at least one optically active compound.

18. The liquid crystal composition according to claim 9, which further comprises at least one optically active compound.

19. The liquid crystal composition according to claim 10, which further comprises at least one optically active compound.

20. The liquid crystal composition according to claim 11, which further comprises at least one optically active compound.

21. The liquid crystal composition according to claim 12, which further comprises at least one optically active compound.

22. The liquid crystal composition according to claim 13, which further comprises at least one optically active compound.

23. A liquid crystal display element comprising the liquid crystal composition set forth in claim 7.

24. A liquid crystal display element comprising the liquid crystal composition set forth in claim 8.

25. A liquid crystal display element comprising the liquid crystal composition set forth in claim 9.

26. A liquid crystal display element comprising the liquid crystal composition set forth in claim 10.

27. A liquid crystal display element comprising the liquid crystal composition set forth in claim 11.

28. A liquid crystal display element comprising the liquid crystal composition set forth in claim 12.

29. A liquid crystal display element comprising the liquid crystal composition set forth in claim 13.

30. A liquid crystal display element comprising the liquid crystal composition set forth in claim 14.

* * * * *